US009904167B2

(12) United States Patent
Tsuchimura

(10) Patent No.: US 9,904,167 B2
(45) Date of Patent: Feb. 27, 2018

(54) COMPOUND, ACTIVE LIGHT SENSITIVE OR RADIATION SENSITIVE RESIN COMPOSITION, RESIST FILM USING SAME, RESIST-COATED MASK BLANK, PHOTOMASK, PATTERN FORMING METHOD, METHOD FOR MANUFACTURING ELECTRONIC DEVICE, AND ELECTRONIC DEVICE

(71) Applicant: FUJIFILM Corporation, Tokyo (JP)

(72) Inventor: Tomotaka Tsuchimura, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/982,759

(22) Filed: Dec. 29, 2015

(65) Prior Publication Data

US 2016/0116840 A1 Apr. 28, 2016

Related U.S. Application Data

(63) Continuation of application No. PCT/JP2014/065498, filed on Jun. 11, 2014.

(30) Foreign Application Priority Data

Jul. 10, 2013 (JP) ................................. 2013-145015
Feb. 14, 2014 (JP) ................................. 2014-026904

(51) Int. Cl.

| | |
|---|---|
| ***G03F 7/004*** | (2006.01) |
| ***H01L 21/027*** | (2006.01) |
| ***C07D 327/08*** | (2006.01) |
| ***C07C 309/15*** | (2006.01) |
| ***C07D 333/76*** | (2006.01) |

(Continued)

(52) U.S. Cl.

CPC ............ *G03F 7/0045* (2013.01); *C07C 25/18* (2013.01); *C07C 309/15* (2013.01); *C07C 309/19* (2013.01); *C07C 311/14* (2013.01); *C07C 311/16* (2013.01); *C07C 311/48* (2013.01); *C07C 311/51* (2013.01); *C07C 321/28* (2013.01); *C07C 323/09* (2013.01); *C07C 323/20* (2013.01); *C07C 327/22* (2013.01); *C07C 327/24* (2013.01); *C07C 327/26* (2013.01); *C07C 381/12* (2013.01); *C07D 209/48* (2013.01); *C07D 327/08* (2013.01); *C07D 333/46* (2013.01); *C07D 333/76* (2013.01); *C07D 335/16* (2013.01); *C07D 339/08* (2013.01); *C07D 347/00* (2013.01); *C07D 493/08* (2013.01); *C07J 31/006* (2013.01); *C07J 41/0055* (2013.01); *C07J 41/0061* (2013.01); *G03F 7/0382* (2013.01); *G03F 7/0392* (2013.01); *G03F 7/0397* (2013.01); *H01L 21/0271* (2013.01); *H01L 21/0276* (2013.01); *H01L 29/16* (2013.01); *C07C 2601/08* (2017.05); *C07C 2601/14* (2017.05); *C07C 2602/42* (2017.05);

(Continued)

(58) Field of Classification Search

CPC ...... G03F 7/004; G03F 7/0045; G03F 7/0382; G03F 7/0397; C07C 381/12; C08F 220/30; H01L 21/0271

USPC ............ 430/270.1, 322, 325, 329, 330, 913; 526/319, 326, 346; 560/129, 14, 15, 19; 562/625

See application file for complete search history.

(56) References Cited

U.S. PATENT DOCUMENTS 4,015,991 A * 4/1977 Persinski ................ C09K 8/46 166/293
4,167,618 A 9/1979 Schmitt et al.

(Continued)

FOREIGN PATENT DOCUMENTS

JP 6-501970 A 3/1994
JP 2005148291 A * 6/2005

(Continued)

OTHER PUBLICATIONS

Machine translation of JP 2007-291032 (no date).*
International Search Report dated Sep. 16, 2014 issued by International Searching Authority in counterpart International Patent Application No. PCT/JP2014/065498 (PCT/ISA/210).
Written Opinion dated Sep. 16, 2014 issued by International Searching Authority in counterpart International Patent Application No. PCT/JP2014/065498 (PCT/ISA/237).

(Continued)

*Primary Examiner* — Amanda C. Walke
(74) *Attorney, Agent, or Firm* — Sughrue Mion, PLLC

(57) ABSTRACT

Provided is an active light sensitive or radiation sensitive resin composition which contains a compound (A) represented by General Formula (I) or (II):

(I)

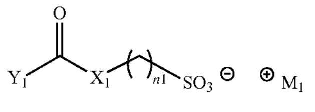

(II)

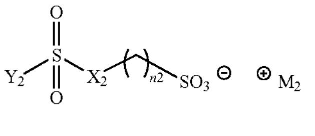

in the formulae, each of $Y_1$ and $Y_2$ represents a monovalent organic group; each of $M_1^+$ and $M_2^+$ represents an organic onium ion; each of $X_1$ and $X_2$ represents a group that is represented by —S—, —NH—, or —$NR^1$—; $R^1$ represents a monovalent organic group; each of n1 and n2 represents an integer of 1 or more; and $R^1$ and $Y_1$ or $Y_2$ may bond with each other to form a ring.

17 Claims, No Drawings

(51) Int. Cl.

| | |
|---|---|
| ***C07C 311/16*** | (2006.01) |
| ***C07C 327/24*** | (2006.01) |
| ***C07C 381/12*** | (2006.01) |
| ***C07D 209/48*** | (2006.01) |
| ***C07D 333/46*** | (2006.01) |
| ***C07D 335/16*** | (2006.01) |
| ***C07D 339/08*** | (2006.01) |
| ***C07C 311/14*** | (2006.01) |
| ***C07D 347/00*** | (2006.01) |
| ***C07C 311/48*** | (2006.01) |
| ***C07C 311/51*** | (2006.01) |
| ***C07C 327/22*** | (2006.01) |
| ***C07C 327/26*** | (2006.01) |
| ***C07D 493/08*** | (2006.01) |
| ***C07C 25/18*** | (2006.01) |
| ***C07J 31/00*** | (2006.01) |
| ***C07J 41/00*** | (2006.01) |
| ***C07C 309/19*** | (2006.01) |
| ***C07C 321/28*** | (2006.01) |
| ***C07C 323/09*** | (2006.01) |
| ***C07C 323/20*** | (2006.01) |
| ***H01L 29/16*** | (2006.01) |
| ***G03F 7/038*** | (2006.01) |
| ***G03F 7/039*** | (2006.01) |

(52) U.S. Cl.

CPC ...... *C07C 2603/18* (2017.05); *C07C 2603/24* (2017.05); *C07C 2603/74* (2017.05)

(56) References Cited

U.S. PATENT DOCUMENTS

| | | | | |
|---|---|---|---|---|
| 5,382,647 | A | 1/1995 | Daute et al. | |
| 5,464,735 | A | 11/1995 | Preddy et al. | |
| 8,283,106 | B2 * | 10/2012 | Maeda | C07C 309/12 430/270.1 |
| 8,420,292 | B2 * | 4/2013 | Harada | C08F 14/18 430/270.1 |
| 8,900,794 | B2 * | 12/2014 | Aqad | C07D 313/08 430/270.1 |
| 2006/0166135 | A1 | 7/2006 | Wada | |
| 2006/0210921 | A1 | 9/2006 | Watanabe | |
| 2009/0111047 | A1 | 4/2009 | Yamashita | |
| 2010/0143830 | A1 | 6/2010 | Ohashi et al. | |
| 2010/0304303 | A1 * | 12/2010 | Maeda | C07C 309/12 430/286.1 |
| 2012/0196228 | A1 | 8/2012 | Nagasawa et al. | |
| 2012/0301817 | A1 * | 11/2012 | Inasaki | C08F 8/00 430/5 |
| 2013/0084525 | A1 * | 4/2013 | Aqad | C07D 313/08 430/270.1 |
| 2013/0209922 | A1 * | 8/2013 | Masunaga | G03F 7/0382 430/5 |
| 2013/0302726 | A1 * | 11/2013 | Tsuchimura | G03F 1/76 430/5 |
| 2013/0344438 | A1 * | 12/2013 | Aqad | G03F 7/004 430/281.1 |
| 2014/0030640 | A1 * | 1/2014 | Tsuchihashi | C08F 8/14 430/5 |
| 2015/0056558 | A1 | 2/2015 | Aqad et al. | |
| 2015/0086911 | A1 * | 3/2015 | Tsuruta | C07D 327/08 430/5 |
| 2016/0046749 | A1 * | 2/2016 | Kramer | C08F 222/10 526/204 |

FOREIGN PATENT DOCUMENTS

| | | | | |
|---|---|---|---|---|
| JP | 2006-201711 | A | | 8/2006 |
| JP | 2006-258980 | A | | 9/2006 |
| JP | 2007291032 | A | * | 11/2007 |
| JP | 2009-109595 | A | | 5/2009 |
| JP | 2010132560 | A | * | 6/2010 |
| JP | 2010-155824 | A | | 7/2010 |
| JP | 2012-168502 | A | | 9/2012 |
| KR | 10-2006-0085595 | A | | 7/2006 |
| TW | 200639587 | A | | 11/2006 |
| TW | 201319024 | A1 | | 5/2013 |
| WO | 2014/034190 | A1 | | 3/2014 |

OTHER PUBLICATIONS

English Translation of Written Opinion dated Sep. 16, 2014, issued by the International Searching Authority in counterpart International Application No. PCT/JP2014/065498 (PCT/ISA/237).

Communication issued Oct. 11, 2016, issued by the Japanese Patent Office in counterpart Japanese Patent Application No. 2014-026904.

Office Action dated Apr. 13, 2017, issued by the Korean Intellectual Property Office in counterpart Korean Patent Application No. 10-2015-7036193.

Office Action dated Oct. 17, 2017, issued by the Korean Intellectual Property Office in corresponding Korean Application No. 10-2015-7036193.

Office Action issued by the Taiwan Intellectual Property Office dated Oct. 24, 2017 in counterpart Taiwanese Patent Application No. 103123667.

* cited by examiner

COMPOUND, ACTIVE LIGHT SENSITIVE OR RADIATION SENSITIVE RESIN COMPOSITION, RESIST FILM USING SAME, RESIST-COATED MASK BLANK, PHOTOMASK, PATTERN FORMING METHOD, METHOD FOR MANUFACTURING ELECTRONIC DEVICE, AND ELECTRONIC DEVICE

CROSS REFERENCE TO RELATED APPLICATION

This is a continuation of International Application No. PCT/JP2014/065498 filed on Jun. 11, 2014, and claims priority from Japanese Patent Application No. 2013-145015 filed on Jul. 10, 2013 and Japanese Patent Application No. 2014-026904 filed on Feb. 14, 2014, the entire disclosures of which are incorporated herein by reference.

BACKGROUND OF THE INVENTION

1. Field of the Invention

The present invention relates to a compound, an active light sensitive or radiation sensitive resin composition, a resist film using the same, a resist-coated mask blank, a photomask, a pattern forming method, a method for manufacturing electronic device, and an electronic device, which are suitable for use in super-micro lithographic processes and other fabrication processes such as for manufacturing super LSIs or high capacity microchips and are capable of forming a high-definition pattern using electron beams or extreme ultraviolet light.

2. Description of the Related Art

In fine processing using resist compositions, there is an increasing demand to form ultrafine patterns as the integration of integrated circuits increases. Therefore, exposure wavelengths have been shortened with the light for exposure being changed from the g-line to the i-line, and then to excimer laser light and, currently, for example, the lithography techniques using electron beams are being developed.

Resist films subjected to exposure with excimer laser light or electron beams are usually formed of chemical amplified resist compositions. Various compounds are being developed as photoacid generators which are the main constituent components of the chemical amplified resist compositions. For example, techniques in which a sulfonium salt having a specific structure is used as a photoacid generator in order to form a favorable pattern are known (for example, refer to JP2010-155824A and JP2012-168502A).

SUMMARY OF THE INVENTION

However, from the viewpoint of the overall performance as a resist, finding an appropriate combination of the resin, the photoacid generator, the basic compound, the additives, the solvent, and the like to be used is difficult, in particular, in consideration of the current demand for forming ultrafine (for example, a line width of 50 nm or less) patterns with high resolution (for example, high resolving power), excellent pattern shape, and low line edge roughness (LER), there is room for improvement in practice.

An object of the present invention is to provide a compound and an active light sensitive or radiation sensitive resin composition which are able to form ultrafine (for example, a line width of 50 nm or less) patterns in a state in which high resolution (for example, high resolving power), excellent pattern shape, and low line edge roughness (LER) are satisfied at the same time.

Another object of the present invention is to provide a resist film using the active light sensitive or radiation sensitive resin composition described above, a resist-coated mask blank, a photomask, a pattern forming method, a method for manufacturing an electronic device, and an electronic device.

As a result of intensive research, the present inventors found that the objects described above were achieved using an active light sensitive or radiation sensitive resin composition which contains a compound with a specific structure.

That is, the present invention is as follows.

[1] An active light sensitive or radiation sensitive resin composition including a compound (A) represented by General Formula (I) or (II) below, (I)

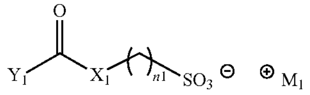

(II)

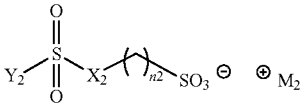

(in the formulae, each of $Y_1$ and $Y_2$ represents a monovalent organic group; each of $M_1^+$ and $M_2^+$ represents an organic onium ion; each of $X_1$ and $X_2$ represents a group which is represented by —S—, —NH—, or —$NR^1$—; $R^1$ represents a monovalent organic group; each of n1 and n2 represents an integer of 1 or more; and $R^1$ and $Y_1$ or $Y_2$ may bond with each other to form a ring).

[2] The active light sensitive or radiation sensitive resin composition according to [1], in which, in General Formula (I) or (II), $X_1$ or $X_2$ is a group which is represented by —NH— or —$NR^1$—.

[3] The active light sensitive or radiation sensitive resin composition according to [1], in which, in General Formula (I) or (II), $X_1$ or $X_2$ is a group which is represented by —S—.

[4] The active light sensitive or radiation sensitive resin composition according to any one of [1] to [3], in which, in General Formula (I) or (H), $Y_1$ or $Y_2$ is an aryl group or a monovalent hydrocarbon group which has an alicyclic hydrocarbon structure having 5 or more carbon atoms.

[5] The active light sensitive or radiation sensitive resin composition according to any one of [1] to [4], further including a compound (B) which has a phenolic hydroxyl group.

[6] The active light sensitive or radiation sensitive resin composition according to [5], in which the compound (B) is a resin which has a repeating unit represented by General Formula (1) below, (1)

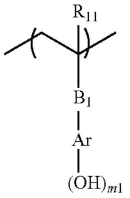

in General Formula (1), $R_{11}$ represents a hydrogen atom, a methyl group, or a halogen atom; $B_1$ represents a single bond or a divalent linking group; Ar represents an aromatic ring; and m1 represents an integer of 1 or more.

[7] The active light sensitive or radiation sensitive resin composition according to [5] or [6], in which the compound (B) is a resin which has a repeating unit represented by General Formula (A) below, (A)

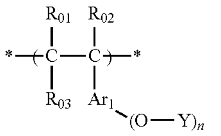

in General Formula (A), $R_{01}$, $R_{02}$, and $R_{03}$ each independently represent a hydrogen atom, an alkyl group, a cycloalkyl group, a halogen atom, a cyano group, or an alkoxycarbonyl group; $Ar_1$ represents an aromatic ring group; $R_{03}$ and $Ar_1$ may bond with each other to form a 5- or 6-membered ring with a main chain of the repeating unit represented by General Formula (A); n Y's each independently represent a hydrogen atom or a group which is released due to an action of an acid; here, at least one Y represents a group which is released due to an action of an acid; and n represents an integer of 1 to 4.

[8] The active light sensitive or radiation sensitive resin composition according to any one of [1] to [7], further including an acid cross-linkable compound (C).

[9] The active light sensitive or radiation sensitive resin composition according to [8], in which the compound (C) is a compound which has two or more hydroxymethyl groups or alkoxymethyl groups in a molecule.

[10] The active light sensitive or radiation sensitive resin composition according to any one of [1] to [9], which is used for exposure to electron beams or extreme ultraviolet light.

[11] A resist film formed using the active light sensitive or radiation sensitive resin composition according to any one of [1] to [10].

[12] A resist-coated mask blank coated with the resist film according to [11].

[13] A photomask obtained by exposing and developing the resist-coated mask blank according to [12].

[14] A pattern forming method including exposing the resist film according to [11]; and developing the exposed film.

[15] A pattern forming method including exposing the resist-coated mask blank according to [12]; and developing the exposed mask blank.

[16] A method for manufacturing an electronic device, including the pattern forming method according to [14] or [15].

[17] An electronic device manufactured using the method for manufacturing an electronic device according to [16].

[18] A compound represented by General Formula (I-I) below, (I-I)

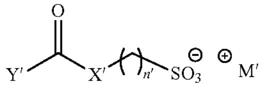

(in the formula, X' represents —S— or —NH—; n' represents an integer of 1 to 3; Y' represents an aryl group or a monovalent hydrocarbon group which has an alicyclic hydrocarbon structure having 5 or more carbon atoms; and $M'^{+}$ represents a sulfonium cation or an iodonium cation.)

According to the present invention, it is possible to provide a compound and an active light sensitive or radiation sensitive resin composition which are able to form ultrafine (for example, a line width of 50 nm or less) patterns in a state in which high resolution (for example, high resolving power), excellent pattern shape, and low line edge roughness (LER) are satisfied at the same time.

In addition, according to the present invention, it is possible to provide a resist film using the active light sensitive or radiation sensitive resin composition described above, a resist-coated mask blank, a photomask, a pattern forming method, a method for manufacturing an electronic device, and an electronic device.

DESCRIPTION OF THE PREFERRED EMBODIMENTS

Detailed description will be given below of aspects embodying the present invention.

Here, in the notation of the groups (atomic groups) in the present specification, notation which does not indicate whether a group is substituted or unsubstituted encompasses a group having a substituent group as well as a group not having a substituent group. For example, an "alkyl group" encompasses not only an alkyl group which does not have a substituent group (an unsubstituted alkyl group), but also an alkyl group which has a substituent group (a substituted alkyl group).

The "active light" or "radiation" in the present invention has the meaning of, for example, the bright line spectrum of a mercury lamp, far ultraviolet rays which are represented by an excimer laser, extreme ultraviolet rays (EUV light), X-rays, electron beams, and the like. In addition, "light" in the present invention has the meaning of active light or radiation. In addition, unless otherwise stated, "exposure" in the present specification includes not only exposure using a mercury lamp, far ultraviolet rays which are represented by an excimer laser, X-rays, EUV light, and the like, but also drawing using particle beams such as electron beams and ion beams.

The active light sensitive or radiation sensitive resin composition according to the present invention contains a compound which is represented by General Formula (I) or (II) below.

(I)

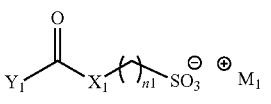

(II)

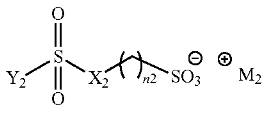

(In the formulae, $Y_1$ and $Y_2$ represent a monovalent organic group; $M_1^{+}$ and $M_2^{+}$ represent an organic onium ion; $X_1$ and $X_2$ represent a group which is represented by —S—, —NH—, or —$NR^1$—; $R^1$ represents a monovalent organic group; n1 and n2 represent an integer of 1 or more; and $R^1$ and $Y_1$ or $Y_2$ may bond with each other to form a ring.)

According to this configuration, it is possible to provide an active light sensitive or radiation sensitive resin composition which is able to form ultrafine (for example, a line width of 50 nm or less) patterns in a state in which high resolution (for example, high resolving power), excellent pattern shape, and low line edge roughness (LER) are satisfied at the same time. The reason is not clear, but is presumed to be as follows.

The active light sensitive or radiation sensitive resin composition typically contains the compound (B) to be described below; however, since, in the compound which is represented by General Formula (I) or (II), $X_1$ and $X_2$ represent a group which is represented by —S—, —NH—, or —$NR^1$—, the polarity of the compound which is represented by General Formula (I) or (II) increases and it is considered that an intermolecular interaction such as hydrogen bonding or dipole-dipole interaction with the compound (B) which has a phenolic hydroxyl group occurs.

Due to this, it is considered that, in a case of forming a resist film using the active light sensitive or radiation sensitive resin composition described above, the compound which is represented by General Formula (I) or (II) described above is evenly distributed in the film, and the pattern shape is improved and the line edge roughness (LER) is reduced as a result.

In addition, as described above, it is considered that, due to the interaction between the compound (B) and the compound which is represented by General Formula (I) or (II) becoming stronger, the acid diffusibility is suppressed and the resolution is improved as a result.

The active light sensitive or radiation sensitive resin composition according to the present invention is preferably used for exposure to electron beams or extreme ultraviolet light.

The active light sensitive or radiation sensitive resin composition of the present invention is typically a resist composition, and may be used as a positive type resist composition or may be used as a negative type resist composition.

More specifically, as described below, in a case where the active light sensitive or radiation sensitive resin composition which contains a compound which is represented by General Formula (I) or (II) contains an acid-decomposable resin to be described below and is subjected to alkali development, the composition may be used as a positive type active light sensitive or radiation sensitive resin composition.

Meanwhile, in a case where the active light sensitive or radiation sensitive resin composition which contains a compound which is represented by General Formula (I) or (II) contains an acid-decomposable resin to be described below and is subjected to development using an organic developer, the composition may be used as a negative type active light sensitive or radiation sensitive resin composition.

Furthermore, when the active light sensitive or radiation sensitive resin composition which contains a compound which is represented by General Formula (I) or (II) contains the compound (B) and the acid cross-linkable compound (C) to be described below, the composition may be used as a negative type active light sensitive or radiation sensitive resin composition, in a case of being subjected to alkali development or in a case of being subjected to development using an organic developer.

In addition, the composition according to the present invention is typically a chemical amplified resist composition.

Detailed description will be given below of each component of the active light sensitive or radiation sensitive resin composition of the present invention.

[1] Compound(A) Represented by General Formula (I) or (II)

The active light sensitive or radiation sensitive resin composition of the present invention contains a compound (referred to below as "compound (A)") which is represented by General Formula (I) or (II) described above as the photoacid generator.

$X_1$ and $X_2$ represent a group which is represented by —S—, —NH—, or —$NR^1$—.

$X_1$ and $X_2$ are preferably —S— or —NH—. $X_1$ and $X_2$ are preferably —NH— or —$NR^1$— from the point of view of improving the resolving power, and more preferably —S— from the point of view improving the LER performance.

Examples of the monovalent organic group represented by $R^1$ include an alkyl group, a cycloalkyl group, an aryl group, an acyl group, an alkylsulfonyl group, an arylsulfonyl group, and the like.

The number of carbon atoms in the alkyl group is preferably 3 to 10. In particular, in a case where the alkyl group has a branched structure, an alkyl group having 3 to 8 carbon atoms is preferable.

Examples of the alkyl group include a propyl group, an isopropyl group, an n-butyl group, an s-butyl group, an isobutyl group, a tert-butyl group, a pentyl group, an isopentyl group, a neopentyl group, a 1,1-dimethylpropyl group, a hexyl group, a 2-ethylhexyl group, an octyl group, and the like, and preferable examples thereof include an isopropyl group, a tert-butyl group, and a neopentyl group.

The number of carbon atoms of the cycloalkyl group is preferably 5 to 16. Examples of the cycloalkyl group include a cyclohexyl group, a cyclopentyl group, an adamantyl group, and a norbornyl group, and preferable examples thereof include a cyclohexyl group, an adamantyl group, and a norbornyl group.

The number of carbon atoms of the aryl group is preferably 6 to 12, more preferably 6 to 8, and even more preferably 6 or 7. Examples of the aryl group include a phenyl group, a naphthyl group, and the like, and preferable examples thereof include a phenyl group.

Examples of the acyl group include an acetyl group, a propanoyl group, a butanoyl group, a trifluoromethyl carbonyl group, a pentanoyl group, a benzoyl group, a 1-naphthoyl group, a 2-naphthoyl group, a 4-methylsulfanyl benzoyl group, a 4-phenylsulfanyl benzoyl group, a 4-dimethylamino benzoyl group, a 4-diethylamino benzoyl group, a 2-chlorobenzoyl group, a 2-methylbenzoyl group, a 2-methoxybenzoyl group, a 2-butoxybenzoyl group, a 3-chlorobenzoyl group, a 3-trifluoromethyl benzoyl group, a 3-cyanobenzoyl group, a 3-nitrobenzoyl group, a 4-fluorobenzoyl group, a 4-cyanobenzoyl group, a 4-methoxybenzoyl group, and the like.

The alkylsulfonyl group may have a substituent group, an alkyl sulfonyl group having 1 to 20 carbon atoms is preferable, and examples thereof include a methyl sulfonyl group, an ethyl sulfonyl group, a propyl sulfonyl group, an isopropyl sulfonyl group, a butyl sulfonyl group, a hexyl sulfonyl group, a cyclohexyl sulfonyl group, an octyl sulfonyl group, a 2-ethylhexyl sulfonyl group, a decanoyl sulfonyl group, a dodecanoyl sulfonyl group, an octadecanoyl sulfonyl group, a cyanomethyl sulfonyl group, a methoxymethyl sulfonyl group, a perfluoroalkyl sulfonyl group, or the like (for example, a trifluoromethyl sulfonyl group, or an n-nonafluorobutyl sulfonyl group).

The arylsulfonyl group may have a substituent group, an arylsulfonyl group having 6 to 30 carbon atoms is preferable, and examples thereof include a phenyl sulfonyl group, a 1-naphthylsulfonyl group, a 2-naphthyl sulfonyl group, a 2-chlorophenyl sulfonyl group, a 2-methylphenyl sulfonyl group, a 4-methylphenyl sulfonyl group, a 2-methoxyphenyl sulfonyl group, a 2-butoxyphenyl sulfonyl group, a 3-chlorophenyl sulfonyl group, a 3-trifluoromethylphenyl sulfonyl group, a 3-cyanophenyl sulfonyl group, a 3-nitrophenyl sulfonyl group, a 4-fluorophenyl sulfonyl group, a 4-cyanophenyl sulfonyl group, a 4-methoxyphenyl sulfonyl group, a 4-methylsulfanylphenyl sulfonyl group, a 4-phenylsulfanylphenyl sulfonyl group, a 4-dimethylamino phenylsulfonyl group, and the like.

The alkyl group, the aryl group, the acyl group, the alkylsulfonyl group, and the arylsulfonyl group which are represented by $R^1$ may have a substituent group. Examples of the substituent group include a halogen atom (a fluorine atom, a chloro atom, a bromine atom, and an iodine atom), a straight-chain, branched, or cyclic alkyl group (for example, a methyl group, an ethyl group, a propyl group, and the like), an alkenyl group, an alkynyl group, an aryl group, an acyl group, an alkoxycarbonyl group, an aryloxycarbonyl group, a carbamoyl group, a cyano group, a carboxyl group, a hydroxyl group, an alkoxy group, an aryloxy group, an alkylthio group, an arylthio group, a heterocyclic oxy group, an acyloxy group, an amino group, a nitro group, a hydrazino group, a heterocyclic group, and the like. In addition, further substitution may be carried out using these groups. A halogen atom and a methyl group are preferable.

$R^1$ is preferably an aryl group, an acyl group, or an alkyl group.

Examples of the monovalent organic group represented by $Y_1$ and $Y_2$ include a hydrocarbon group, an alkyloxy group, an aryloxy group, an amino group which may have a substituent group, a heterocyclic group, and the like.

n1 and n2 denote an integer of 1 or more, preferably 1 to 8, more preferably 1 to 6, and even more preferably 1 to 3.

Examples of the hydrocarbon group include an alkyl group, a cycloalkyl group, an aryl group, and a group formed by combining two or more of these groups, and the specific examples and preferable examples of the alkyl group, the cycloalkyl group, and the aryl group are the same as for the alkyl group, the cycloalkyl group, and the aryl group denoted by $R^1$ described above.

The alkyloxy group may be straight-chain, or may be branched. Examples of the alkyloxy group include groups having 1 to 20 carbon atoms such as a methoxy group, an ethoxy group, an n-propoxy group, an i-propoxy group, an n-butoxy group, a 2-methylpropoxy group, a 1-methylpropoxy group, and a t-butoxy group.

The aryloxy group is preferably an aryloxy group having 6 to 30 carbon atoms, and examples thereof include a phenyloxy group, a 1-naphthyloxy group, a 2-naphthyloxy group, a 2-chlorophenyloxy group, a 2-methylphenyloxy group, a 2-methoxyphenyloxy group, a 2-butoxyphenyloxy group, a 3-chlorophenyloxy group, a 3-trifluoromethylphenyloxy group, a 3-cyanophenyloxy group, a 3-nitrophenyloxy group, a 4-fluorophenyloxy group, a 4-cyanophenyloxy group, a 4-methoxyphenyloxy group, a 4-dimethylaminophenyloxy group, a 4-methylsulfanylphenyloxy group, a 4-phenylsulfanylphenyloxy group, and the like.

As the amino group which may have a substituent group, an amino group having a total number of carbon atoms of 0 to 50 is preferable, and examples thereof include $-NH_2$, an N-alkylamino group, an N-arylamino group, an N-acylamino group, an N-sulfonylamino group, an N,N-dialkylamino group, an N,N-diarylamino group, a N-alkyl-N-arylamino group, an N,N-disulfonylamino group, and the like. More specifically, examples thereof include an N-methylamino group, an N-ethylamino group, an N-propylamino group, an N-isopropylamino group, an N-butylamino group, an N-tert-butylamino group, an N-hexylamino group, an N-cyclohexylamino group, an N-octylamino group, an N-2-ethylhexylamino group, an N-decylamino group, an N-octadecylamino group, an N-benzylamino group, an N-phenylamino group, an N-2-methylphenylamino group, an N-2-chlorophenylamino group, an N-2-methoxyphenylamino group, an N-2-isopropoxyphenylamino group, an N-2-(2-ethylhexyl) phenylamino group, an N-3-chlorophenylamino group, an N-3-nitrophenylamino group, an N-3-cyanophenylamino group, an N-3-trifluoromethylphenylamino group, an N-4-methoxyphenylamino group, an N-4-cyanophenylamino group, an N-4-trifluoromethyl phenylamino group, an N-4-methylsulfanylphenylamino group, an N-4-phenylsulfanylphenylamino group, an N-4-dimethylaminophenylamino group, an N-methyl-N-phenylamino group, an N,N-dimethylamino group, an N,N-diethylamino group, an N,N-dibutylamino group, an N,N-diphenylamino group, an N,N-diacetylamino group, an N,N-dibenzoylamino group, an N,N-(dibutyl carbonyl) amino group, an N,N-(dimethyl sulfonyl) amino group, an N,N-(diethyl sulfonyl) amino group, an N,N-(dibutyl sulfonyl) amino group, an N,N-(diphenyl sulfonyl) amino group, and the like.

The heterocyclic group may be, for example, monocyclic or may be polycyclic. Examples of such heterocyclic rings include an imidazole ring, a pyridine ring, a pyrazine ring, a pyrimidine ring, a pyridazine ring, a 2H-pyrrole ring, a 3H-indole ring, a 1H-indazole ring, a purine ring, an isoquinoline ring, a 4H-quinolizine ring, a quinoline ring, a phthalazine ring, a naphthyridine ring, a quinoxaline ring, a quinazoline ring, a cinnoline ring, a pteridine ring, a phenanthridine ring, an acridine ring, a phenanthroline ring, a phenazine ring, a perimidine ring, a triazine ring, a benzisoquinoline ring, a thiazole ring, a thiadiazine ring, an azepine ring, an azocine ring, an isothiazole ring, an isoxazole ring, and a benzothiazole ring. However, as long as the heterocyclic ring is a ring formed of carbon and hetero atoms, or a ring formed only of hetero atoms, the heterocyclic ring is not limited thereto.

The hydrocarbon group, the alkyloxy group, the aryloxy group, the heterocyclic group represented by $Y_1$ and $Y_2$ may have a substituent group, and examples of the substituent group include a halogen atom (a fluorine atom, a chloro atom, a bromine atom, and an iodine atom), a straight-chain, branched, or cyclic alkyl group (for example, a methyl group, an ethyl group, a propyl group, and the like), an alkenyl group, an alkynyl group, an aryl group, an acyl group, an alkoxycarbonyl group, an aryloxycarbonyl group, a carbamoyl group, a cyano group, a carboxyl group, a hydroxyl group, an alkoxy group, an aryloxy group, an alkylthio group, an arylthio group, a heterocyclic oxy group, an acyloxy group, an amino group, a nitro group, a hydrazino group, a heterocyclic group, and the like. In addition, further substitution may be carried out using these groups. The substituent group described above is preferably a halogen atom or a methyl group.

The hydrocarbon group represented by $Y_1$ and $Y_2$ may have an alicyclic hydrocarbon structure (preferably, a cyclopentane ring or a cyclohexane ring) having 5 or more carbon atoms, and the ring members forming the alicyclic hydrocarbon structure described above may include hetero atoms such as a keto group, an ether group, or a thioether group.

$Y_1$ and $Y_2$ are preferably a monovalent hydrocarbon group which has an alicyclic hydrocarbon structure having 5 or more carbon atoms, an alkyl group, a cycloalkyl group, an aryl group, or a heterocyclic group, more preferably a monovalent hydrocarbon group which has an alicyclic hydrocarbon structure having 5 or more carbon atoms, an alkyl group, a cycloalkyl group, or an aryl group, and even more preferably an aryl group or a monovalent hydrocarbon group which has an alicyclic hydrocarbon structure having 5 or more carbon atoms.

$R^1$ and $Y_1$ or $Y_2$ may bond with each other to form a ring and examples of the formed ring include a pyrrolidine ring and a piperidine ring.

Specific examples of the anion structure of the compound which is represented by General Formula (I) or (II) will be given below; however, the present invention is not limited thereto.

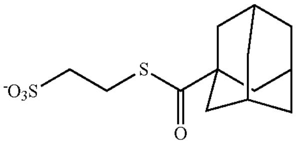

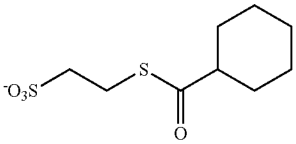

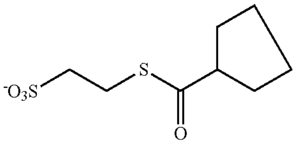

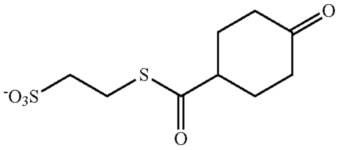

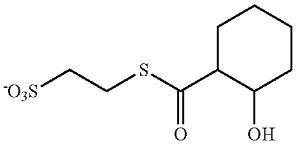

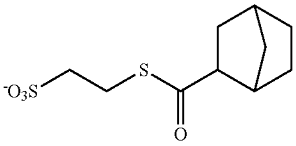

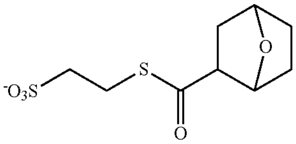

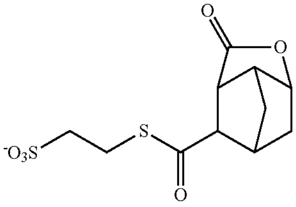

-continued

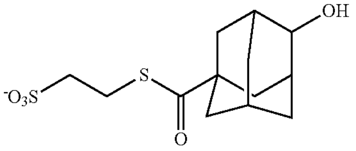

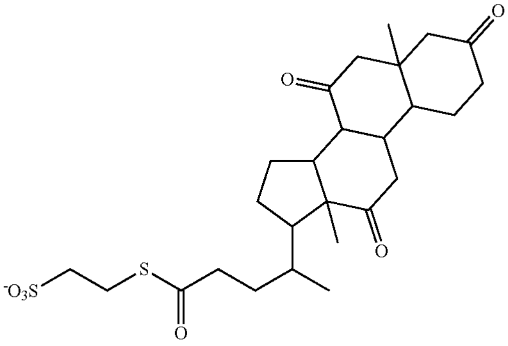

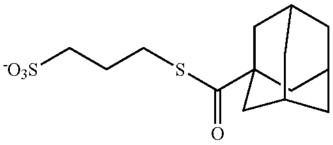

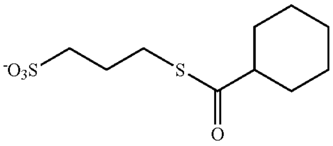

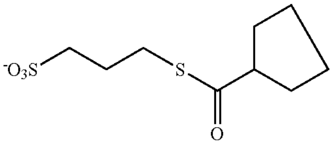

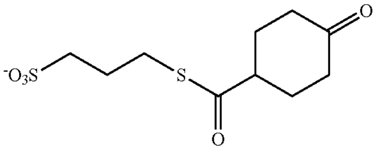

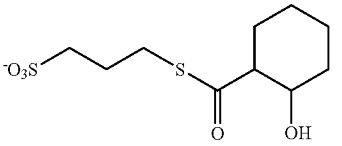

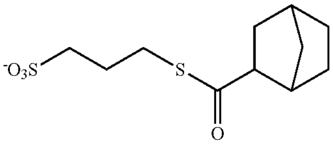

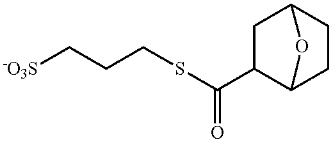

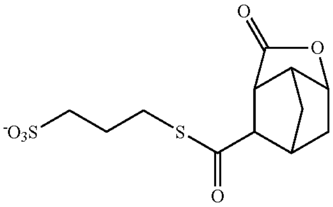

-continued
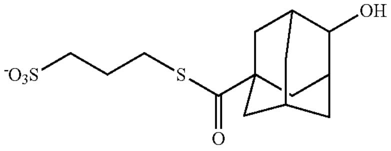
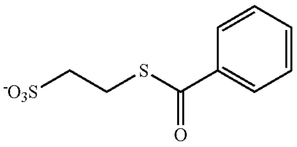
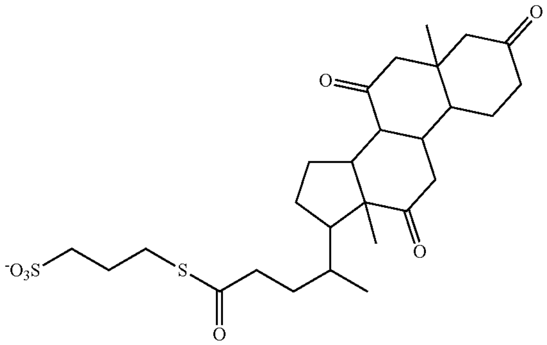
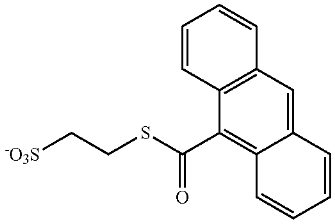
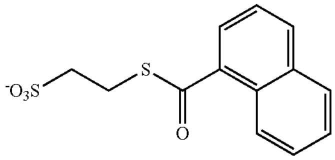
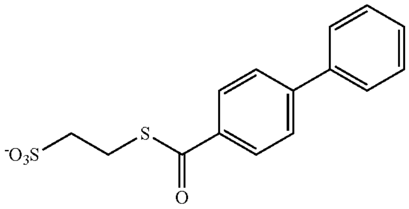
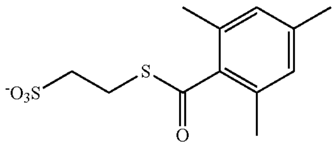
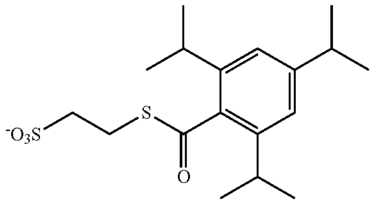
-continued
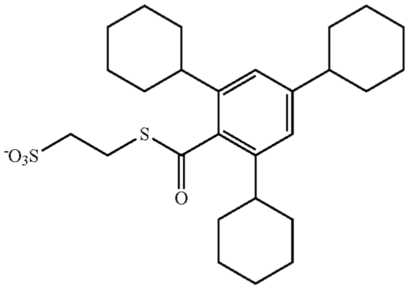
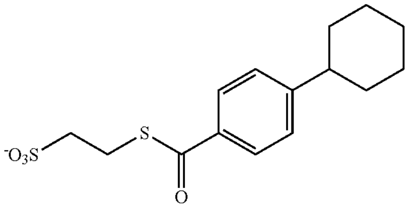
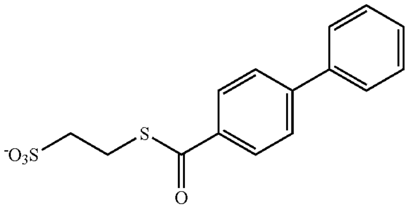
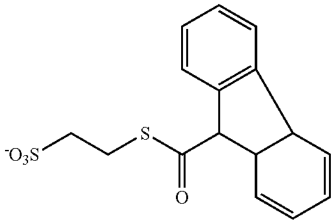
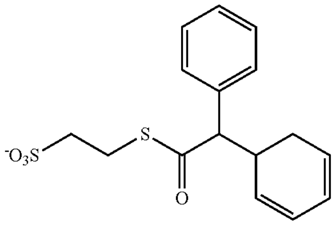
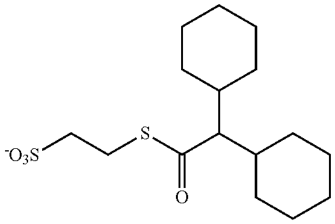
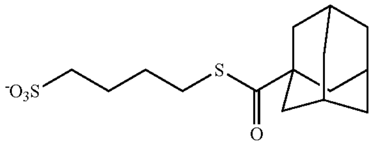
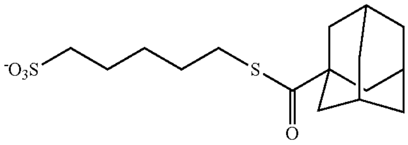

-continued
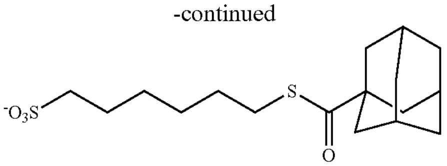
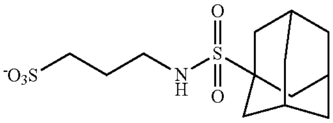
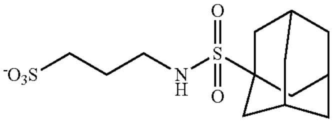
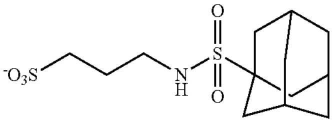
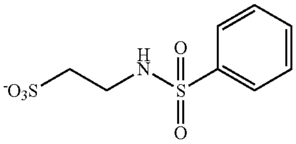
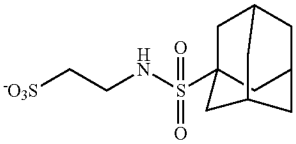
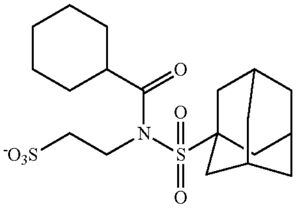
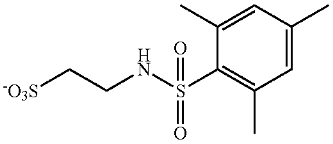
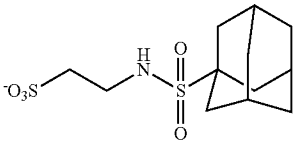
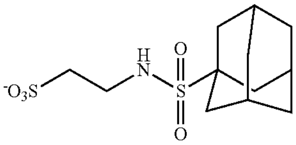
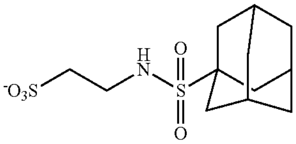
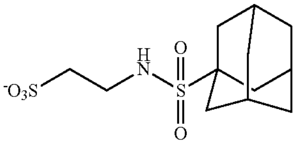
-continued
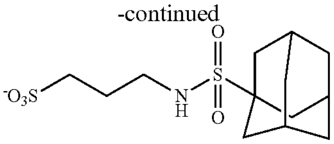
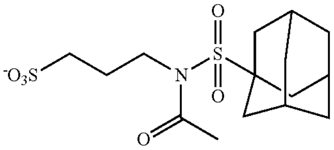
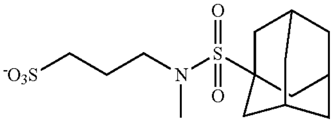
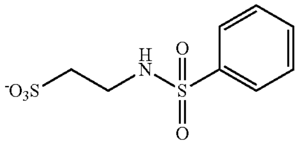
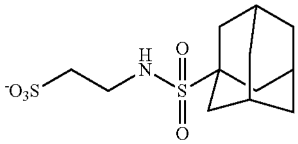
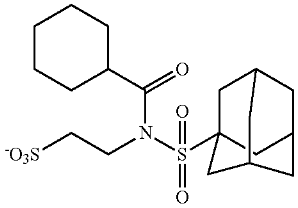
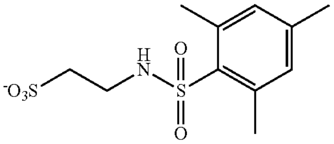
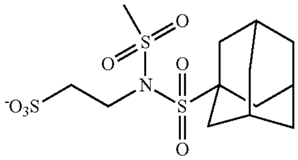
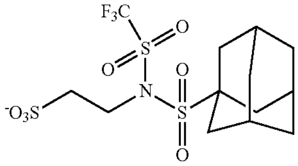
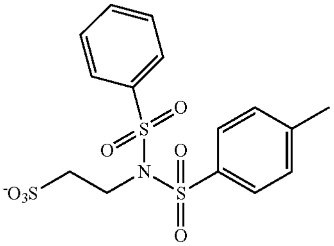
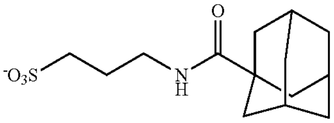

-continued
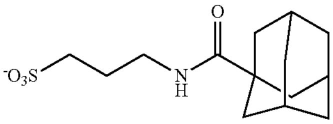
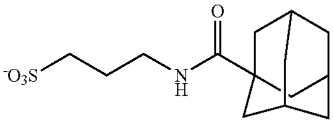
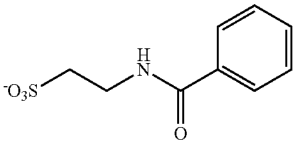
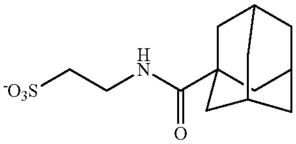
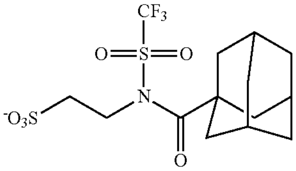
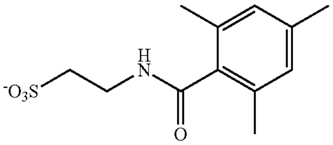
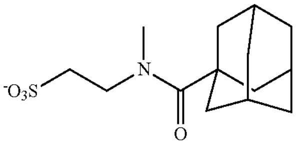
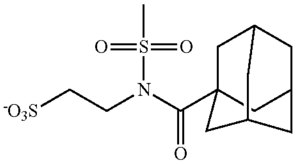
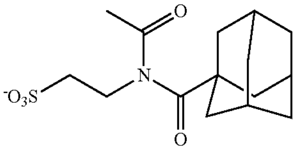
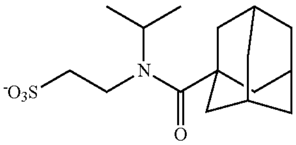
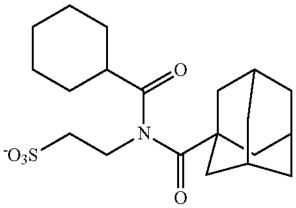
-continued
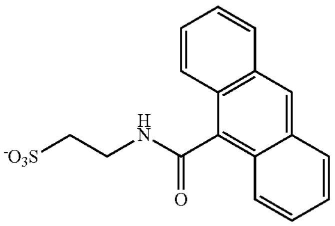
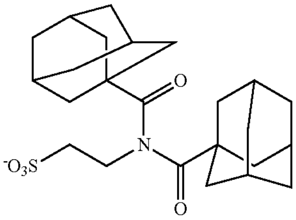
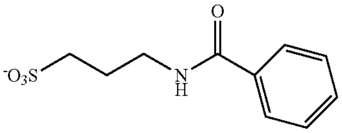
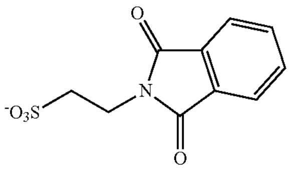
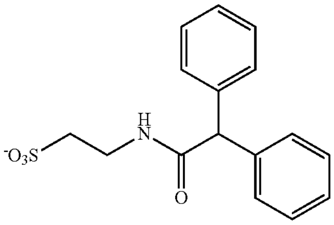
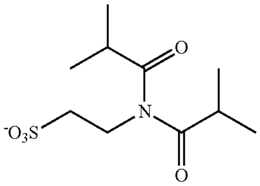
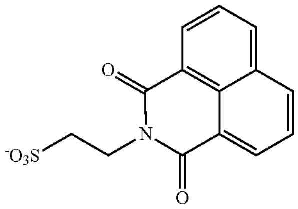
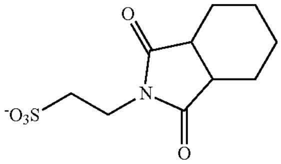
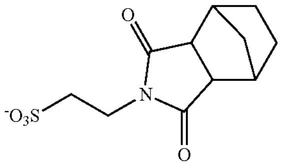

-continued
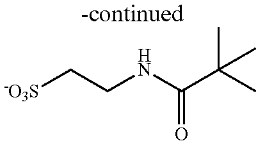
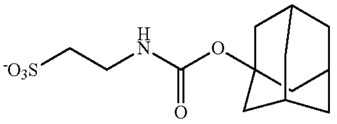
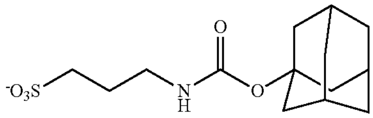
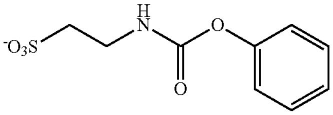
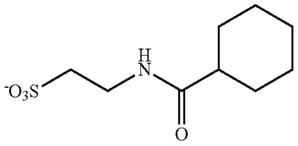
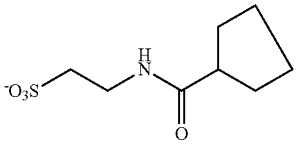
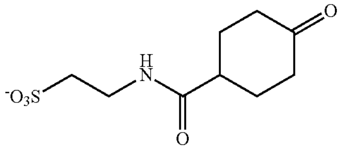
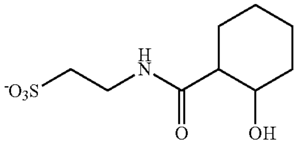
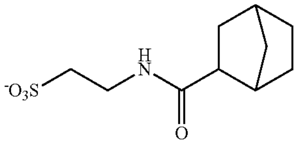
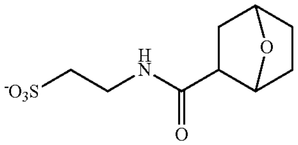
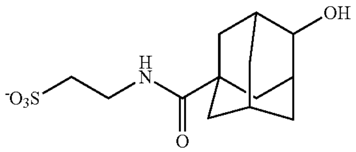
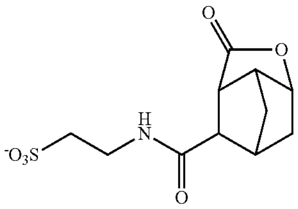
-continued
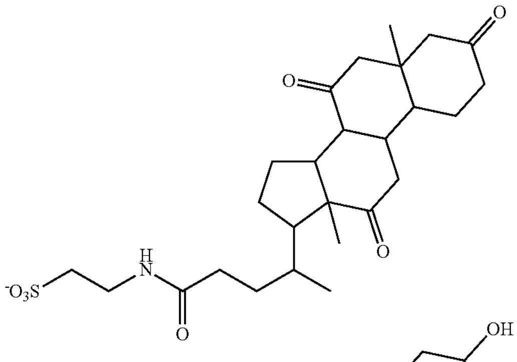
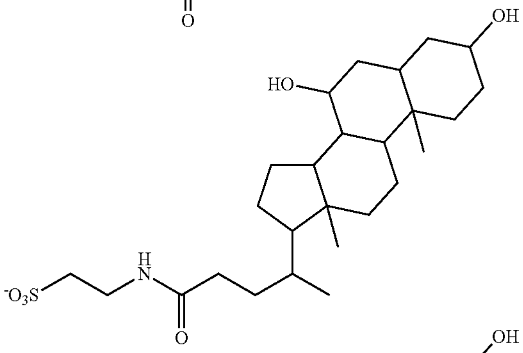
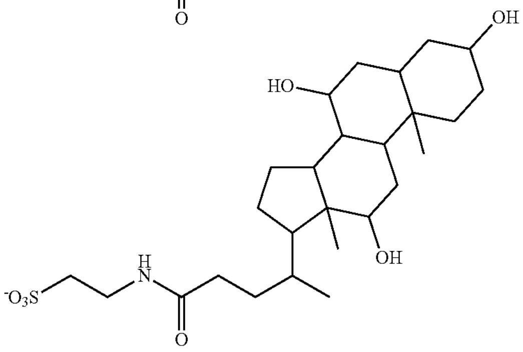
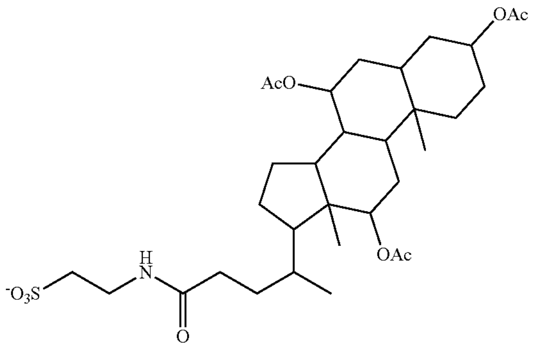
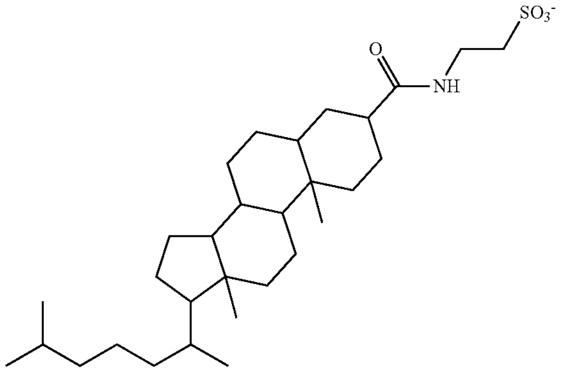

Examples of the organic onium ion (countercation) which is represented by $M_1^+$ and $M_2^+$ include onium ions such as iodonium, sulfonium, phosphonium, diazonium, ammonium, pyridinium, quinolinium, acridinium, oxonium, selenonium, and arsonium, among which onium ions such as iodonium, sulfonium, phosphonium, diazonium, quinolinium, and acridinium are preferable, and onium ions such as iodonium and sulfonium are even more preferable.

In addition, examples thereof include cations such as onium ions of onium salts of group 15 to 17 elements described in JP1994-184170A (JP-H06-184170A), and the like, diazonium ions of diazonium salts described in S. I. Schlesinger, Photogr. Sci. Eng., 18, 387 (1974), T. S. Bal et al., Polymer, 21, 423 (1980), and the like, ammonium ions of ammonium salts described in U.S. Pat. No. 4,069,055A, U.S. Pat. No. 4,069,056A, US RE27992E, JP1991-140140A (JP-H03-140140A), and the like, phosphonium ions of phosphonium salts described in D.C. Necker et al., Macromolecules, 17, 2468 (1984), C. S. Wen et al., Teh, Proc. Conf. Rad. Curing ASIA, p. 478 Tokyo, October (1988), U.S. Pat. No. 4,069,055A, U.S. Pat. No. 4,069,056A, JP1997-202873A (JP-H09-202873A), and the like, iodonium ions of iodonium salts described in J. V. Crivello et al., Macromolecules, 10 (6), 1307 (1977), Chem. & Eng. News, November 28, p. 31 (1988), EP104143B, EP339049B, EP410201B, JP1990-150848A (JP-H02-150848A), JP1990-296514A (JP-H02-296514A), and the like, sulfonium ions of sulfonium salts described in J. V. Crivello et al., Polymer J. 17, 73 (1985), J. V. Crivello et al., J. Org. Chem., 43, 3055 (1978), W. R. Watt et al., J. Polymer Sci., Polymer Chem. Ed., 22, 1789 (1984), J. V. Crivello et al., Polymer Bull., 14, 279 (1985), J. V. Crivello et al., Macromolecules, 14(5), 1141 (1981), J. V. Crivello et al., J. Polymer Sci., Polymer Chem. Ed., 17, 2877 (1979), EP370693B, EP161811B, EP410201B, EP339049B, EP233567B, EP297443B, EP297442B, U.S. Pat. No. 3,902,114A, U.S. Pat. No. 4,933,377A, U.S. Pat. No. 4,760,013A, U.S. Pat. No. 4,734,444A, U.S. Pat. No. 2,833,827A, DE2904626B, DE3604580B, DE3604581B, JP1995-28237A (JP-H07-28237A), JP1996-27102A (JP-H08-27102A), and the like, quinolinium ions of quinolinium salts described in JP1997-221652A (JP-H09-221652A) and the like, selenonium ions of selenonium salts described in J. V. Crivello et al., Macromolecules, 10 (6), 1307 (1977), J. V. Crivello et al., J. Polymer Sci., Polymer Chem. Ed., 17, 1047 (1979), and the like, and arsonium ions of arsonium salts described in C. S. Wen et al., Teh, Proc. Conf. Rad. Curing ASIA, p. 478 Tokyo, October (1988), and the like; however, the present invention is not limited thereto.

In addition, preferable examples of the countercation described above include cations having the structure represented by any one of Formulae (II) to (VII) below.

(II)

$$R^1—N^+≡N$$

(III)

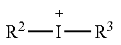

(IV)

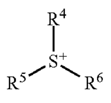

(V)

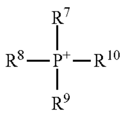

-continued (VI)

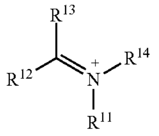

(VII)

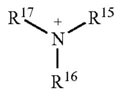

In Formulae (II) to (VII) above, $R^1$ to $R^3$ each independently represent an aryl group, $R^4$ to $R^6$ each independently represent an alkyl group, an alkenyl group, an alkynyl group, an aryl group, a cyclic hydrocarbon group, or a heterocyclic group, $R^7$ to $R^{11}$ each independently represent an alkyl group, an alkenyl group, an alkynyl group, an aryl group, a cyclic hydrocarbon group, a heterocyclic group, an alkoxy group, or an aryloxy group, and $R^{12}$ to $R^{17}$ each independently represent a hydrogen atom, a halogen atom, or a monovalent organic group.

The alkyl groups denoted by $R^4$ to $R^{11}$ preferably have 1 to 30 carbon atoms, more preferably 1 to 20 carbon atoms, and particularly preferably 1 to 8 carbon atoms, and may be straight-chain and may have a substituent group.

The alkenyl groups denoted by $R^4$ to $R^{11}$ preferably have 2 to 30 carbon atoms, more preferably 2 to 20 carbon atoms, and particularly preferably 2 to 8 carbon atoms, and may further have a substituent group.

The alkynyl groups denoted by $R^4$ to $R^{11}$ preferably have 2 to 30 carbon atoms, more preferably 2 to 20 carbon atoms, and particularly preferably 2 to 8 carbon atoms, and may further have a substituent group.

The aryl groups denoted by $R^1$ to $R^{11}$ preferably have 6 to 30 carbon atoms, more preferably 6 to 20 carbon atoms, and particularly preferably 6 to 10 carbon atoms, and may further have a substituent group.

The cyclic hydrocarbon groups denoted by $R^4$ to $R^{11}$ preferably have 3 to 30 carbon atoms, more preferably 3 to 20 carbon atoms, and particularly preferably 3 to 10 carbon atoms, and may further have a substituent group.

The heterocyclic groups denoted by $R^4$ to $R^{11}$ preferably have 4 to 30 carbon atoms, more preferably 4 to 20 carbon atoms, and particularly preferably 4 to 10 carbon atoms, and may further have a substituent group. In addition, the hetero atom included in the heterocyclic group is preferably a nitrogen atom, an oxygen atom, or a sulfur atom.

The alkoxy groups denoted by $R^7$ to $R^{11}$ preferably have 1 to 30 carbon atoms, more preferably 1 to 20 carbon atoms, and even more preferably 1 to 8 carbon atoms. In addition, the alkoxy groups may have a substituent group described below, and the alkyl moiety of the alkoxy groups may be an alkenyl group, an alkynyl group, a cyclic hydrocarbon group, or a heterocyclic group other than an aromatic group.

The aryloxy groups denoted by $R^7$ to $R^{11}$ preferably have 6 to 30 carbon atoms, more preferably 6 to 20 carbon atoms, and even more preferably 6 to 10 carbon atoms. In addition, the aryloxy groups may have a substituent group described below, and the aryl moiety of the aryloxy groups may be an aromatic heterocyclic group.

In Formula (III), $R^2$ and $R^3$ may be bonded with each other to form a ring if this is possible.

In Formula (IV), two or more of $R^4$ to $R^6$ may be bonded with each other to form a ring if this is possible.

In Formula (V), two or more of $R^7$ to $R^{10}$ may be bonded with each other to form a ring if this is possible.

In Formula (VI), two or more of $R^{11}$ to $R^{14}$ may be bonded with each other to form a ring if this is possible.

In Formula (VII), two or more of $R^{15}$ to $R^{17}$ may be bonded with each other to form a ring if this is possible.

With regard to substituent groups which the alkyl group, the alkenyl group, the alkynyl group, the aryl group, the hydrocarbon group, the heterocyclic group, the alkoxy group, or the aryloxy group may have, a monovalent non-metallic atomic group other than hydrogen is used, and preferable examples thereof include a halogen atom (—F, —Br, —Cl, —I), a hydroxyl group, an alkyl group, an aryl group, an alkenyl group, an alkynyl group, an alkoxy group, an aryloxy group, a mercapto group, an alkylthio group, an arylthio group, an alkyldithio group, an aryldithio group, an amino group, an N-alkylamino group, an N,N-dialkylamino group, an N-arylamino group, an N,N-diarylamino group, an N-alkyl-N-arylamino group, an acyloxy group, a carbamoyloxy group, an N-alkylcarbamoyloxy group, an N-arylcarbamoyloxy group, an N,N-dialkylcarbamoyloxy group, an N,N-diarylcarbamoyloxy group, an N-alkyl-N-arylcarbamoyloxy group, an alkylsulfoxy group, an arylsulfoxy group, an acylthio group, an acylamino group, an N-alkylacylamino group, an N-arylacylamino group, a ureido group, an N'-alkylureido group, an N',N'-dialkylureido group, an N'-arylureido group, an N',N'-diarylureido group, an N'-alkyl-N'-arylureido group, an N-alkylureido group, an N-arylureido group, an N'-alkyl-N-alkylureido group, an N'-alkyl-N-arylureido group, an N',N'-dialkyl-N-alkylureido group, an N',N'-dialkyl-N-arylureido group, an N'-aryl-N-alkylureido group, an N'-aryl-N-arylureido group, an N',N'-diaryl-N-alkylureido group, an N',N'-diaryl-N-arylureido group, an N'-alkyl-N'-aryl-N-alkylureido group, an N'-alkyl-N'-aryl-N-arylureido group, an alkoxycarbonylamino group, an aryloxycarbonylamino group, an N-alkyl-N-alkoxycarbonylamino group, an N-alkyl-N-aryloxycarbonylamino group, an N-aryl-N-alkoxycarbonylamino group, an N-aryl-N-aryloxycarbonylamino group, a formyl group, an acyl group, a carboxyl group and conjugate base groups thereof (referred to below as carboxylate group), an alkoxycarbonyl group, an aryloxycarbonyl group, a carbamoyl group, an N-alkylcarbamoyl group, an N,N-dialkylcarbamoyl group, an N-arylcarbamoyl group, an N,N-diarylcarbamoyl group, an N-alkyl-N-arylcarbamoyl group, an alkylsulfinyl group, an arylsulfinyl group, an alkylsulfonyl group, an arylsulfonyl group, a sulfo group (—$SO_3H$) and conjugate base groups thereof (referred to below as sulfonate groups), an alkoxysulfonyl group, an aryloxysulfonyl group, a sulfinamoyl group, an N-alkylsulfinamoyl group, an N,N-dialkylsulfinamoyl group, an N-arylsulfinamoyl group, an N,N-diarylsulfinamoyl group, an N-alkyl-N-arylsulfinamoyl group, a sulfamoyl group, an N-alkylsulfamoyl group, an N,N-dialkylsulfamoyl group, an N-arylsulfamoyl group, an N,N-diarylsulfamoyl group, an N-alkyl-N-arylsulfamoyl group, an N-acylsulfamoyl group and conjugate base groups thereof, an N-alkylsulfonylsulfamoyl group (—$SO_2NHSO_2$(alkyl)) and conjugate base groups thereof, an N-arylsulfonylsulfamoyl group (—$SO_2NHSO_2$(allyl)) and conjugate base groups thereof, an N-alkylsulfonylcarbamoyl group (—$CONHSO_2$(alkyl)) and conjugate base groups thereof, an N-arylsulfonylcarbamoyl group (—$CONHSO_2$(allyl)) and conjugate base groups thereof, a silyl group, an alkoxysilyl group (—Si(O-alkyl)$_3$), an aryloxysilyl group (—Si(O-allyl)$_3$), a hydroxysilyl group (—$Si(OH)_3$) and conjugate base groups thereof, a phosphono group (—$PO_3H_2$) and conjugate base groups thereof (referred to below as phosphonate groups), a dialkylphosphono group (—$PO_3$(alkyl)$_2$), a diarylphosphono group (—$PO_3$(aryl)$_2$), an alkylarylphosphono group (—$PO_3$(alkyl)(aryl)), a monoalkylphosphono group (—$PO_3H$(alkyl)) and conjugate base groups thereof (referred to below as alkylphosphonate groups), a monoarylphosphono group (—$PO_3H$(aryl)) and conjugate base groups thereof (referred to below as arylphosphonate groups), a phosphonooxy group (—$OPO_3H_2$) and conjugate base groups thereof (referred to below as phosphonatooxy groups), a dialkylphosphonooxy group (—$OPO_3$(alkyl)$_2$), a diarylphosphonooxy group (—$OPO_3$(aryl)$_2$), an alkylarylphosphonooxy group (—$OPO_3$(alkyl)(aryl)), a monoalkylphosphonooxy group (—$OPO_3H$(alkyl)) and conjugate base groups thereof (referred to below as alkylphosphonatooxy groups), a monoarylphosphonooxy group (—$OPO_3H$(aryl)) and conjugate base groups thereof (referred to below as arylphosphonatooxy groups), a cyano group, and a nitro group. These substituent groups may be further substituted with the substituent group described above, and may form a ring if this is possible.

$R^{12}$ to $R^{17}$ each independently represent a hydrogen atom, a halogen atom, or a monovalent organic group.

Examples of the halogen atom denoted by $R^{12}$ to $R^{17}$ include a fluorine atom, a chlorine atom, a bromine atom, and an iodine atom, and a fluorine atom, a chlorine atom, or a bromine atom is preferable.

Examples of the monovalent organic group denoted by $R^{12}$ to $R^{17}$ include a hydroxyl group, an alkyl group, an alkenyl group, an alkynyl group, an aryl group, a cyclic hydrocarbon group, a heterocyclic group, an alkoxy group, an aryloxy group, an acyl group, an alkoxycarbonyl group, an acyloxy group, —$SO_3$—$R^a$, —$NR^bR^c$, a cyano group, —$SiR^dR^eR^f$, —$SOR^g$, —$SO_2R^g$, and a nitro group; R represents a hydrogen atom, an alkyl group, an alkenyl group, an alkynyl group, an aryl group, an arylalkyl group, an alkali metal atom, or quaternary ammonium; $R^b$, $R^c$, and $R^g$ each independently represent an alkyl group, an alkenyl group, an alkynyl group, an aryl group, a cyclic hydrocarbon group, or a heterocyclic group; and $R^d$ to $R^f$ each independently represent an alkyl group, an alkenyl group, an alkynyl group, an aryl group, a cyclic hydrocarbon group, a heterocyclic group, an alkoxy group, or an aryloxy group.

The alkyl group, alkenyl group, alkynyl group, aryl group, cyclic hydrocarbon group, heterocyclic group, alkoxy group, and aryloxy group in $R^{12}$ to $R^{17}$ have the same meanings as those represented by $R^7$ to $R^{11}$ above, and the preferable ranges thereof are also the same. In addition, these groups may have the substituent groups above.

The acyl group and the alkoxycarbonyl group in $R^{12}$ to $R^{17}$ preferably each have 1 to 30 carbon atoms in the carbon chain side thereof, and particularly preferably 1 to 12, and may be a straight-chain and may have the substituent groups above.

The acyloxy group in $R^{12}$ to $R^{17}$ preferably has 1 to 30 carbon atoms, and particularly preferably 1 to 12 carbon atoms, and may be straight-chain and may have the substituent groups above.

$R^a$ in —$SO_3$—$R^a$ in $R^{12}$ to $R^{17}$ is preferably a hydrogen atom, the alkyl group which may have a substituent group, the aryl group which may have a substituent, a lithium atom, a sodium atom, or a potassium atom.

The alkyl group, alkenyl group, alkynyl group, aryl group, cyclic hydrocarbon group, and heterocyclic group in $R^b$ and $R^c$ in —$NR^bR^c$ have the same meanings as those represented by $R^7$ to $R^{11}$ above, and the preferable ranges thereof are also the same. Furthermore, these groups may have the substituent groups above.

The alkyl group, alkenyl group, alkynyl group, aryl group, cyclic hydrocarbon group, heterocyclic group, alkoxy group, and aryloxy group in $R^d$ to $R^f$ in —$SiR^dR^eR^f$ have the same meanings as those represented by $R^7$ to $R^{11}$ above, and the preferable ranges thereof are also the same. Furthermore, these groups may have the substituent groups above.

The alkyl group, alkenyl group, alkynyl group, aryl group, cyclic hydrocarbon group, and heterocyclic group in $R^g$ in —$SOR^g$ or —$SO_2R^g$ have the same meanings as those represented by $R^7$ to $R^{11}$ above, and the preferable ranges thereof are also the same. Furthermore, these groups may have the substituent groups above.

Specific examples of the countercations represented by General Formulae (II) to (VII) above preferably include countercations having the structures denoted by Ca-1 to Ca-46 below.

Ca-1

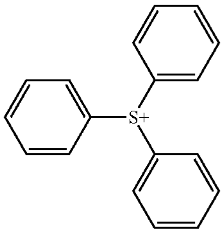

Ca-2

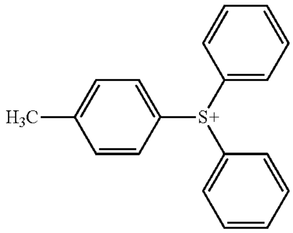

Ca-3

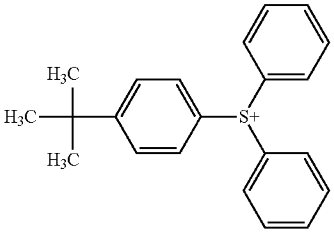

Ca-4

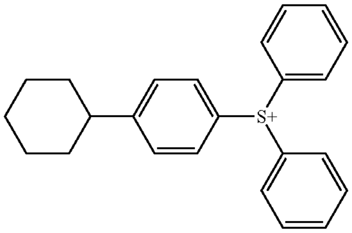

Ca-5

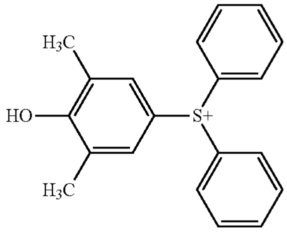

-continued

Ca-6

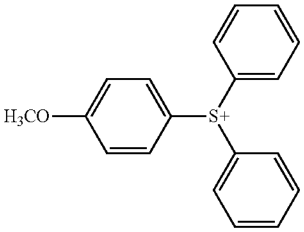

Ca-7

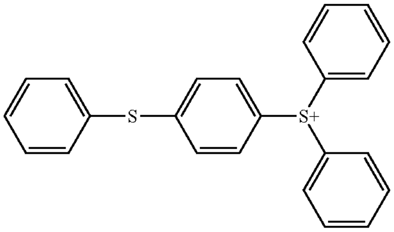

Ca-8

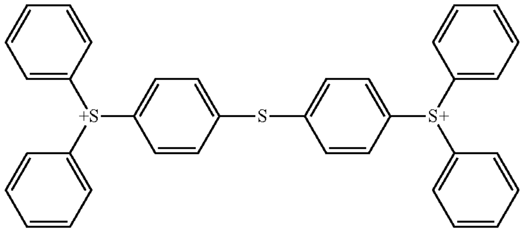

Ca-9

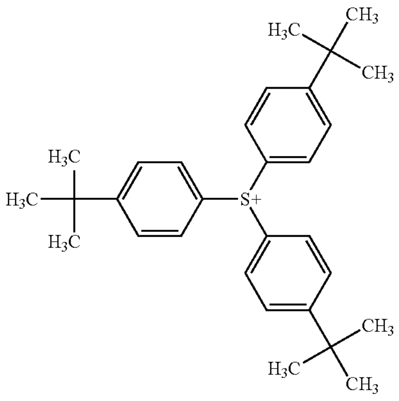

Ca-10

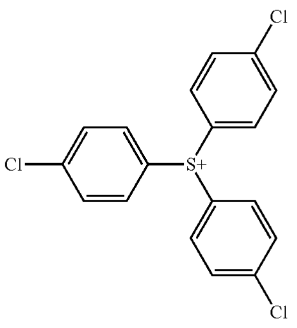

-continued
Ca-11
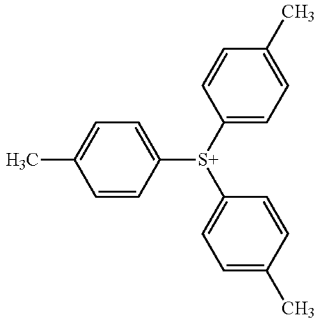
Ca-12
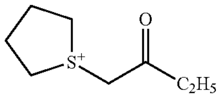
Ca-13
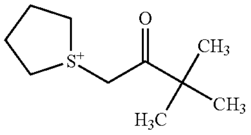
Ca-14
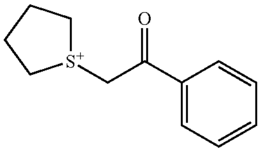
Ca-15
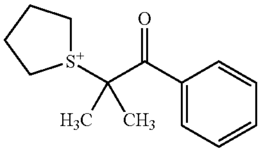
Ca-16
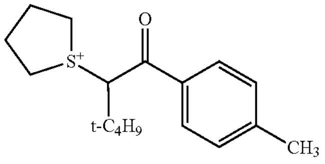
Ca-17
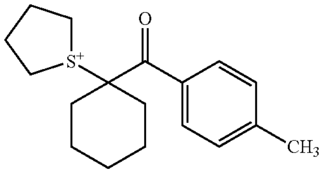
Ca-18
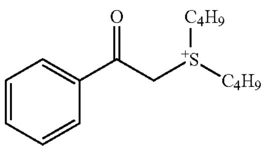
Ca-19
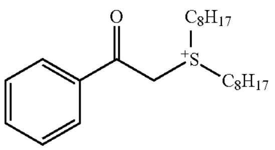
-continued
Ca-20
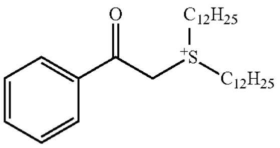
Ca-21
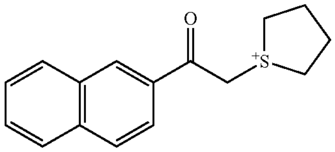
Ca-22
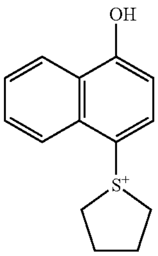
Ca-23
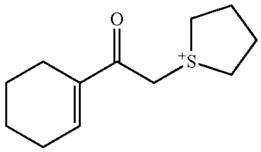
Ca-24
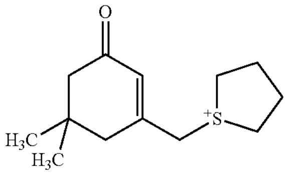
Ca-25
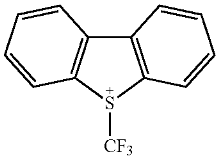
Ca-26
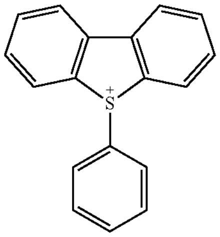
Ca-27
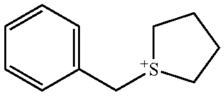
Ca-28
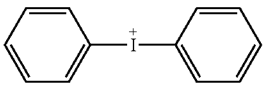

-continued
Ca-29
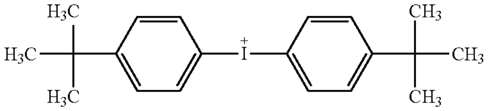
Ca-30
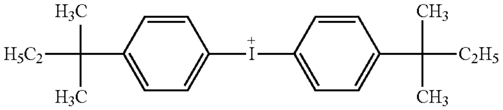
Ca-31
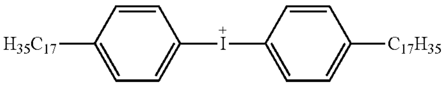
Ca-32
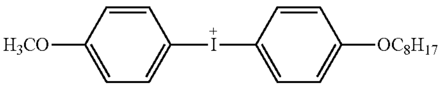
Ca-33
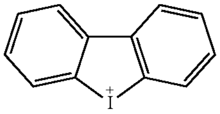
Ca-34
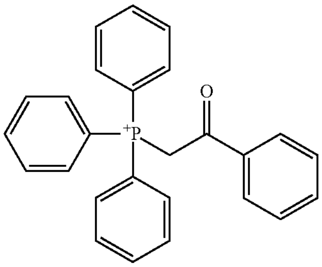
Ca-35
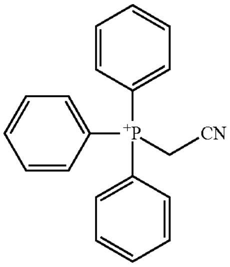
Ca-36
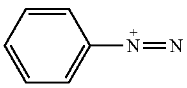
Ca-37
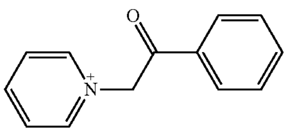
Ca-38
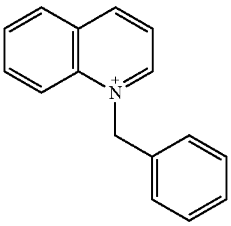
-continued
Ca-39
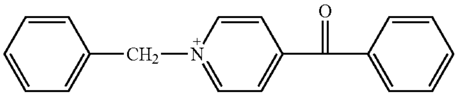
Ca-40
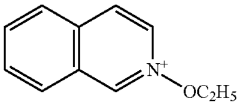
Ca-41
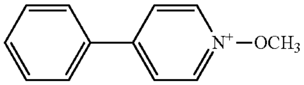
Ca-42
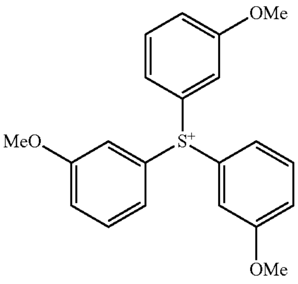
Ca-43
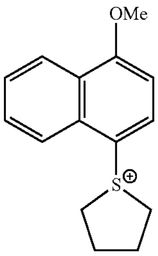
Ca-44
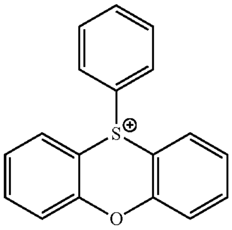
Ca-45
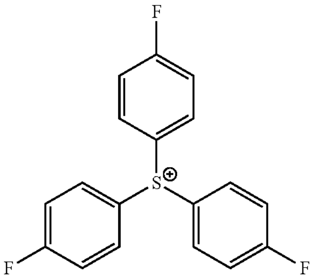

-continued

Ca-46

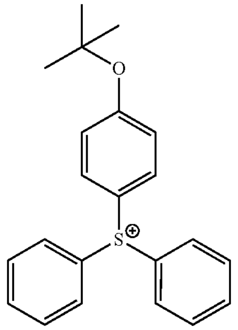

In addition, from the point of view of suppressing outgassing, examples of preferable organic onium ions include cations which have the structure of General Formula (VIII) below.

(VIII)

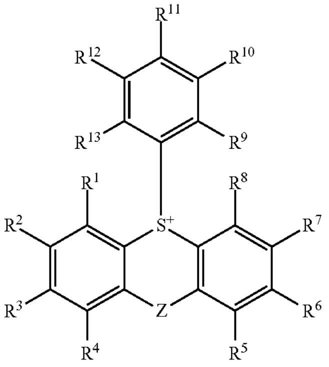

In General Formula (VIII), $R^1$ to $R^{13}$ each independently represent a hydrogen atom or a substituent group and at least one of $R^1$ to $R^{13}$ is a substituent group which includes an alcoholic hydroxyl group.

Z is a single bond or a divalent linking group.

The alcoholic hydroxyl group in the present invention represents a hydroxyl group which is bonded with a carbon atom of the alkyl group.

In a case where $R^1$ to $R^{13}$ are substituent groups which include an alcoholic hydroxyl group, $R^1$ to $R^{13}$ are preferably a group represented by —W—Y. Here, Y is an alkyl group which is substituted with a hydroxyl group and W is a single bond or a divalent linking group.

Examples of the alkyl group denoted by Y include a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group, a bornyl group, or the like. Preferable examples thereof include an ethyl group, a propyl group, an isopropyl group, an n-butyl group, an isobutyl group, and a sec-butyl group, and even more preferable examples thereof include an ethyl group, a propyl group, and an isopropyl group. Y particularly preferably has a $—CH_2CH_2OH$ structure.

The divalent linking group represented by W is not particularly limited; however, examples thereof include divalent groups in which an arbitrary hydrogen atom is substituted with a single bond in a monovalent group such as an alkoxy group, an acyloxy group, a carbamoyloxy group, an alkoxycarbonyloxy group, an aryloxycarbonyloxy group, an acylamino group, an aminocarbonylamino group, an alkoxycarbonylamino group, an aryloxy carbonylamino group, a sulfamoylamino group, an alkyl- or arylsulfonylamino group, an alkylthio group, an arylthio group, a sulfamoyl group, an alkyl- or arylsulfinyl group, an alkyl- or arylsulfonyl group, an acyl group, an aryloxycarbonyl group, an alkoxycarbonyl group, or a carbamoyl group.

W is preferably a single bond or a divalent group in which an arbitrary hydrogen atom is substituted with a single bond, an alkoxy group, an acyloxy group, an acylamino group, an alkyl- or arylsulfonylamino group, an alkylthio group, an alkylsulfonyl group, an acyl group, an alkoxycarbonyl group, or a carbamoyl group, and even more preferably a single bond or a divalent group in which an arbitrary hydrogen atom is substituted with a single bond, an acyloxy group, an alkylsulfonyl group, an acyl group, or an alkoxycarbonyl group.

In a case where $R^1$ to $R^{13}$ are substituent groups which include an alcoholic hydroxyl group, the number of carbon atoms in the substituent group is preferably 2 to 10, even more preferably 2 to 6, and particularly preferably 2 to 4.

The substituent group which includes an alcoholic hydroxyl group, as $R^1$ to $R^{13}$, may have two or more alcoholic hydroxyl groups.

The number of the alcoholic hydroxyl groups in the substituent group which includes the alcoholic hydroxyl groups, as $R^1$ to $R^{13}$, is 1 to 6, preferably 1 to 3, and even more preferably 1.

The number of alcoholic hydroxyl groups in $R^1$ to $R^{13}$ of the compound represented by General Formula (VIII) is 1 to 10, preferably 1 to 6, and even more preferably 1 to 3.

In a case where $R^1$ to $R^{13}$ do not contain an alcoholic hydroxyl group, $R^1$ to $R^{13}$ are each independently a hydrogen atom or a substituent group, and any group may be used as the substituent group without being particularly limited; however, examples thereof include a halogen atom, an alkyl group (including a cycloalkyl group, a bicycloalkyl group, and a tricycloalkyl group), an alkenyl group (including a cycloalkenyl group and a bicycloalkenyl group), an alkynyl group, an aryl group, a heterocyclic group (which may be referred to as a heterocyclic group), a cyano group, a nitro group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxy carbonylamino group, a sulfamoylamino group, an alkyl- or arylsulfonylamino group, a mercapto group, an alkylthio group, an arylthio group, a heterocyclic thio group, a sulfamoyl group, a sulfo group, an alkyl- or arylsulfinyl group, an alkyl- or arylsulfonyl group, an acyl group, an aryloxycarbonyl group, an alkoxycarbonyl group, a carbamoyl group, an aryl- or heterocyclic azo group, an imido group, a phosphino group, phosphinyl group, phosphinyloxy group, phosphinylamino group, a phosphono group, a silyl group, a hydrazino group, a ureido group, a boronic acid group (—$B(OH)_2$), a phosphato group (—$OPO(OH)_2$), a sulfato group (—$OSO_3H$), and other known substituent groups thereof.

In addition, it is also possible to form a ring (an aromatic or a non-aromatic hydrocarbon ring, or a heterocyclic ring; it is possible to form a polycyclic condensed ring by further combining them; and examples thereof include a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiin ring, a phenothiazine ring, and a phenazine ring) by bonding two adjacent groups of $R^1$ to $R^{13}$.

In a case where $R^1$ to $R^{13}$ do not contain an alcoholic hydroxyl group, $R^1$ to $R^{13}$ are preferably a hydrogen atom or a halogen atom, an alkyl group (including a cycloalkyl group, a bicycloalkyl group, and a tricycloalkyl group), an alkenyl group (including a cycloalkenyl groups and a bicycloalkenyl group), an alkynyl group, an aryl group, a cyano group, a carboxyl group, an alkoxy group, an aryloxy group, an acyloxy group, a carbamoyloxy group, an acylamino group, an aminocarbonylamino group, an alkoxycarbonylamino group, an aryloxycarbonylamino group, a sulfamoylamino group, an alkyl- or arylsulfonylamino group, an alkylthio group, an arylthio group, a sulfamoyl group, an alkyl- or arylsulfonyl group, an aryloxycarbonyl group, an alkoxycarbonyl group, a carbamoyl group, an imido group, a silyl group, or a ureido group.

In a case where $R^1$ to $R^{13}$ do not contain an alcoholic hydroxyl group, $R^1$ to $R^{13}$ are even more preferably a hydrogen atom or a halogen atom, an alkyl group (including a cycloalkyl group, a bicycloalkyl group, and a tricycloalkyl group), a cyano group, an alkoxy group, an acyloxy group, an acylamino group, an aminocarbonylamino group, an alkoxycarbonylamino group, an alkyl- or arylsulfonylamino group, an alkylthio group, a sulfamoyl group, an alkyl- or arylsulfonyl group, an alkoxycarbonyl group, or a carbamoyl group.

Furthermore, in a case where $R^1$ to $R^{13}$ do not contain an alcoholic hydroxyl group, $R^1$ to $R^{13}$ are particularly preferably a hydrogen atom or an alkyl group (including a cycloalkyl group, a bicycloalkyl group, and a tricycloalkyl group), a halogen atom, or an alkoxy group.

In General Formula (VIII), at least one of $R^1$ to $R^{13}$ preferably includes an alcoholic hydroxyl group, and at least one of $R^9$ to $R^{13}$ more preferably includes an alcoholic hydroxyl group.

Z represents a single bond or a divalent linking group and examples of the divalent linking group include an alkylene group, an arylene group, a carbonyl group, a sulfonyl group, a carbonyloxy group, a carbonylamino group, sulfonyl amide group, an ether group, a thioether group, an amino group, a disulfide group, an acyl group, an alkylsulfonyl group, —CH═CH—, —C≡C—, an aminocarbonylamino group, an aminosulfonylamino group, or the like, and may have a substituent group. These substituent groups are the same as the substituent groups indicated for $R^1$ to $R^{13}$ above. Z is preferably a single bond, a substituent group which does not have electron-withdrawing properties such as an alkylene group, an arylene group, an ether group, a thioether group, an amino group, —CH═CH—, an amino-carbonylamino group, or an amino sulfonylamino group, even more preferably a single bond, an ether group, or a thioether group, and particularly preferably a single bond.

Specific examples are given below of onium ions represented by General Formula (VIII); however, the present invention is not limited thereto.

(A1)

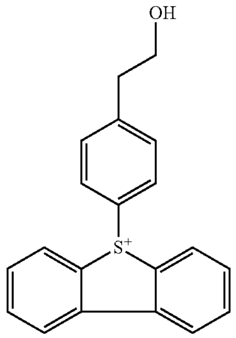

(A2)

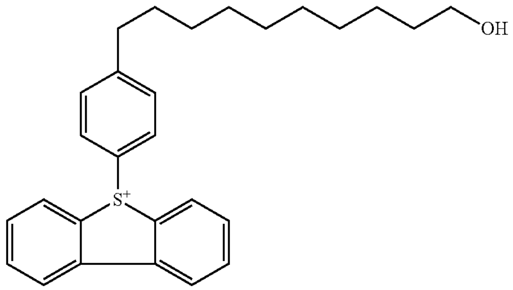

(A3)

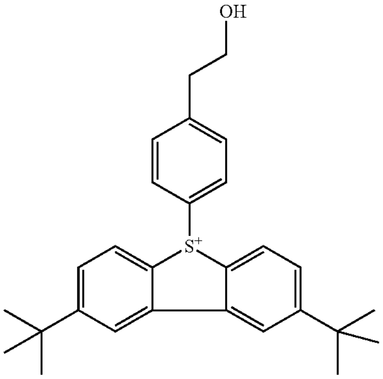

(A4)

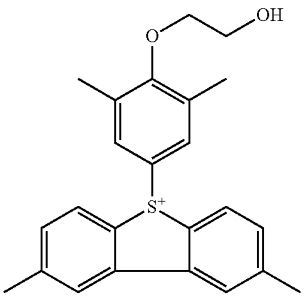

-continued
(A5)
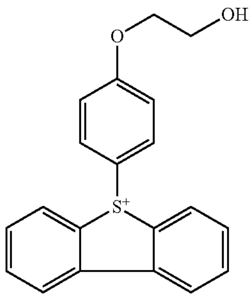
(A6)
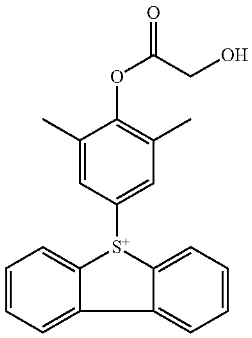
(A7)
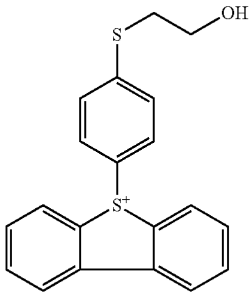
(A8)
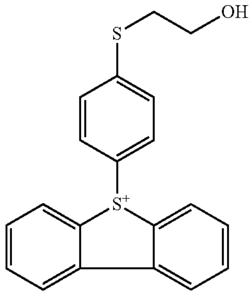
(A9)
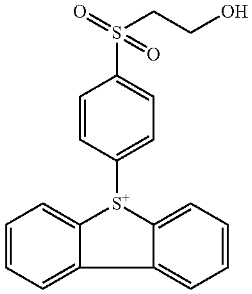
-continued
(A10)
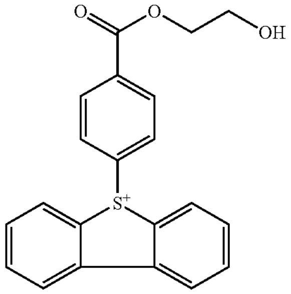
(A11)
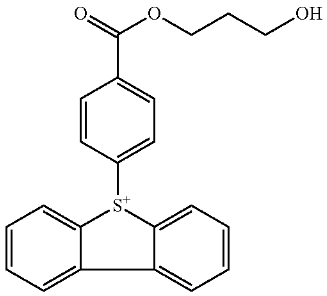
(A12)
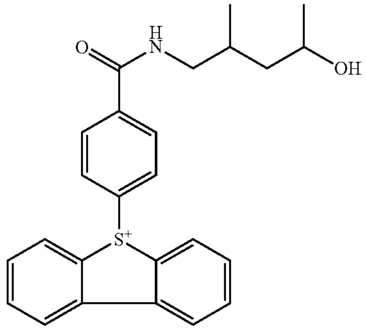
(A13)
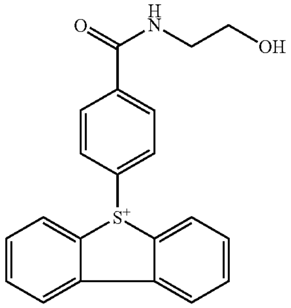
(A14)
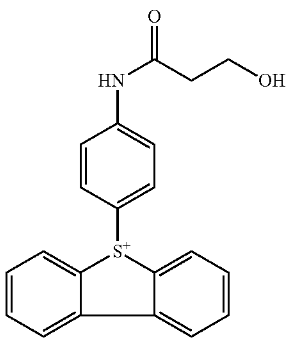

-continued
(A15)
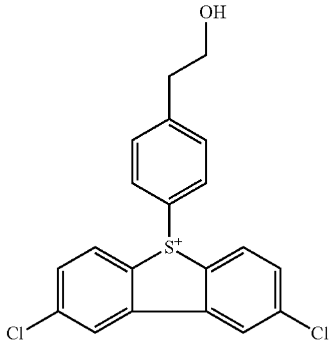
(A16)
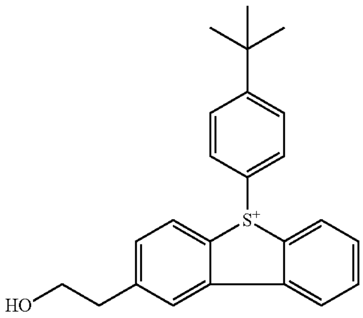
(A17)
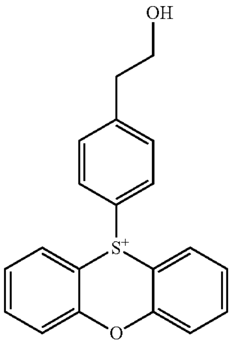
(A18)
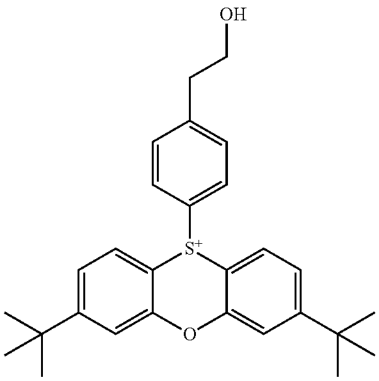
-continued
(A19)
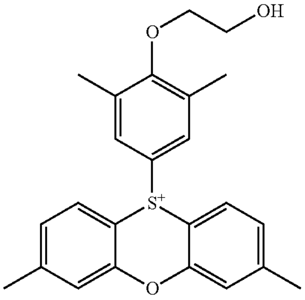
(A20)
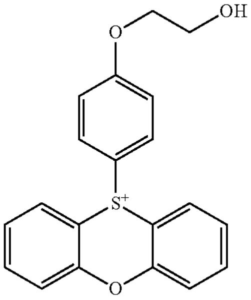
(A21)
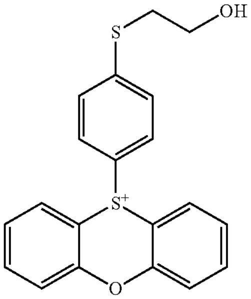
(A22)
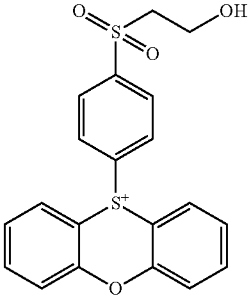
(A23)
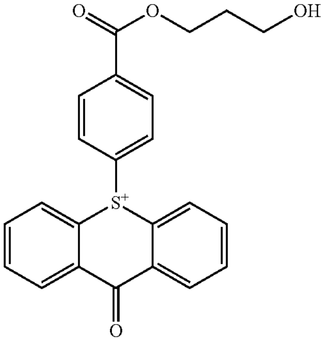

-continued (A24)

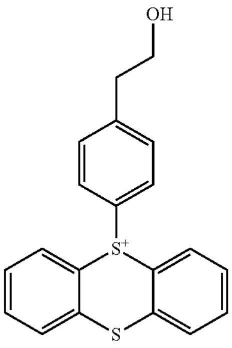

(A25)

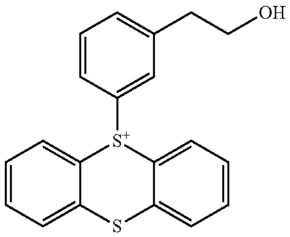

(A26)

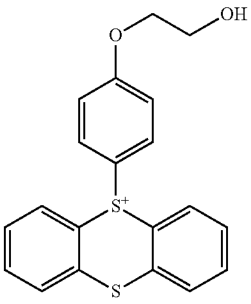

(A27)

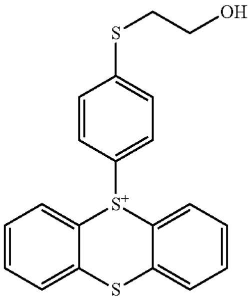

(A28)

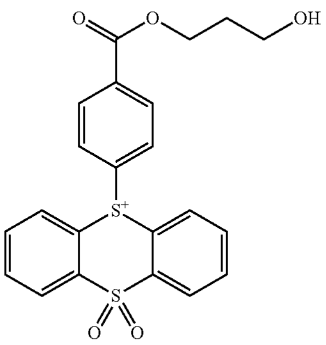

-continued (A29)

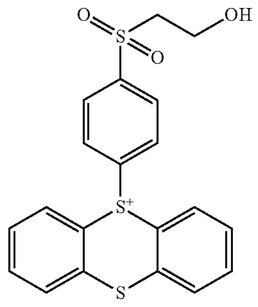

(A30)

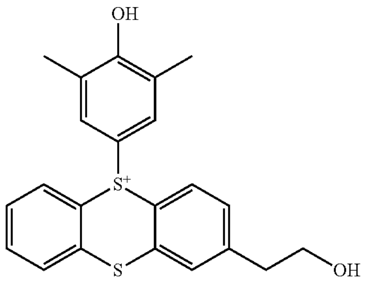

The addition amount of the compound (A) is preferably 0.1 mass % to 40 mass %, more preferably 0.5 mass % to 35 mass %, and even more preferably 3 mass % to 30 mass % as the total amount based on the total solid content of the photosensitive composition.

The molecular weight of the compound (A) is preferably 200 to 2,000, and particularly preferably 400 to 1,000.

Examples of the method for synthesizing the compound (A) include neutralizing the corresponding acid, performing a salt exchanging reaction from a salt of the corresponding acid, or the like. Specifically, synthesis is possible using a known anion exchanging method or a conversion method using an ion exchange resin described in JP1994-184170A (JP-H06-184170A) or the like.

Specific examples are given below of the compound (A) of the present invention; however, the present invention is not limited thereto.

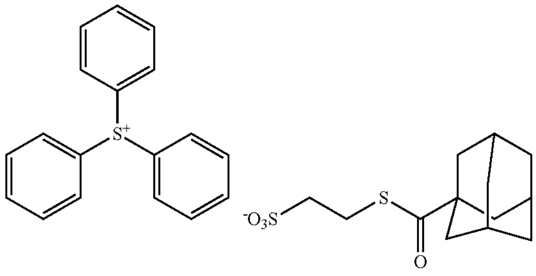

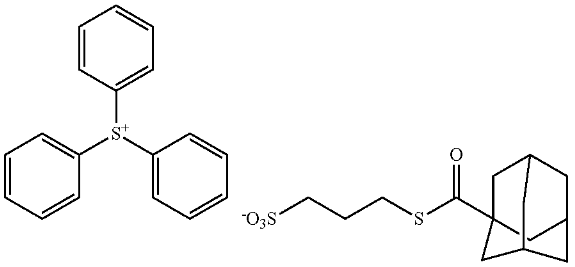

-continued
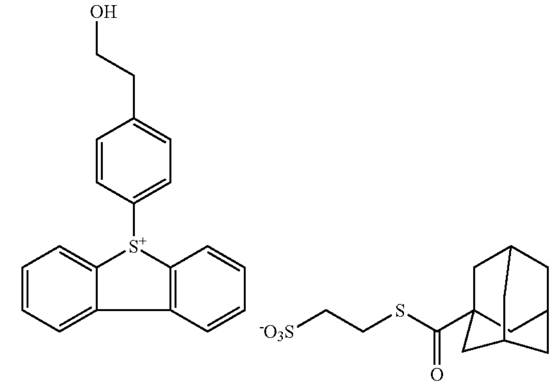
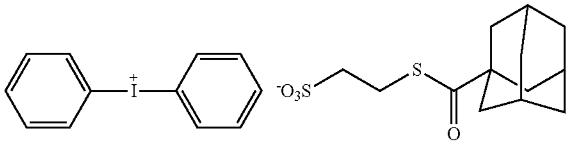
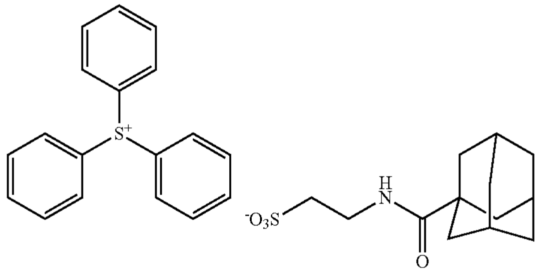
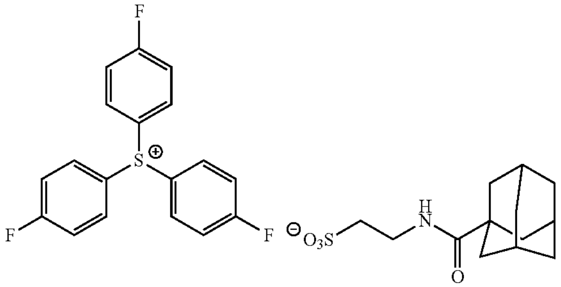
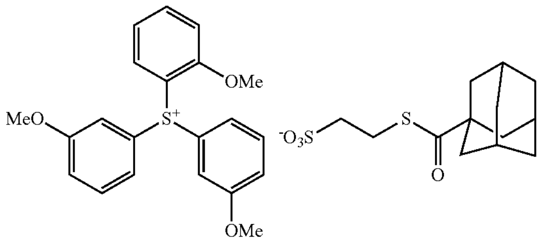
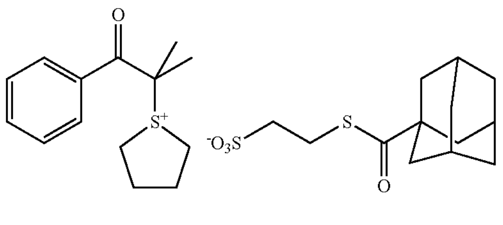
-continued
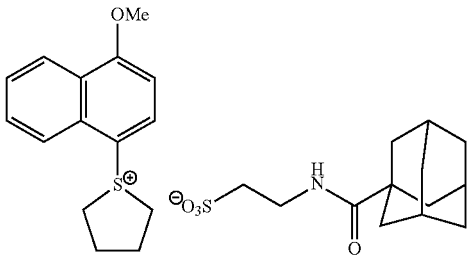
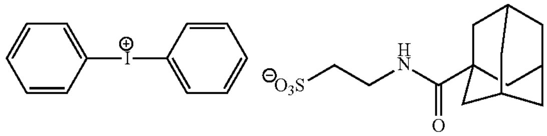
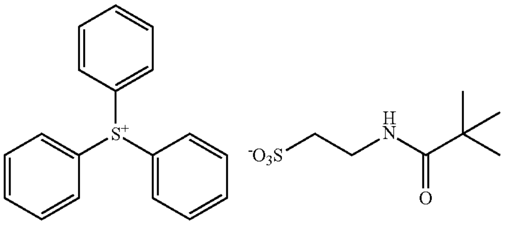
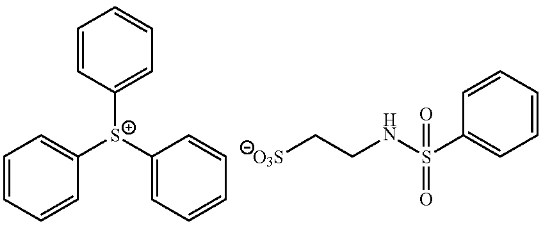
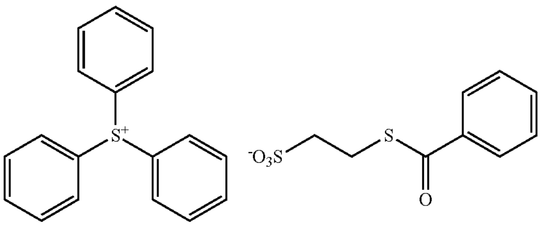
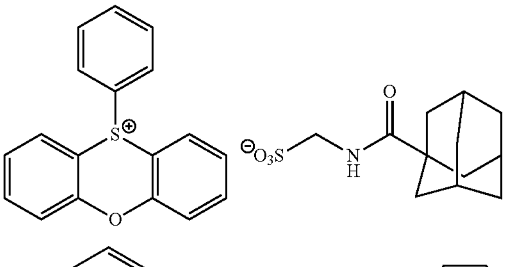
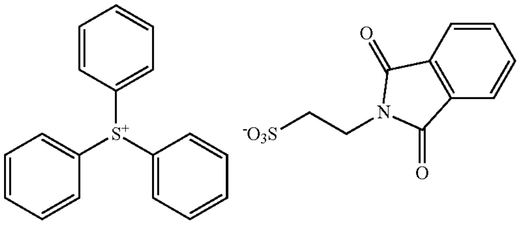

-continued

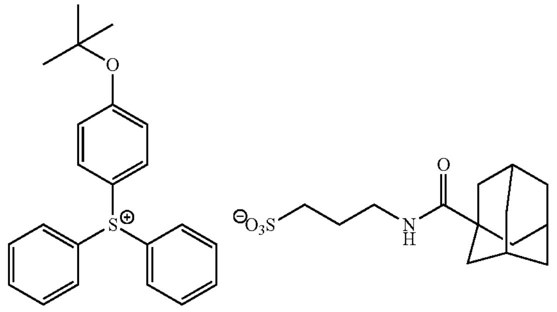

[2] Compound (B) which has a Phenolic Hydroxyl Group

The active light sensitive or radiation sensitive resin composition of the present invention preferably contains the compound (B) which has a phenolic hydroxyl group (also referred to below as compound (B)).

The phenolic hydroxyl group in the present application is a group formed by substituting a hydrogen atom of an aromatic ring group with a hydroxy group. The aromatic ring of the aromatic ring group is a monocyclic or polycyclic aromatic ring and examples thereof include a benzene ring, a naphthalene ring, and the like.

The compound (B) which has a phenolic hydroxyl group is not particularly limited as long as the compound (B) has a phenolic hydroxyl group, and may be a relatively low-molecular-weight compound such as a molecular resist, or may be a resin. Here, as the molecular resist, for example, it is possible to use the low-molecular-weight cyclic polyphenolic compounds described in JP2009-173623A and JP2009-173625A.

The compound (B) which has a phenolic hydroxyl group is preferably a resin from the point of view of reactivity and sensitivity.

In a case where the compound (B) which has a phenolic hydroxyl group is a resin, the resin preferably contains a repeating unit which has at least one type of phenolic hydroxyl group. The repeating unit which has a phenolic hydroxyl group is not particularly limited, but is preferably the repeating unit represented by General Formula (1) below.

(1)

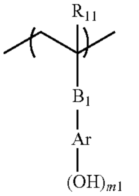

In General Formula (1), $R_{11}$ represents a hydrogen atom, a methyl group which may have a substituent group, or a halogen atom.

$B_1$ represents a single bond or a divalent linking group.

Ar represents an aromatic ring.

m1 represents an integer of 1 or more.

Examples of the methyl group which may have a substituent group in $R_{11}$ include a trifluoromethyl group, a hydroxymethyl group, and the like.

$R^{11}$ is preferably a hydrogen atom or a methyl group, and is preferably a hydrogen atom for the reason of developability.

The divalent linking group denoted by $B_1$ is preferably a carbonyl group, an alkylene group (preferably having 1 to 10 carbon atoms, and more preferably having 1 to 5 carbon atoms), a sulfonyl group (—S(=O)$_2$—), —O—, —NH—, or a divalent linking group in which these are combined.

$B_1$ preferably represents a single bond, a carbonyloxy group (—C(=O)—O—), or —C(=O)—NH—, and more preferably represents a single bond or a carbonyloxy group (—C(=O)—O—), and a single bond is particularly preferable from the point of view of improving the dry etching resistance.

The aromatic ring denoted by Ar is a monocyclic or polycyclic aromatic ring, and examples thereof include an aromatic hydrocarbon ring which may have a substituent group having 6 to 18 carbon atoms such as a benzene ring, a naphthalene ring, an anthracene ring, a fluorene ring, a phenanthrene ring, or an aromatic hetero ring which includes a hetero ring such as a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring, or a thiazole ring. Among these, a benzene ring or a naphthalene ring is preferable from the point of view of resolution, and the benzene ring is the most preferable from the point of view of sensitivity.

m1 is preferably an integer of 1 to 5, and 1 is the most preferable. When m1 is 1 and Ar is a benzene ring, the substitution position of —OH may be a para position, a meta position, or an ortho position with respect to the bonding position with $B_1$ (in a case where $B_1$ is a single bond, the polymer main chain) of the benzene ring; however, from the point of view of the cross-linking reactivity, the para position or the meta position is preferable and the para position is more preferable.

The aromatic ring denoted by Ar may have a substituent group other than the group represented by —OH described above, and examples of the substituent group include an alkyl group, a cycloalkyl group, a halogen atom, a hydroxyl group, an alkoxy group, a carboxyl group, an alkoxycarbonyl group, an alkylcarbonyl group, an alkylcarbonyloxy group, an alkylsulfonyloxy group, and an arylcarbonyl group.

The repeating unit which has a phenolic hydroxyl group is more preferably the repeating unit represented by General Formula (2) below for the reasons of the cross-linking reactivity, the developability, and the dry etching resistance.

(2)

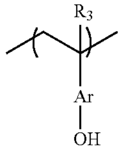

In General Formula (2), $R_3$ represents a hydrogen atom or a methyl group.

Ar represents an aromatic ring.

$R_3$ represents a hydrogen atom or a methyl group, and a hydrogen atom is preferable for reasons of developability.

Ar in General Formula (2) has the same meanings as Ar in General Formula (1) and the preferable ranges thereof are also the same.

The repeating unit represented by General Formula (2) is preferably a repeating unit which is derived from hydroxystyrene (that is, a repeating unit in which $R_3$ in General Formula (2) is a hydrogen atom and Ar is a benzene ring) from the point of view of sensitivity.

The compound (B) which is the resin may be formed of only repeating units which have a phenolic hydroxyl group as described above. The compound (B) which is the resin may have a repeating unit as described below other than the repeating unit which has a phenolic hydroxyl group as described above. In that case, the content of the repeating unit which has a phenolic hydroxyl group is preferably 10 mol % to 100 mol %, more preferably 30 mol % to 97 mol %, and even more preferably 40 mol % to 95 mol %, with respect to all of the repeating units of the compound (B) which is the resin. Due to this, in particular, in a case where the resist film is a thin film (for example, in a case where the thickness of the resist film is 10 nm to 150 nm), it is possible to more reliably reduce the dissolution speed of the exposed section in the resist film of the present invention formed using the compound (B) with respect to the alkali developer (that is, it is possible to more reliably control the dissolution speed of the resist film using the compound (B) to be the optimum speed). As a result, it is possible to more reliably improve the sensitivity.

Examples of repeating units which have a phenolic hydroxyl group are described below; however, the present invention is not limited thereto.

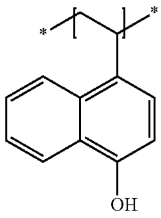
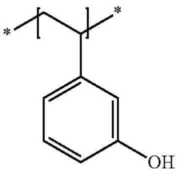
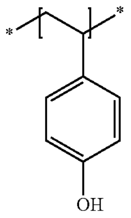
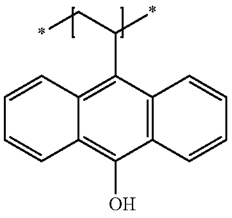
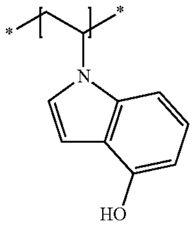
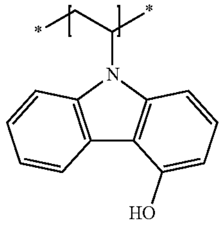
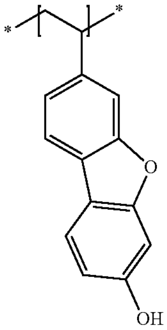
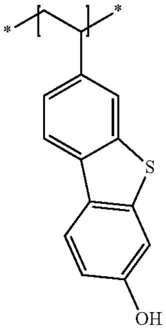
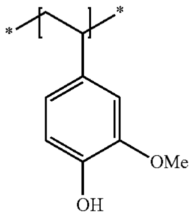
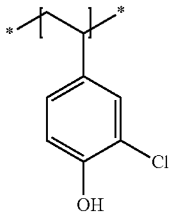

-continued

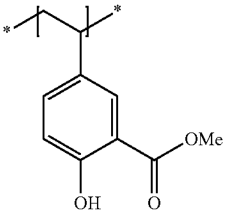
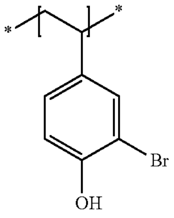
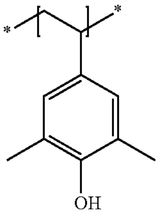
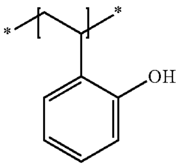
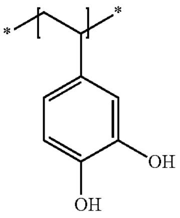
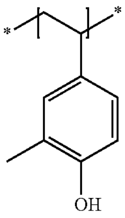
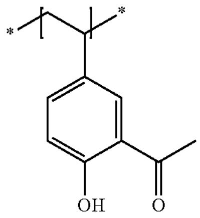
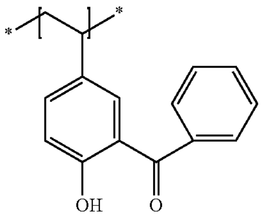
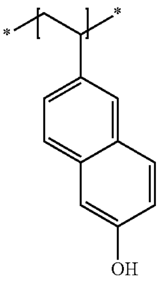
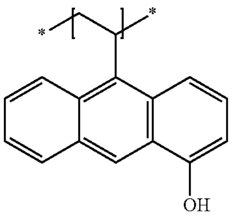
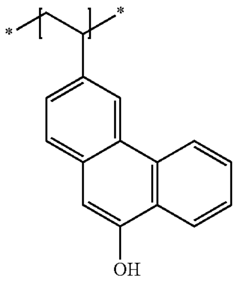
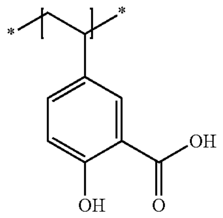
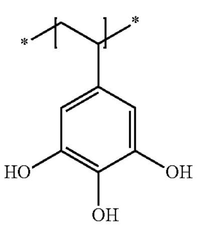
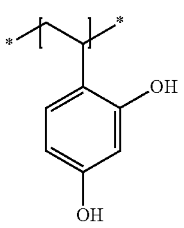
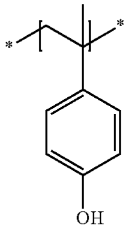
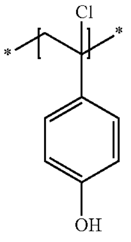
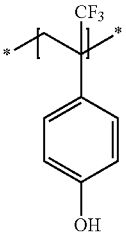
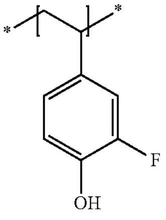

-continued

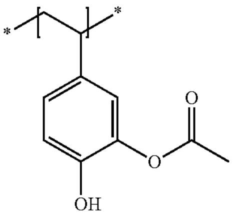
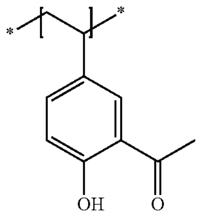
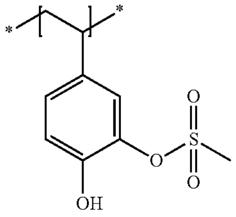
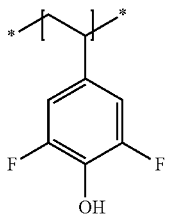
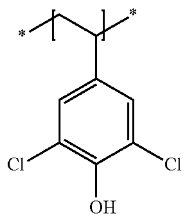
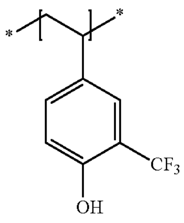
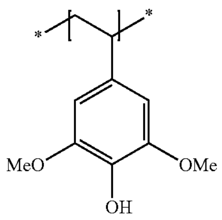
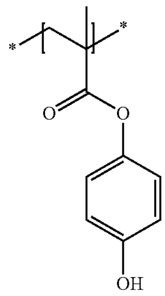
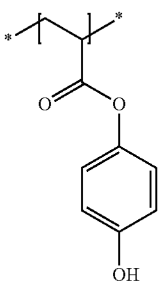
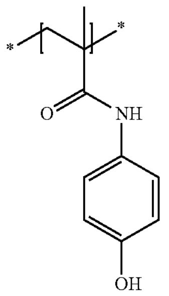
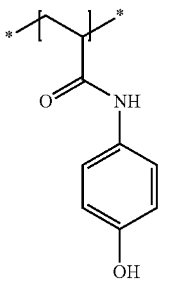
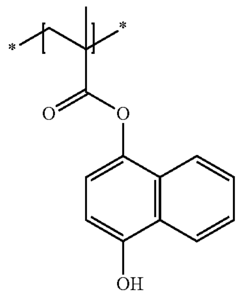
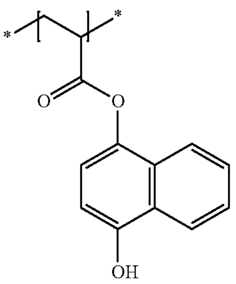
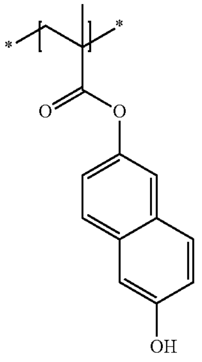

-continued

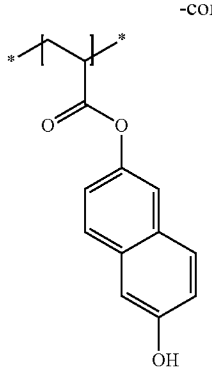
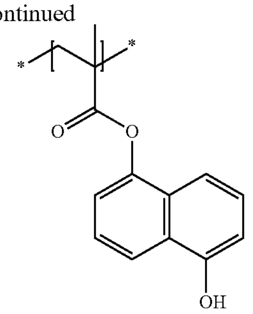
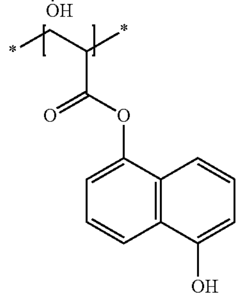

Compound (B) is a group which has a non-acid-decomposable polycyclic alicyclic hydrocarbon structure and preferably has a structure in which the hydrogen atom of the phenolic hydroxyl group is substituted since a high glass transition temperature (Tg) is obtained and the dry etching resistance is favorable.

The compound (B) particularly preferably has the specific structure described above in a case where the compound (B) is a non-acid-decomposable resin.

By the compound (B) having the specific structure described above, the glass transition temperature (Tg) of the compound (B) is increased, it is possible to form an extremely hard resist film, and it is possible to control the acid diffusibility and the dry etching resistance. Accordingly, since the acid diffusibility is extremely suppressed in the sections exposed to active light or radiation such as electron beams or extreme ultraviolet light, the resolving power, the pattern shape, and the LER are superior in fine patterns. In addition, it is considered that the compound (B) having a non-acid-decomposable polycyclic alicyclic hydrocarbon structure contributes to the further improvement in the dry etching resistance.

Furthermore, although the details are unclear, it is presumed that the polycyclic alicyclic hydrocarbon structure has high hydrogen radical donating properties, is a source of hydrogen during decomposition in the photoacid generator, further improves the decomposition efficiency of the photoacid generator, and further increases the acid generation efficiency, and, due to this, it is considered to contribute to excellent sensitivity.

In the specific structure described above which compound (B) according to the present invention may have, an aromatic ring, such as a benzene ring, and a group which has a non-acid-decomposable polycyclic alicyclic hydrocarbon structure are linked via an oxygen atom derived from a phenolic hydroxyl group. As described above, the structure not only contributes to the high dry etching resistance, but is able to increase the glass transition temperature (Tg) of the compound (B), and it is presumed that a higher resolving power is provided due to the effect of the above combination.

In the present invention, non-acid-decomposability has the meaning of a property in which a decomposition reaction is not caused by the acid generated by the acid generator.

More specifically, a group which has a non-acid-decomposable polycyclic alicyclic hydrocarbon structure is preferably a group which is stable in an acid and an alkali. A group which is stable in an acid and an alkali has the meaning of a group which does not exhibit acid-decomposability or alkali-decomposability. Here, the acid-decomposability has the meaning of a property in which a decomposition reaction is caused due to the action of the acid which is generated by the acid generator, and examples of groups which exhibit acid-decomposability include the acid-decomposable groups described in "Repeating unit which has acid-decomposable group" to be described below.

In addition, the alkali-decomposability has the meaning of a property in which a decomposition reaction is caused due to the action of the alkali developer, and examples of groups which exhibit alkali-decomposability include groups (for example, groups which have a lactone structure or the like) which are included in resins which are favorably used in positive type active light sensitive or radiation sensitive resin compositions and which are dissolved by the action of alkali developers known in the related art and of which the dissolution speed is increased in the alkali developer.

The group having a polycyclic alicyclic hydrocarbon structure is not particularly limited as long as the group is a monovalent group which has a polycyclic alicyclic hydrocarbon structure; however, the total number of carbon atoms is preferably 5 to 40, and more preferably 7 to 30. The polycyclic alicyclic hydrocarbon structure may have an unsaturated bond in the ring.

The polycyclic alicyclic hydrocarbon structure in the group which has a polycyclic alicyclic hydrocarbon structure has the meaning of a structure having a plurality of monocyclic type alicyclic hydrocarbon groups or a polycyclic type alicyclic hydrocarbon structure, and may be a bridged type. The monocyclic type alicyclic hydrocarbon group is preferably a cycloalkyl group having 3 to 8 carbon atoms, examples thereof include a cyclopropyl group, a cyclopentyl group, a cyclohexyl group, a cyclobutyl group, a cyclooctyl group, and the like, and the structure having a plurality of monocyclic type alicyclic hydrocarbon groups has a plurality of these groups. In the structure having a plurality of the monocyclic type alicyclic hydrocarbon groups, the number of the monocyclic type alicyclic hydrocarbon groups is preferably 2 to 4, and particularly preferably 2.

Examples of the polycyclic type alicyclic hydrocarbon structure include bicyclo, tricyclo, and tetracyclo structures having 5 or more carbon atoms, and polycyclic cyclo structures having 6 to 30 carbon atoms are preferable and examples thereof include an adamantane structure, a decalin structure, a norbornane structure, a norbornene structure, a cedrol structure, an isobornane structure, a bornane structure, a dicyclopentane structure, an α-pinene structure, a tricyclodecane structure, a tetracyclododecane structure, or an androstane structure. Here, some of the carbon atoms in the monocyclic or polycyclic cycloalkyl group may be substituted with a hetero atom such as an oxygen atom.

Preferable examples of the polycyclic alicyclic hydrocarbon structure described above include an adamantane structure, a decalin structure, norbornane structure, norbornene structure, a cedrol structure, a structure having a plurality of cyclohexyl groups, a structure having a plurality of cycloheptyl groups, a structure having a plurality of cyclooctyl groups, a structure having a plurality of cyclodecanyl groups, a structure having a plurality of cyclododecanyl groups, and a tricyclodecane structure, and an adamantane structure is most preferable from the point of view of the dry etching resistance (that is, the group which has a non-acid-decomposable polycyclic alicyclic hydrocarbon structure is most preferably a group which has a non-acid-decomposable adamantane structure).

The chemical formulae of these polycyclic alicyclic hydrocarbon structures (with regard to the structures which have a plurality of monocyclic type alicyclic hydrocarbon groups, the monocyclic type alicyclic hydrocarbon structure corresponding to the monocyclic type alicyclic hydrocarbon groups (specifically, the structures of Formulae (47) to (50) below)) are shown below.

(1)

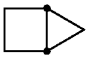

(2)

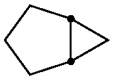

(3)

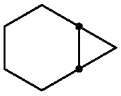

(4)

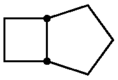

(5)

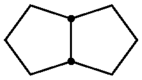

(6)

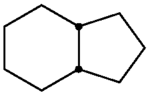

(7)

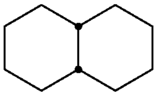

(8)

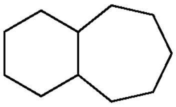

(9)

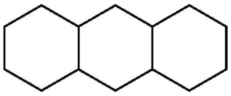

(10)

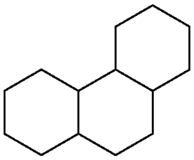

(11)

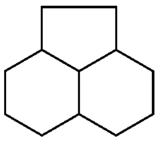

-continued
(12)
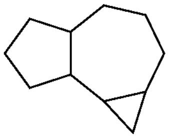
(13)
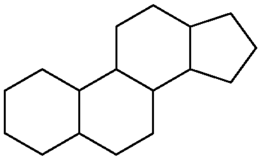
(14)
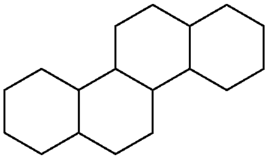
(15)
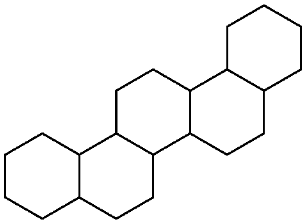
(16)
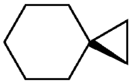
(17)
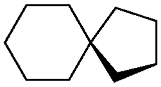
(18)
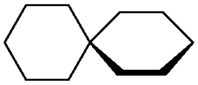
(19)
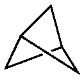
(20)
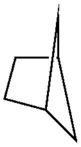
(21)
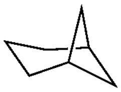
(22)
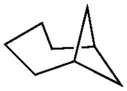
(23)
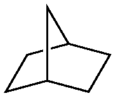
-continued
(24)
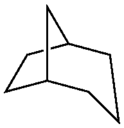
(25)
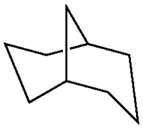
(26)
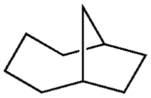
(27)
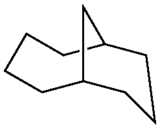
(28)
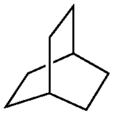
(29)
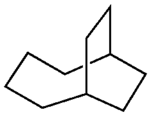
(30)
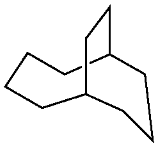
(31)
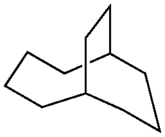
(32)
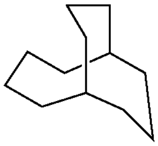
(33)
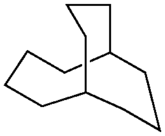
(34)
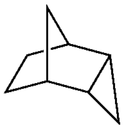

-continued (35)

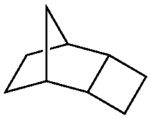

(36)

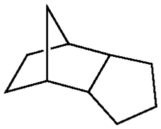

(37)

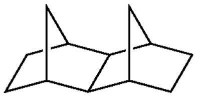

(38)

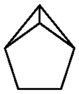

(39)

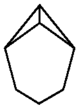

(40)

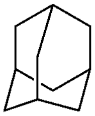

(41)

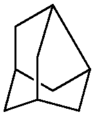

(42)

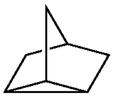

(43)

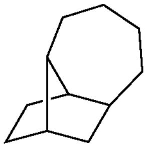

(44)

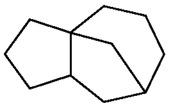

(45)

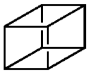

(46)

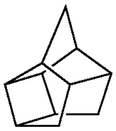

(47)

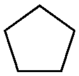

-continued (48)

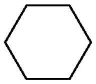

(49)

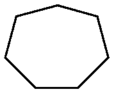

(50)

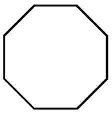

(51)

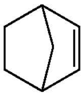

Furthermore, the polycyclic alicyclic hydrocarbon structure described above may have a substituent group and examples of the substituent group include an alkyl group (preferably having 1 to 6 carbon atoms), a cycloalkyl group (preferably having 3 to 10 carbon atoms), an aryl group (preferably having 6 to 15 carbon atoms), a halogen atom, a hydroxyl group, an alkoxy group (preferably having 1 to 6 carbon atoms), a carboxyl group, a carbonyl group, a thiocarbonyl group, an alkoxycarbonyl group (preferably having 2 to 7 carbon atoms), and a group formed by combining these groups (preferably having 1 to 30 carbon atoms in total, and more preferably having 1 to 15 carbon atoms in total).

The polycyclic alicyclic hydrocarbon structure described above is preferably a structure represented by any one of Formulae (7), (23), (40), (41), and (51) above and a structure having two monovalent groups in which one arbitrary hydrogen atom is a bond in the structure of Formula (48) above, more preferably a structure represented by any one of Formulae (23), (40), and (51) above and a structure having two monovalent groups in which one arbitrary hydrogen atom is a bond in the structure of Formula (48) above, and most preferably a structure represented by Formula (40) above.

The group which has a polycyclic alicyclic hydrocarbon structure is preferably a monovalent group in which one arbitrary hydrogen atom of the polycyclic alicylic hydrocarbon structure described above is a bond.

A structure in which a hydrogen atom of the phenolic hydroxyl group is substituted in the group which has the non-acid-decomposable polycyclic alicyclic hydrocarbon structure described above is preferably contained in the compound (B) as the resin which is the repeating unit which has a structure in which the hydrogen atom of the phenolic hydroxyl group is substituted with the group which has the non-acid-decomposable polycyclic alicyclic hydrocarbon structure described above, and is more preferably contained in the compound (B) as the repeating unit represented by General Formula (3) below.

(3)

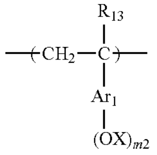

In General Formula (3), $R_{13}$ represents a hydrogen atom or a methyl group.

X represents a group which has a non-acid-decomposable polycyclic alicyclic hydrocarbon structure.

$Ar_1$ represents an aromatic ring.

m2 is an integer of 1 or more.

$R_{13}$ in General Formula (3) represents a hydrogen atom or a methyl group; however, a hydrogen atom is particularly preferable.

Examples of the aromatic ring denoted by $Ar_1$ in General Formula (3) include an aromatic hydrocarbon ring which may have a substituent group having 6 to 18 carbon atoms such as a benzene ring, a naphthalene ring, an anthracene ring, a fluorene ring, a phenanthrene ring, an aromatic heterocyclic ring which includes a hetero ring such as a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring, or a thiazole ring. Among these, a benzene ring or a naphthalene ring is preferable from the point of view of resolution, and a benzene ring is the most preferable.

The aromatic ring denoted by $Ar_1$ may have a substituent group other than the group represented by —OX described above, and examples of the substituent group include an alkyl group (preferably having 1 to 6 carbon atoms), a cycloalkyl group (preferably having 3 to 10 carbon atoms), an aryl group (preferably having 6 to 15 carbon atoms), a halogen atom, a hydroxyl group, an alkoxy group (preferably having 1 to 6 carbon atoms), a carboxyl group, and an alkoxycarbonyl group (preferably having 2 to 7 carbon atoms), an alkyl group, an alkoxy group, and an alkoxycarbonyl group are preferable, an alkoxy group is more preferable.

X represents a group which has a non-acid-decomposable polycyclic alicyclic hydrocarbon structure. The specific examples and preferable ranges of the groups which have the non-acid-decomposable polycyclic alicyclic hydrocarbon structure represented by X are the same as described above. X is more preferably a group represented by —Y—$X_2$ in General Formula (4) described below.

m2 is preferably an integer of 1 to 5, and most preferably 1. When m2 is 1 and $Ar_1$ is a benzene ring, the substitution position of —OX may be a para position, a meta position, or an ortho position with respect to the bonding position with the polymer main chain of the benzene ring; however, the para position or the meta position is preferable and the para position is more preferable.

In the present invention, the repeating unit represented by General Formula (3) is preferably a repeating unit represented by General Formula (4) below.

When using the resin (B) which has the repeating unit represented by General Formula (4), since the Tg of the resin (B) is increased and an extremely hard resist film is formed, it is possible to more reliably control the diffusibility of the acid and the dry etching resistance.

(4)

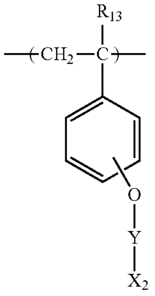

In General Formula (4), $R_{13}$ represents a hydrogen atom or a methyl group.

Y represents a single bond or a divalent linking group.

$X_2$ represents a non-acid-decomposable polycyclic alicyclic hydrocarbon group.

Preferable examples are given below of the repeating unit represented by General Formula (4) which may be used in the present invention.

$R_{13}$ in General Formula (4) represents a hydrogen atom or a methyl group; however, a hydrogen atom is particularly preferable.

In General Formula (4), Y is preferably a divalent linking group. Preferable examples of groups as the divalent linking group denoted by Y preferably include a carbonyl group, a thiocarbonyl group, an alkylene group (preferably having 1 to 10 carbon atoms, and more preferably having 1 to 5 carbon atoms), a sulfonyl group, $—COCH_2—$, —NH—, or a divalent linking group formed by combining the above (preferably having 1 to 20 carbon atoms in total, and more preferably having 1 to 10 carbon atoms in total), of which a carbonyl group, $—COCH_2—$, a sulfonyl group, —CONH—, and —CSNH— are more preferable, a carbonyl group and $—COCH_2—$ are even more preferable, and a carbonyl group is particularly preferable.

$X_2$ represents a polycyclic alicyclic hydrocarbon group and is non-acid-decomposable. The total number of carbon atoms in the polycyclic alicyclic hydrocarbon group is preferably 5 to 40, and more preferably 7 to 30. The polycyclic alicyclic hydrocarbon group may have an unsaturated bond in the ring.

Such polycyclic alicyclic hydrocarbon groups are groups which have a plurality of monocyclic type alicyclic hydrocarbon groups, or polycyclic type alicyclic hydrocarbon groups, and may be a bridged type. The monocyclic type alicyclic hydrocarbon group is preferably a cycloalkyl group having 3 to 8 carbon atoms, and examples thereof include a cyclopropyl group, a cyclopentyl group, a cyclohexyl group, a cyclobutyl group, a cyclooctyl group, or the like, and may have a plurality of these groups. In the group which has a plurality of monocyclic type alicyclic hydrocarbon groups, the number of monocyclic type alicyclic hydrocarbon groups is preferably 2 to 4, and particularly preferably 2.

Examples of the polycyclic type alicyclic hydrocarbon group include groups which have bicyclo, tricyclo, and tetracyclo structures having 5 or more carbon atoms, and groups which have polycyclic cyclo structures having 6 to 30 carbon atoms are preferable and examples thereof include an adamantyl group, a norbornyl group, a norbornenyl group, an isobornyl group, a camphanyl group, a dicyclopentyl group, an α-pinel group, a tricyclodecanyl group, a tetracyclododecyl group, or an androstanyl group. Here, some of the carbon atoms in the monocyclic or polycyclic cycloalkyl group may be substituted with a hetero atom such as an oxygen atom.

The polycyclic alicyclic hydrocarbon group denoted by $X_2$ described above is preferably an adamantyl group, a decalin group, a norbornyl group, a norbornenyl group, a cedrol group, a group which has a plurality of cyclohexyl groups, a group which has a plurality of cycloheptyl groups, a group which has a plurality of cyclooctyl groups, a group which has a plurality of cyclodecanyl groups, a group which has a plurality of cyclododecanyl groups, or a tricyclodecanyl group, and an adamantyl group is most preferable from the point of view of the dry etching resistance. Examples of the chemical formulae of the polycyclic alicyclic hydrocarbon structure in the polycyclic alicyclic hydrocarbon group denoted by $X_2$ include the same chemical formulae as the polycyclic alicyclic hydrocarbon structure in the group which has a polycyclic alicyclic hydrocarbon structure described above, and the preferable ranges thereof are also the same. Examples of the polycyclic alicyclic hydrocarbon group denoted by $X_2$ include monovalent groups in which one arbitrary hydrogen atom in the polycyclic alicyclic hydrocarbon structure described above is a bond.

Furthermore, the alicyclic hydrocarbon group described above may have a substituent group and examples of the substituent group include the same groups described above as the substituent groups which the polycyclic alicyclic hydrocarbon structure may have.

The substitution position of —O—Y—$X_2$ in General Formula (4) may be a para position, a meta position, or an ortho position with respect to the bonding position with the polymer main chain of the benzene ring, and the para position is preferable.

In the present invention, the repeating unit represented by General Formula (3) is most preferably the repeating unit represented by General Formula (4') below.

(4')

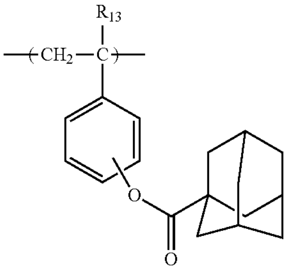

In General Formula (4'), $R_{13}$ represents a hydrogen atom or a methyl group.

$R_{13}$ in General Formula (4') represents a hydrogen atom or a methyl group, and a hydrogen atom is particularly preferable.

The substitution position of the adamantyl ester groups in General Formula (4') may be a para position, a meta position, or an ortho position with respect to the bonding position with the polymer main chain of the benzene ring, and the para position is preferable.

Specific examples of the repeating unit represented by General Formula (3) include the following.

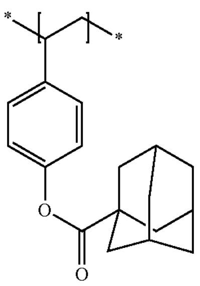

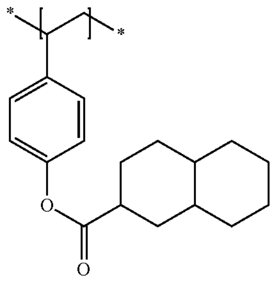

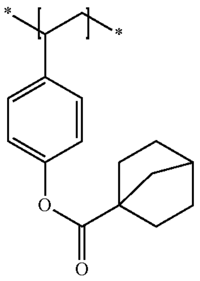

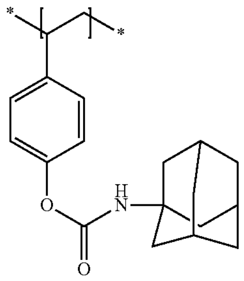

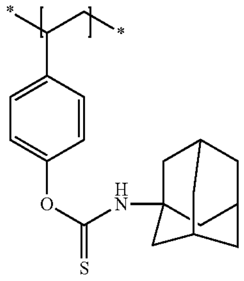

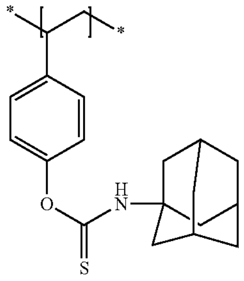

-continued
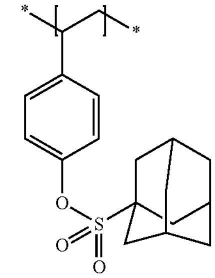
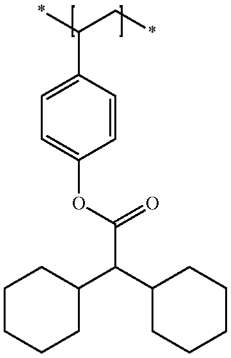
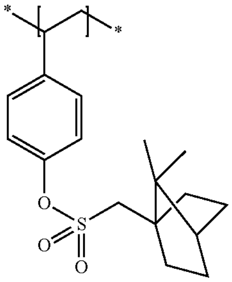
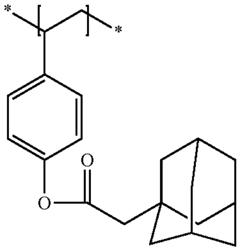
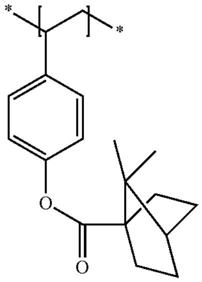
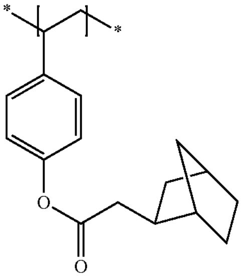
-continued
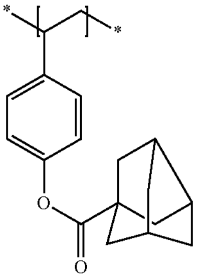
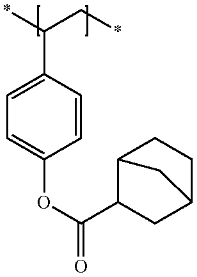
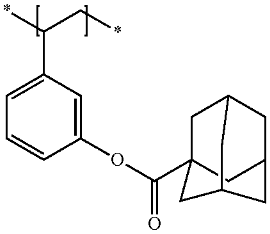
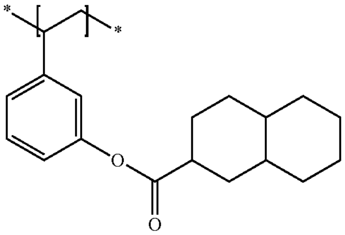
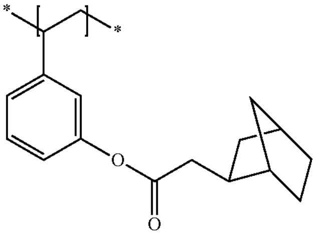
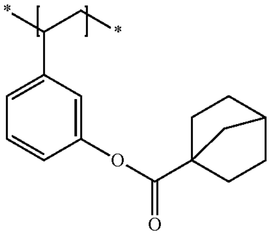
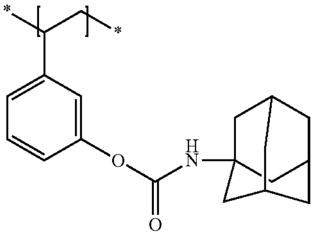

-continued
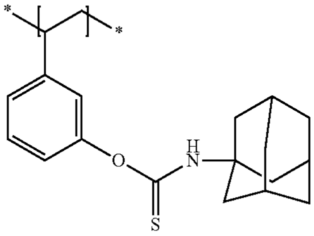
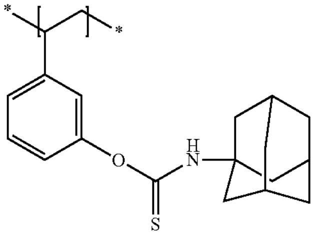
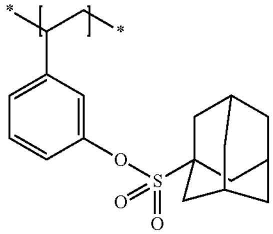
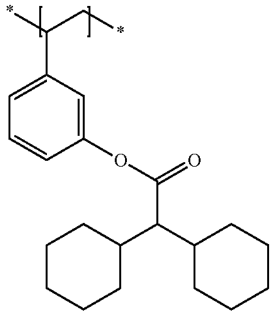
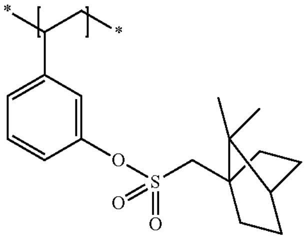
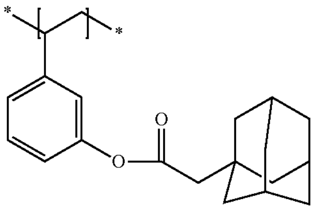
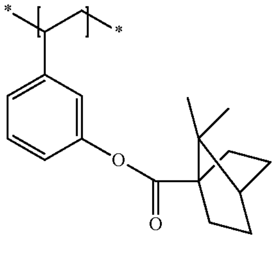
-continued
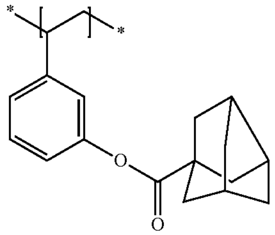
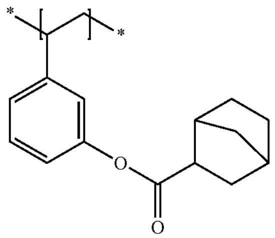
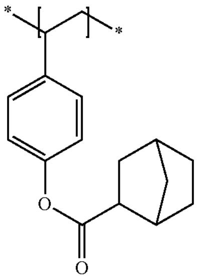
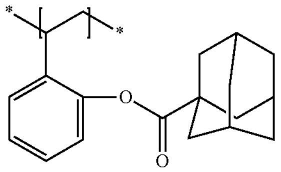
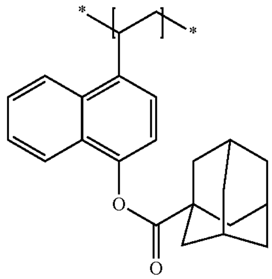
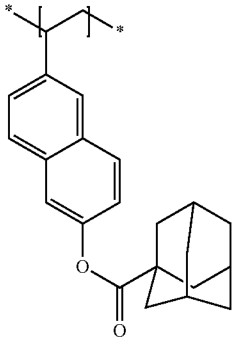

-continued

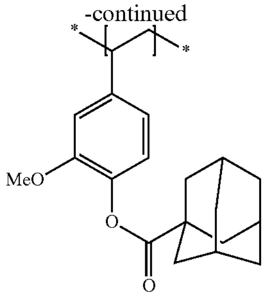

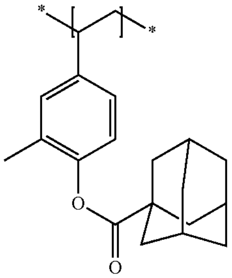

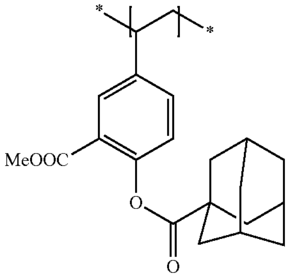

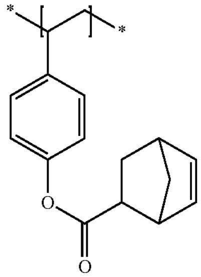

In a case where the compound (B) is a resin and further contains a repeating unit which has a structure in which the hydrogen atom of the phenolic hydroxyl group is substituted in the group which has the non-acid-decomposable polycyclic alicyclic hydrocarbon structure described above, the content of the repeating unit is preferably 1 mol % to 40 mol % and more preferably 2 mol % to 30 mol % with respect to all of the repeating units of compound (B) as the resin.

The compound (B) as the resin to be used in the present invention also preferably further has the repeating unit (referred to below as "other repeating units") as described below as the repeating unit other than the repeating unit described above.

Examples of the polymerizable monomers for forming these other repeating units include styrene, alkyl-substituted styrene, alkoxy-substituted styrene, halogen-substituted styrene, O-alkylated styrene, O-acylated styrene, hydrogenated hydroxystyrene, maleic anhydride, acrylic acid derivatives (acrylic acid, acrylic acid esters, and the like), methacrylic acid derivatives (methacrylic acid, methacrylic acid esters, and the like), N-substituted maleimides, acrylonitrile, methacrylonitrile, vinyl naphthalene, vinyl anthracene, indene which may have a substituent group, and the like.

The compound (B) which is a resin may or may not contain these other repeating units; however, when contained, the content of the other repeating units in the compound (B) which is the resin is generally 1 mol % to 30 mol %, preferably 1 mol % to 20 mol %, and more preferably 2 mol % to 10 mol %, with respect to all of the repeating units which form the compound (B) which is the resin.

It is possible to synthesize the compound (B) as the resin using a well-known radical polymerization method, an anionic polymerization method, or a living radical polymerization method (iniferter method or the like). For example, in the anionic polymerization method, it is possible to obtain a polymer by dissolving a vinyl monomer in an appropriate organic solvent, setting a metal compound (butyl lithium, or the like) as an initiator, and carrying out reaction normally under cooling conditions.

As the compound (B) which is the resin, it is possible to use a polyphenolic compound which is produced by a condensation reaction of a compound which contains aromatic ketones or aromatic aldehydes and 1 to 3 phenolic hydroxyl groups (for example, JP2008-145539A), calixarene derivatives (for example, JP2004-18421A), Noria derivatives (for example, JP2009-222920A), and polyphenolic derivatives (for example, JP2008-94782A), and the compound (B) may be synthesized by being modified with a polymer reaction.

The compound (B) which has a phenolic hydroxyl group used in the present invention is a resin which has a repeating unit having at least one type of phenolic hydroxyl group and is also preferably a resin which further has a repeating unit as described below as the repeating unit other than the repeating unit represented by General Formula (1) above.

For example, in a case where the active light sensitive or radiation sensitive resin composition of the present invention is used as a positive type active light sensitive or radiation sensitive resin composition, the compound (B) which has a phenolic hydroxyl group is a resin which has a repeating unit having at least one type of phenolic hydroxyl group, and includes a repeating unit which has a group (referred to below as an "acid-decomposable group") which is decomposed due to the action of an acid and which generates an alkali-soluble group (below, the compound (B) in this case may be referred to as a "resin which is decomposed due to the action of an acid and of which the solubility in an alkali developer" is increased or an "acid-decomposable resin").

Here, the resin may also be a resin of which the solubility with respect to a developer which includes an organic solvent is decreased by increasing the polarity due to the action of an acid.

As the acid-decomposable group, a group in which the hydrogen atom of an alkali-soluble group such as a —COOH group or an —OH group is substituted with a group which is released due to the action of an acid is preferable. As the group which is released due to the action of an acid, an acetal group or a tertiary ester group is particularly preferable.

Examples of the base resin in a case where the acid-decomposable group is bonded as a side chain include alkali-soluble resins which have an —OH or —COOH group in the side chain. Examples of such alkali-soluble resins include those described below.

The alkali dissolution speed of these alkali-soluble resins is preferably 17 nm/sec or faster when measured (23° C.) using 0.261N tetramethyl ammonium hydroxide (TMAH). This speed is particularly preferably 33 nm/sec or faster.

From this point of view, particularly preferable examples of alkali-soluble resins include resins including hydroxystyrene structural units such as o-, m-, and p-poly(hydroxystyrene) and copolymers thereof, hydrogenated poly(hydroxystyrene), halogen- or alkyl-substituted poly (hydroxystyrene), a partial O-alkylation or O-acylation of poly(hydroxystyrene), styrene-hydroxystyrene copolymers, α-methylstyrene-hydroxystyrene copolymer, and hydrogenated novolak resins; and resins including repeating units which have carboxyl groups such as (meth)acrylic acid and norbornene carboxylic acid.

Preferable examples of repeating units which have acid-decomposable groups include t-butoxycarbonyloxystyrene, 1-alkoxyethoxy styrene, and (meth)acrylic acid tertiary alkyl esters. As the repeating unit, 2-alkyl-2-adamantyl (meth) acrylate and dialkyl (1-adamantyl) methyl (meth)acrylate are more preferable.

The resin which is decomposed due to the action of an acid and of which the solubility in an alkali developer is increased may be obtained, for example, by reacting a precursor of a group which is released due to the action of an acid with the resin, or by copolymerizing an alkali-soluble resin monomer bonded with a group which is released by the action of an acid with various monomers, as described in EP254853B, JP1990-25850A (JP-H02-25850A), JP1991-223860A (JP-H03-223860A), JP1992-251259A (JP-H04-251259A), and the like.

In a case where the composition of the present invention is irradiated with KrF excimer laser light, electron beams, X-rays, or high-energy light beams (for example, EUV) with a wavelength of 50 nm or less, the resin preferably has a hydroxystyrene repeating unit. More preferably, the resin is a copolymer of hydroxystyrene and hydroxystyrene protected by a group which is released due to the action of an acid, or a copolymer of hydroxystyrene and (meth)acrylic acid tertiary alkyl ester.

Specifically, examples of such resins include resins which have the repeating unit represented by General Formula (A) below as the repeating unit which has an acid-decomposable group. The dry etching resistance of the formed pattern is improved by using a resin which has the repeating unit described above.

(A)

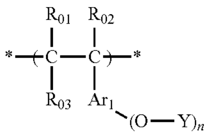

In the formula, $R_{01}$, $R_{02}$, and $R_{03}$ each independently represent a hydrogen atom, an alkyl group, a cycloalkyl group, a halogen atom, a cyano group, or an alkoxycarbonyl group. $Ar_1$ represents an aromatic ring group. Here, $R_{03}$ and $Ar_1$ may bond with each other to form a 5- or 6-membered ring with a main chain of the repeating unit represented by General Formula (A).

n Y's each independently represent a hydrogen atom or a group which is released due to an action of an acid. Here, at least one Y represents a group which is released due to an action of an acid.

n represents an integer of 1 to 4, preferably 1 to 2, and more preferably 1.

The alkyl group as $R_{01}$ to $R_{03}$ is, for example, an alkyl group having 20 or fewer carbon atoms, and preferably a methyl group, an ethyl group, a propyl group, an isopropyl group, an n-butyl group, a sec-butyl group, a hexyl group, a 2-ethylhexyl group, an octyl group, or a dodecyl group. More preferably, these alkyl groups are alkyl groups having 8 or fewer carbon atoms. Here, these alkyl groups may have a substituent group.

The alkyl group which is included in the alkoxycarbonyl group is preferably the same as the alkyl group in $R_{01}$ to $R_{03}$ described above.

The cycloalkyl group may be a monocyclic cycloalkyl group or may be a polycyclic cycloalkyl group. Preferable examples thereof include a monocyclic cycloalkyl group having 3 to 8 carbon atoms such as a cyclopropyl group, a cyclopentyl group, or a cyclohexyl group. Here, these cycloalkyl groups may have a substituent group.

Examples of the halogen atom include a fluorine atom, a chlorine atom, a bromine atom, and an iodine atom, and a fluorine atom is more preferable.

In a case where $R_{03}$ represents an alkylene group, preferable examples of the alkylene group include groups having 1 to 8 carbon atoms such as a methylene group, an ethylene group, a propylene group, a butylene group, a hexylene group, or an octylene group.

The aromatic ring group as $Ar_1$ is preferably a group having 6 to 14 carbon atoms, and examples thereof include a benzene ring, toluene ring, and a naphthalene ring. Here, these aromatic ring groups may have a substituent group.

Examples of the group Y which is released due to the action of an acid include groups represented by $-C(R^{36})(R^{37})(R^{38})$, $-C(=O)-O-C(R^{36})(R^{37})(R^{38})$, $-C(R^{01})(R^{02})(OR^{39})$, $-C(R^{01})(R^{02})-C(=O)-O-C(R^{36})(R^{37})(R^{38})$, and $-CH(R^{36})(Ar)$.

In the formulae, $R^{36}$ to $R^{39}$ each independently represent an alkyl group, a cycloalkyl group, an aryl group, an aralkyl group, or an alkenyl group. $R^{36}$ and $R^{37}$ may be bonded with each other to form a ring structure.

$R^{01}$ and $R^{02}$ each independently represent a hydrogen atom, an alkyl group, a cycloalkyl group, an aryl group, an aralkyl group, or an alkenyl group.

Ar represents an aryl group.

The alkyl group as $R^{36}$ to $R^{39}$, $R^{01}$, or $R^{02}$ is preferably an alkyl group having 1 to 8 carbon atoms, and examples thereof include a methyl group, an ethyl group, a propyl group, an n-butyl group, a sec-butyl group, a hexyl group, and an octyl group.

The cycloalkyl group as $R^{36}$ to $R^{39}$, $R^{01}$, or $R^{02}$ may be a monocyclic cycloalkyl group, or may be a polycyclic cycloalkyl group. The monocyclic cycloalkyl group is preferably a cycloalkyl group having 3 to 8 carbon atoms, and examples thereof include a cyclopropyl group, a cyclobutyl group, a cyclopentyl group, a cyclohexyl group, and cyclooctyl group. The polycyclic cycloalkyl group is preferably a cycloalkyl group having 6 to 20 carbon atoms, and examples thereof include an adamantyl group, a norbornyl group, an isobornyl group, a camphanyl group, a dicyclopentyl group, an α-pinel group, a tricyclodecanyl group, a tetracyclododecyl group, and an androstanyl group. Here, some of the carbon atoms in the cycloalkyl group may be substituted with hetero atoms such as oxygen atoms.

The aryl group as $R^{36}$ to $R^{39}$, $R^{01}$, $R^{02}$, or Ar is preferably an aryl group having 6 to 10 carbon atoms, and examples thereof include a phenyl group, a naphthyl group, and an anthryl group.

The aralkyl group as $R^{36}$ to $R^{39}$, $R^{01}$, or $R^{02}$ is preferably an aralkyl group having 7 to 12 carbon atoms, and examples thereof include a benzyl group, a phenethyl group, and a naphthylmethyl group.

The alkenyl group as $R^{36}$ to $R^{39}$, $R^{01}$, or $R^{02}$ is preferably an alkenyl group having 2 to 8 carbon atoms, and examples thereof include a vinyl group, an allyl group, a butenyl group, and a cyclohexenyl group.

The ring which may be formed by $R_{36}$ and $R_{37}$ bonding with each other may be a monocyclic type, or may be a polycyclic type. The monocyclic type is a preferably a cycloalkane structure having 3 to 8 carbon atoms, and examples thereof include a cyclopropane structure, a cyclobutane structure, a cyclopentane structure, a cyclohexane structure, a cycloheptane structure, and a cyclooctane structure. The polycyclic type is preferably a cycloalkane structure having 6 to 20 carbon atoms, and examples thereof include an adamantane structure, a norbornane structure, a dicyclopentane structure, a tricyclodecane structure, and a tetracyclododecane structure. Here, some of the carbon atoms in the ring structure may be substituted with a hetero atom such as an oxygen atom.

Each group described above may have a substituent group. Examples of the substituent group include an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, and a nitro group. These substituent groups preferably have 8 or fewer carbon atoms.

As the group Y which is released due to the action of an acid, the structure represented by General Formula (B) below is more preferable.

(B)

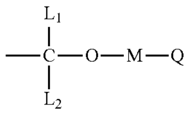

In the formula, $L_1$ and $L_2$ each independently represent a hydrogen atom, an alkyl group, a cycloalkyl group, an aryl group, or an aralkyl group.

M represents a single bond or a divalent linking group.

Q represents an alkyl group, a cycloalkyl group, a cyclic aliphatic group, an aromatic ring group, an amino group, an ammonium group, a mercapto group, a cyano group, or an aldehyde group. Here, these cyclic aliphatic groups and aromatic ring groups may include a hetero atom.

Here, at least two of Q, M, and $L_1$ may bond with each other to form a 5- or 6-membered ring.

The alkyl group as $L_1$ and $L_2$ is, for example, an alkyl group having 1 to 8 carbon atoms, and specific examples thereof include a methyl group, an ethyl group, a propyl group, an isopropyl group, an n-butyl group, a sec-butyl group, a t-butyl group, a hexyl group, and an octyl group.

The cycloalkyl group as $L_1$ and $L_2$ is, for example, a cycloalkyl group having 3 to 15 carbon atoms, and specific examples thereof include a cyclopentyl group, a cyclohexyl group, a norbornyl group, and an adamantyl group.

The aryl group as $L_1$ and $L_2$ is, for example, an aryl group having 6 to 15 carbon atoms, and specific examples thereof include a phenyl group, a tolyl group, a naphthyl group, and an anthryl group.

The aralkyl group as $L_1$ and $L_2$ is, for example, an aralkyl group having 6 to 20 carbon atoms, and specific examples thereof include a benzyl group and a phenethyl group.

The divalent linking group as M is, for example, an alkylene group (for example, a methylene group, an ethylene group, a propylene group, a butylene group, a hexylene group, or an octylene group), a cycloalkylene group (for example, a cyclopentylene group, or a cyclohexylene group), an alkenylene group (for example, an ethylene group, a propenylene group, or a butenylene group), an arylene group (for example, a phenylene group, a tolylene group, or a naphthylene group), —S—, —O—, —CO—, $—SO_2—$, $—N(R_0)—$, or a combination of two or more thereof. Here, $R_0$ is a hydrogen atom or an alkyl group. The alkyl group as $R_0$ is, for example, an alkyl group having 1 to 8 carbon atoms, and specific examples thereof include a methyl group, an ethyl group, a propyl group, an n-butyl group, a sec-butyl, a hexyl group, and an octyl group.

The alkyl group and cycloalkyl group as Q are the same as for each group as $L_1$ and $L_2$ as described above.

Examples of the cyclic aliphatic group or aromatic group as Q include a cycloalkyl group and an aryl group as $L_1$ and $L_2$ described above. The cycloalkyl group and aryl group are preferably a group having 3 to 15 carbon atoms.

Examples of the cyclic aliphatic group or aromatic ring group which include a hetero atom, as Q, include groups which have a heterocyclic structure such as thiirane, cyclothiolane, thiophene, furan, pyrrole, benzothiophene, benzofuran, benzopyrrole, triazine, imidazole, benzimidazole, triazole, thiadiazole, thiazole, and pyrrolidone. However, the cyclic aliphatic group or aromatic ring group which include a hetero atom, as Q, is not particularly limited as long as the group is a ring formed of carbon and hetero atoms or a ring formed only of hetero atoms.

Examples of a ring structure which may be formed by at least two of Q, M, and $L_1$ bonding with each other include a 5- or 6-membered ring structure formed by these forming a propylene group or a butylene group. Here, the 5- or 6-membered ring structure contains an oxygen atom.

Each of the groups represented by $L_1$, $L_2$, M, and Q in General Formula (B) may have a substituent group. Examples of the substituent group include an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, and a nitro group. These substituent groups preferably have 8 or fewer carbon atoms.

The group represented by -(M-Q) is preferably a group having 1 to 30 carbon atoms, and more preferably a groups having 5 to 20 carbon atoms. In particular, from the point of view of suppressing outgassing, a group having 6 or more carbon atoms is preferable.

The acid-decomposable resin may be a resin which has a repeating unit represented by General Formula (X) below as the repeating unit having an acid-decomposable group.

(X)

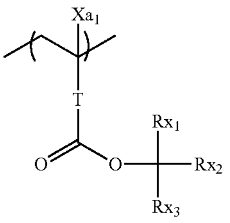

In General Formula (X), $Xa_1$ represents a hydrogen atom, a methyl group, a trifluoromethyl group, or a hydroxymethyl group.

T represents a single bond or a divalent linking group.

$Rx_1$ to $Rx_3$ each independently represent a straight-chain or branched alkyl group, or a monocyclic or polycyclic cycloalkyl group. Here, two of $Rx_1$ to $Rx_3$ may bond with each other to form a monocyclic or polycyclic cycloalkyl group.

Examples of the divalent linking group as T include an alkylene group, a —(COO-Rt)- group, and a —(O-Rt)- group. Here, Rt represents an alkylene group or a cycloalkylene group.

T is preferably a single bond or a —(COO-Rt)- group. Here, Rt is preferably an alkylene group having 1 to 5 carbon atoms, and a $—CH_2—$ group or a $—(CH_2)_3—$ group are more preferable.

The alkyl group as $Rx_1$ to $Rx_3$ is preferably an alkyl group having 1 to 4 carbon atoms such as a methyl group, an ethyl group, an n-propyl group, an isopropyl group, an n-butyl group, an isobutyl group, or a t-butyl group.

The cycloalkyl group as $Rx_1$ to $Rx_3$ is preferably a monocyclic cycloalkyl group such as a cyclopentyl group or cyclohexyl group, or a polycyclic cycloalkyl group such as a norbornyl group, a tetracyclodecanyl group, a tetracyclododecanyl group, or an adamantyl group.

As the cycloalkyl group which may be formed by two of $Rx_1$ to $Rx_3$ bonding with each other to form, a monocyclic cycloalkyl group such as a cyclopentyl group or cyclohexyl group, or a polycyclic cycloalkyl group such as a norbornyl group, a tetracyclodecanyl group, a tetracyclododecanyl group, or an adamantyl group is preferable.

In particular, $Rx_1$ is a methyl group or an ethyl group, and an aspect in which $Rx_2$ and $Rx_3$ bond with each other to form the cycloalkyl group described above is preferable.

Specific examples are given below of the acid-decomposable repeating unit; however, the present invention is not limited thereto.

(In the formulae, Rx is H, $CH_3$, $CF_3$, $CH_2OH$, Rxa, and Rxb are respectively alkyl groups having 1 to 4 carbon atoms)

1

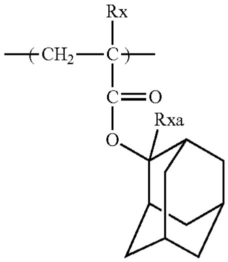

2

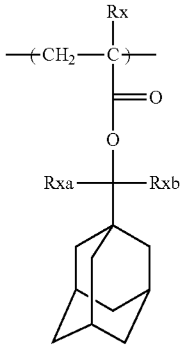

-continued

3

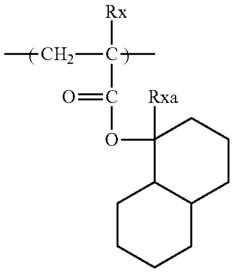

4

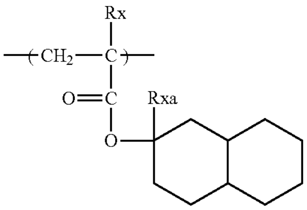

5

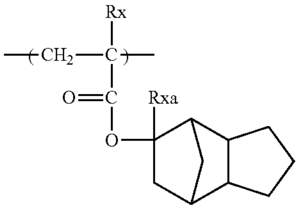

6

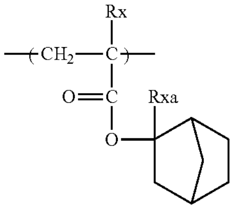

7

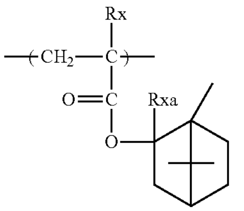

8

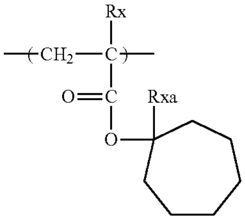

-continued
9
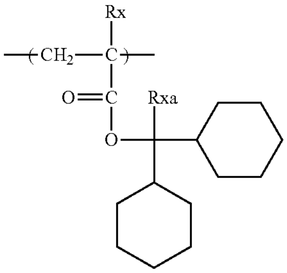
10
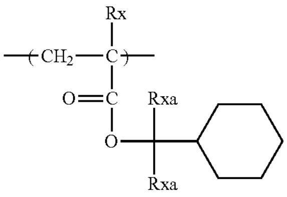
11
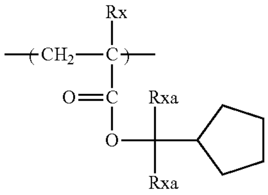
12
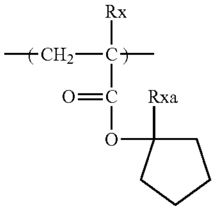
13
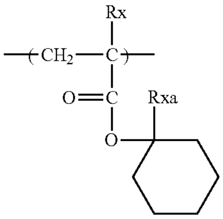
14
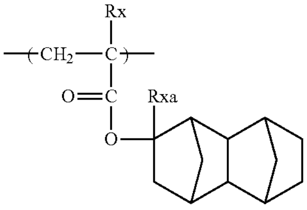
15
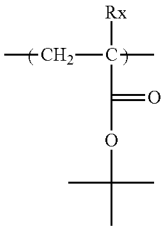
-continued
16
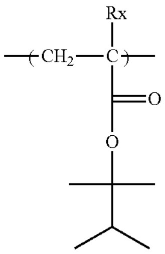
17
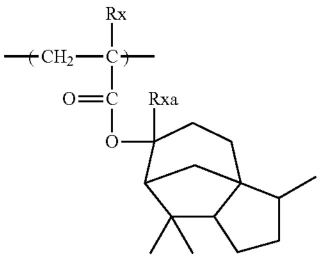
18
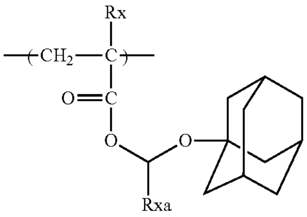
19
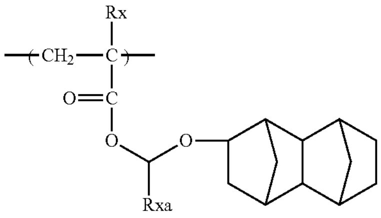
20
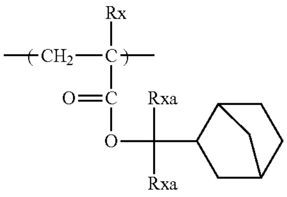
21
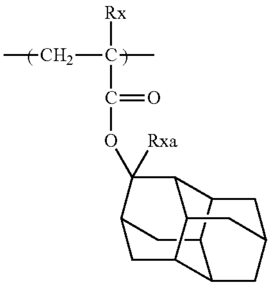

-continued

22

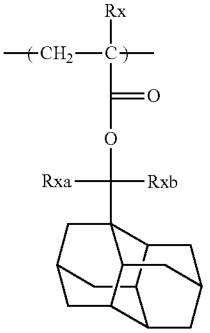

23

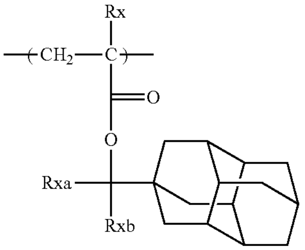

24

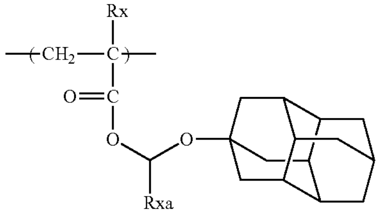

25

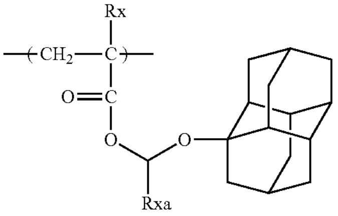

The content of the repeating unit (the total thereof when a plurality of types are present) which has an acid-decomposable group in the acid-decomposable resin is preferably in a range of 3 mol % to 90 mol %, more preferably 5 mol % to 80 mol %, and particularly preferably 7 mol % to 70 mol %, with respect to all of the repeating units of the acid-decomposable resin.

The compound (B) of the present invention may have a repeating unit which is provided with an ionic structure moiety which generates an acid in a side chain of the resin by being decomposed due to irradiation with active light or radiation. Examples of such repeating units include the repeating units represented by General Formula (4) below.

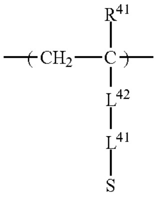

(4)

$R^{41}$ represents a hydrogen atom or a methyl group. $L^{41}$ represents a single bond or a divalent linking group. $L^{42}$ represents a divalent linking group. S represents a structural moiety which generates acid in a side chain by being decomposed due to irradiation with active light or radiation.

Specific examples are given below of the compound (B) described above; however, the present invention is not limited thereto.

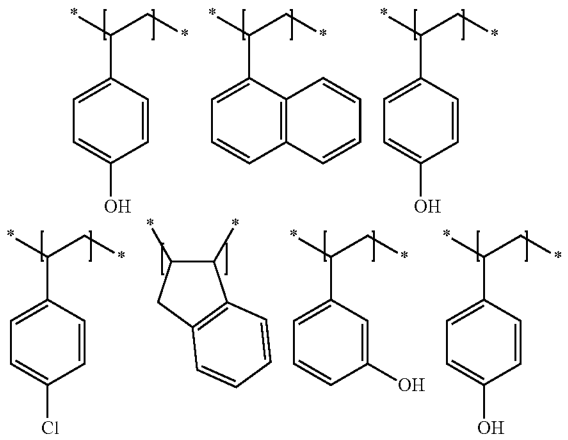

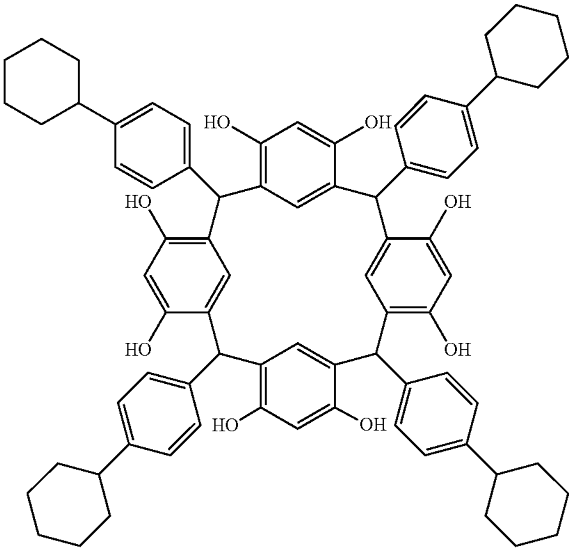

Specific examples are given below of the compound (B) as a compound which has a structure in which a hydrogen atom of a phenolic hydroxyl group is substituted in a group which has a non-acid-decomposable polycyclic alicyclic hydrocarbon structure; however, the present invention is not limited thereto.

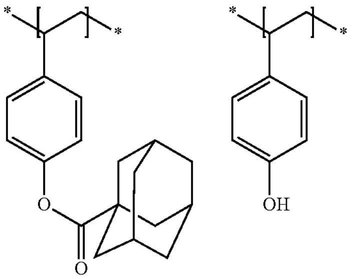
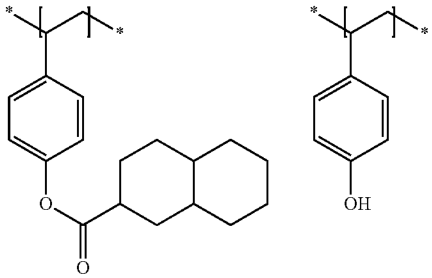
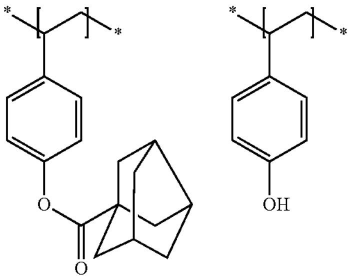
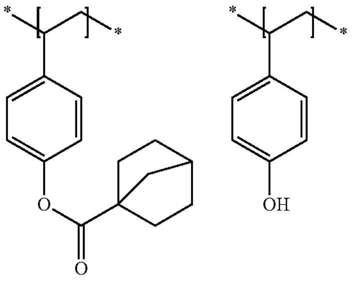
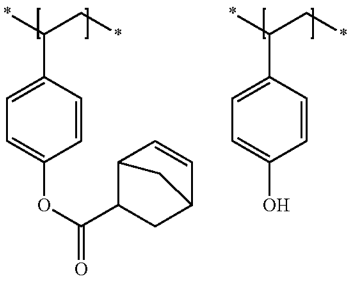
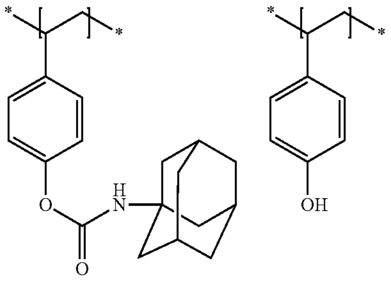
-continued
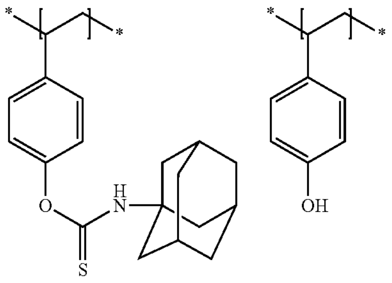
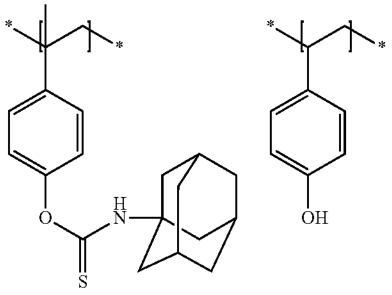
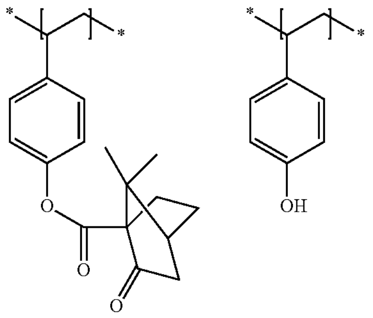
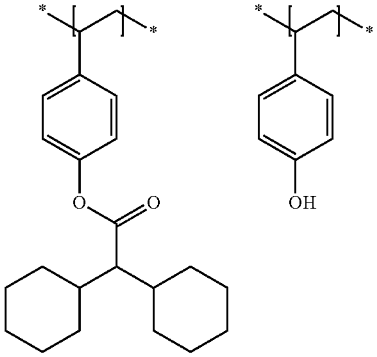
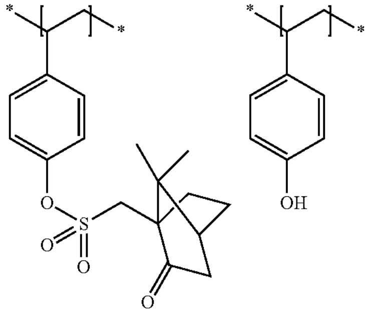

-continued
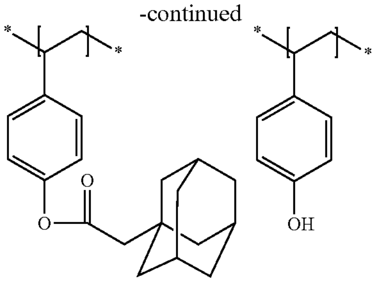
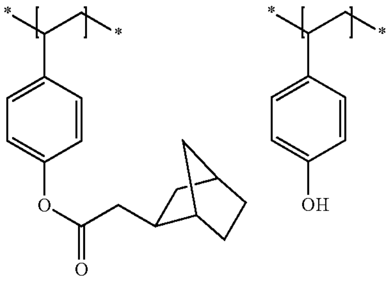
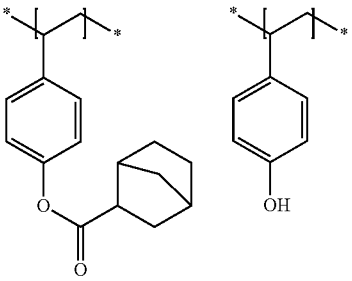
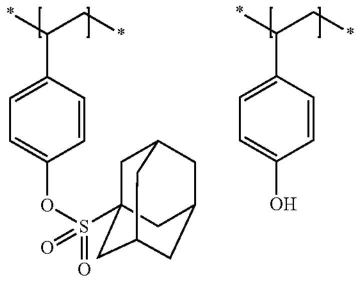
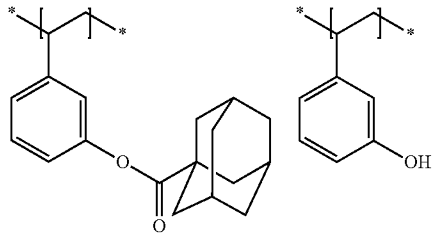
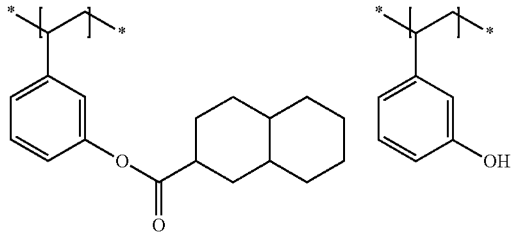
-continued
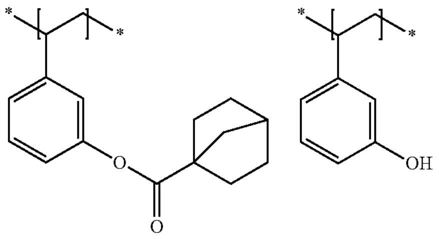
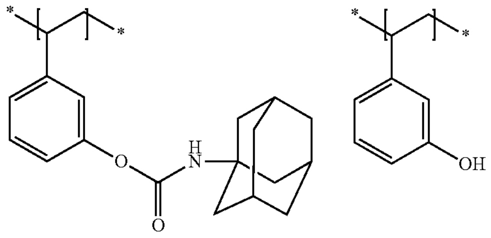
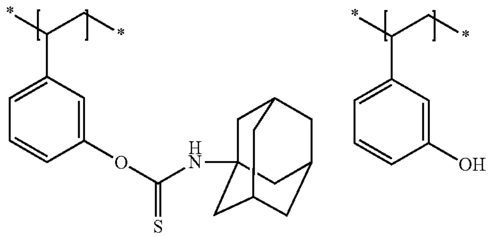
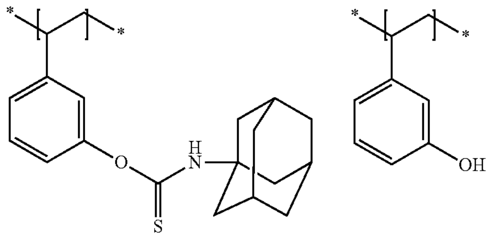
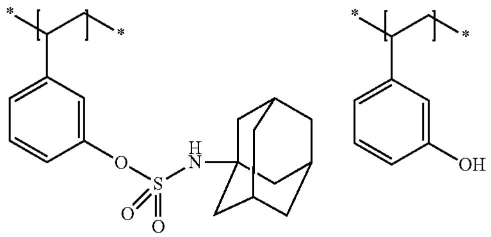
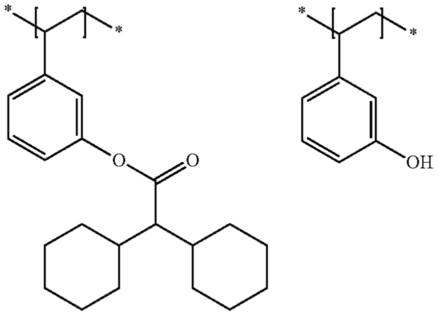

-continued
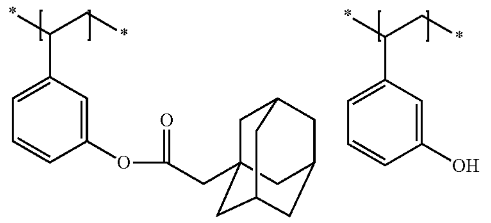
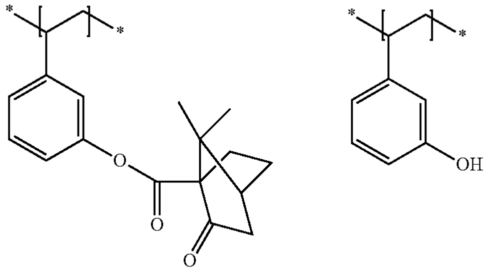
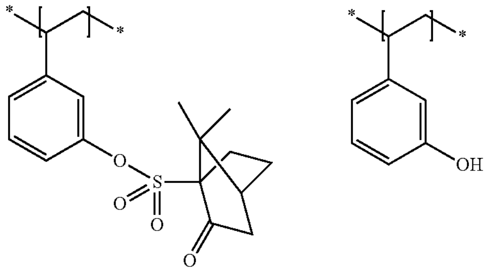
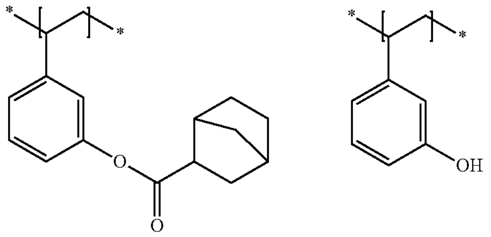
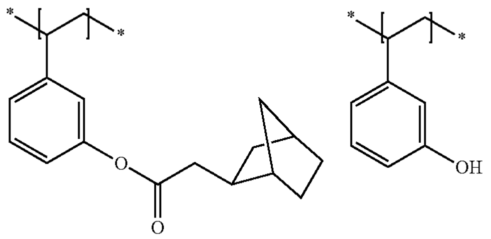
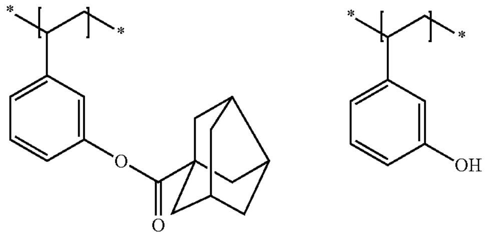
-continued
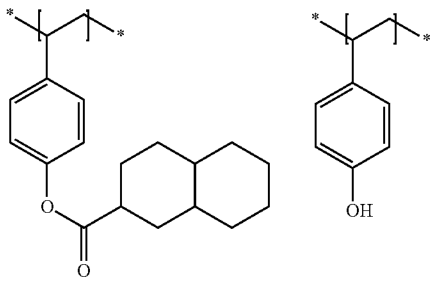
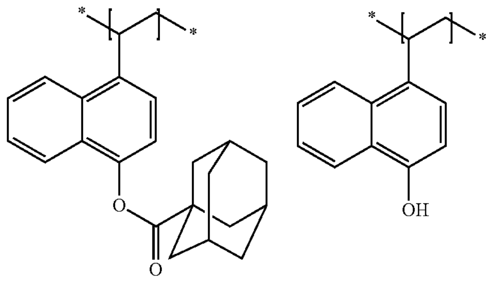
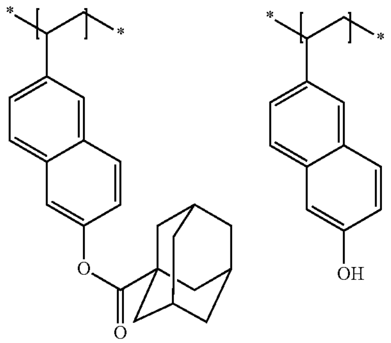
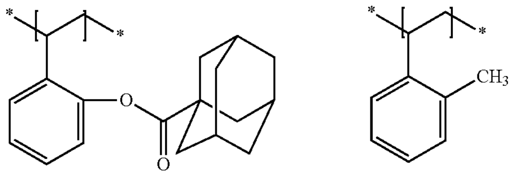
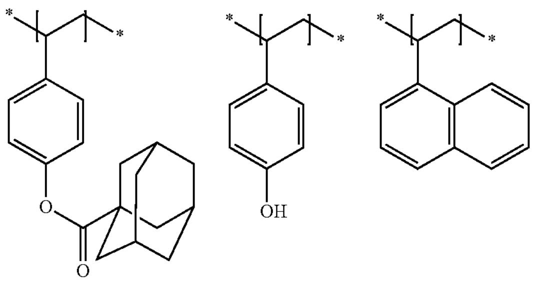
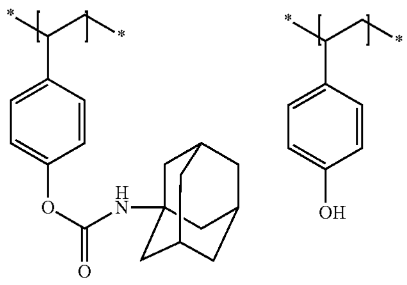

-continued
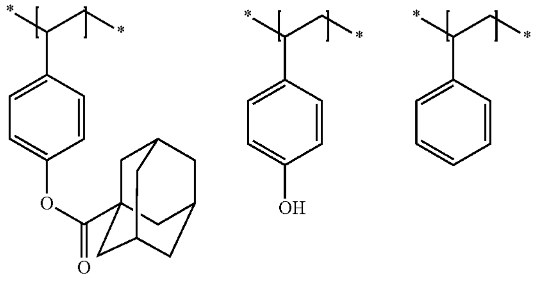
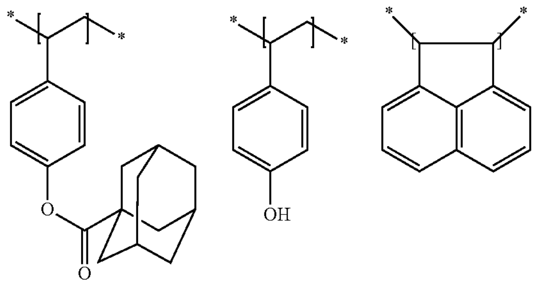
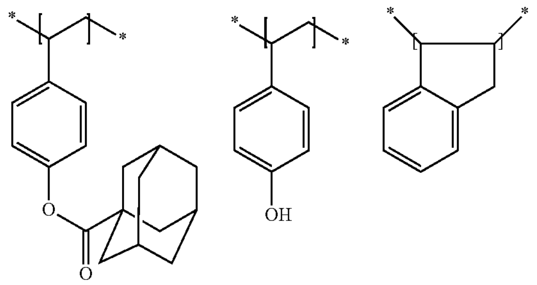
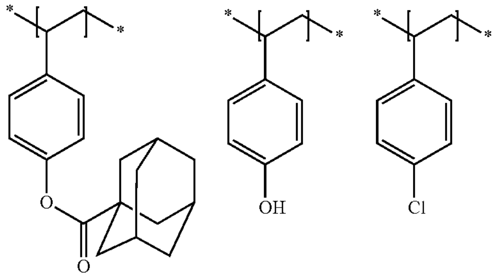
-continued
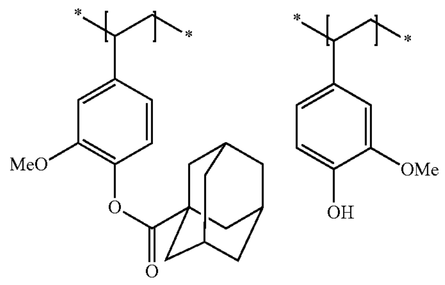
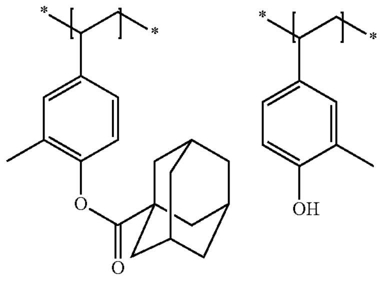
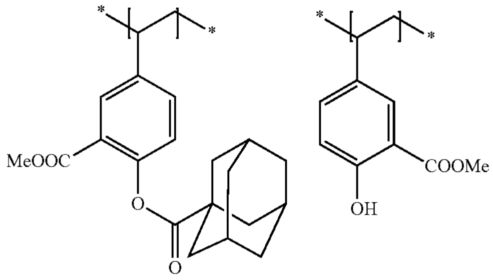
Specific examples are given below of the compound (B) as the acid-decomposable resin described above; however, the present invention is not limited thereto.
(R-1)
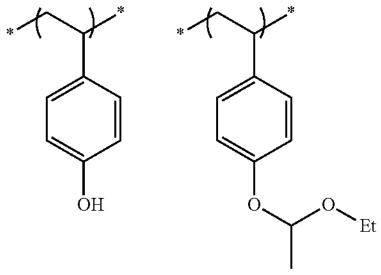
(R-2)
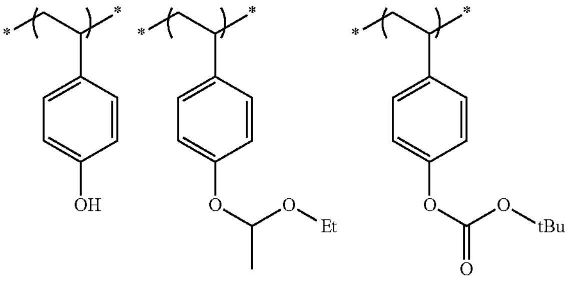

-continued
(R-3)
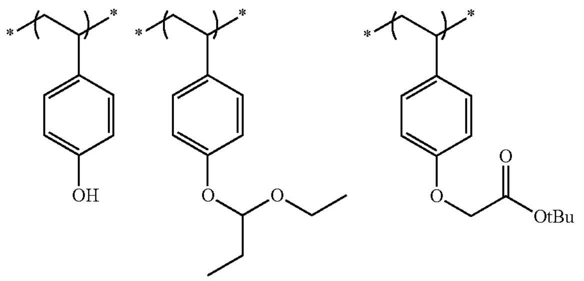
(R-4)
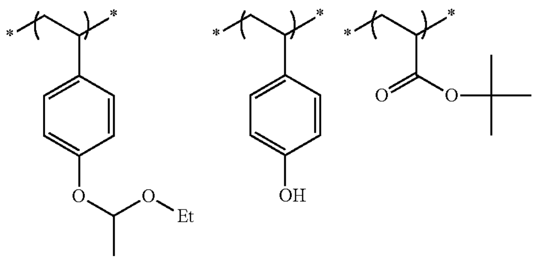
(R-5)
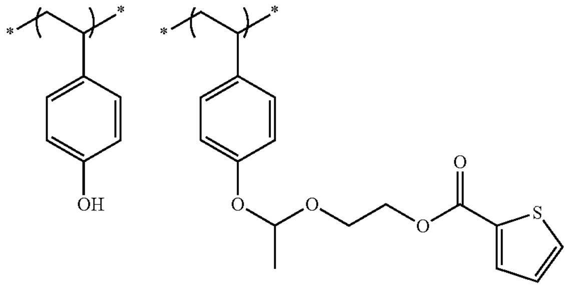
(R-6)
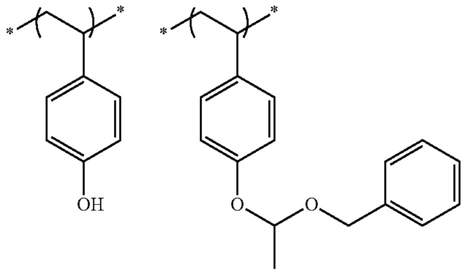
(R-7)
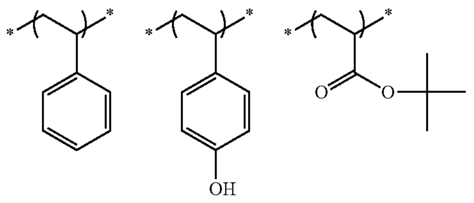
(R-8)
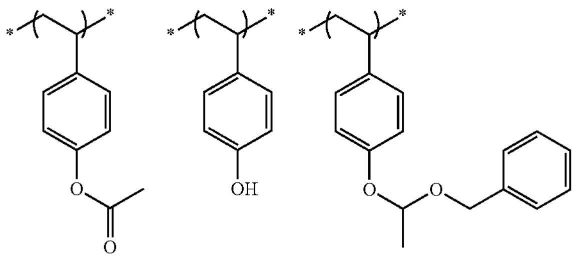
(R-9)
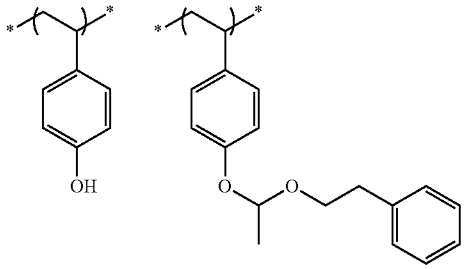
(R-10)
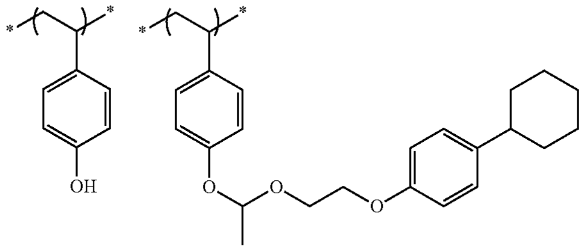

-continued
(R-11)
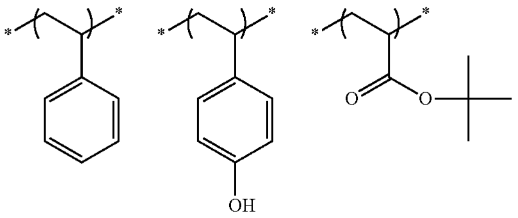
(R-12)
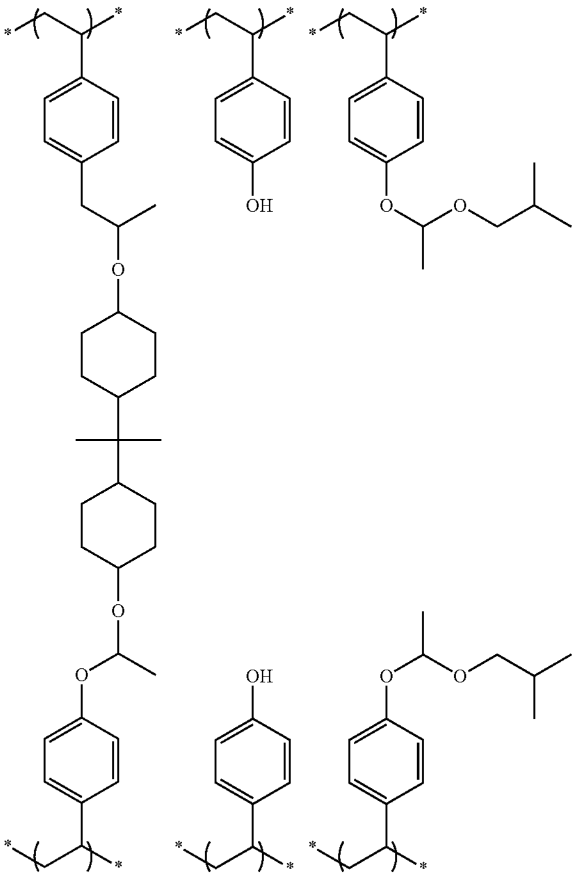
(R-13)
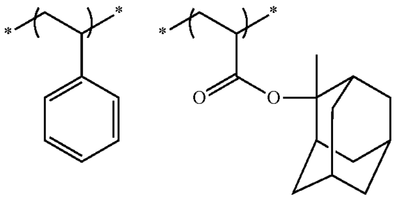
(R-14)
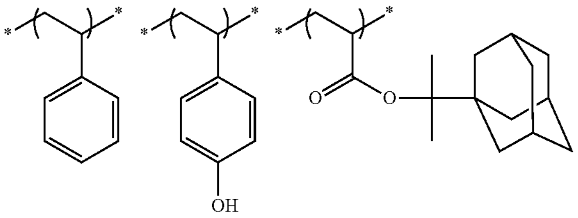
(R-15)
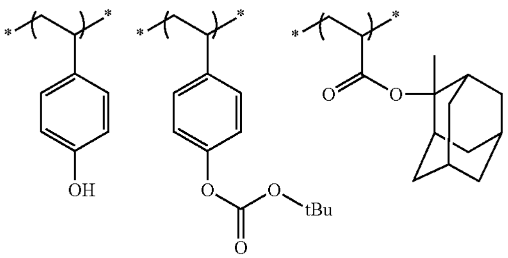
(R-16)
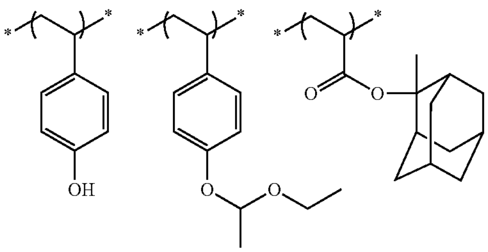

-continued
(R-17)
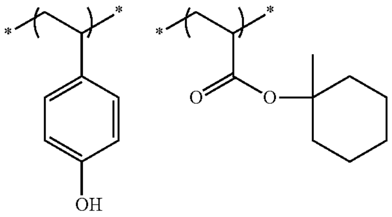
(R-18)
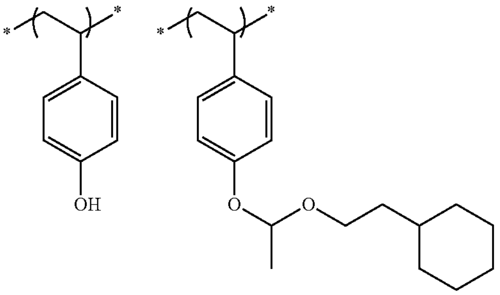
(R-19)
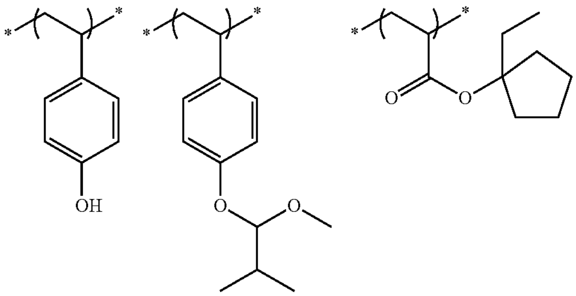
(R-20)
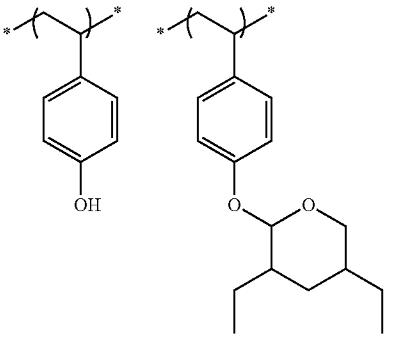
(R-21)
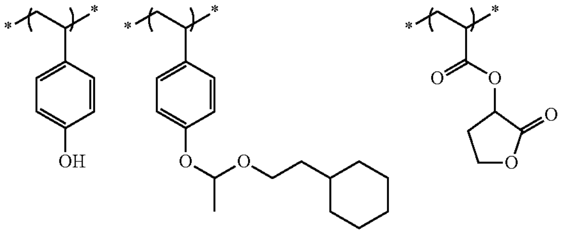
R-22
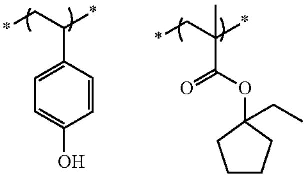
R-23
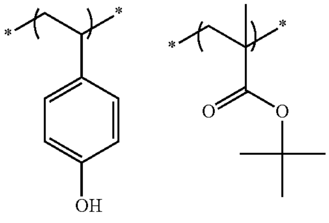
R-24
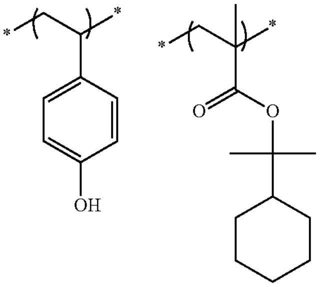
R-25
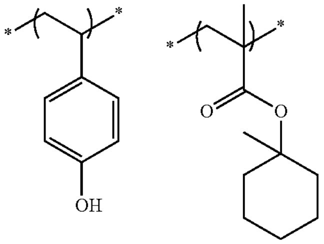
R-26
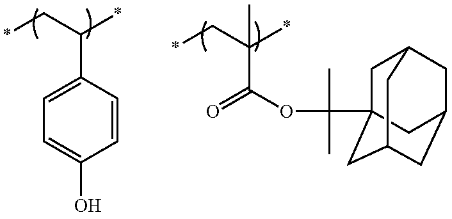

-continued
R-27
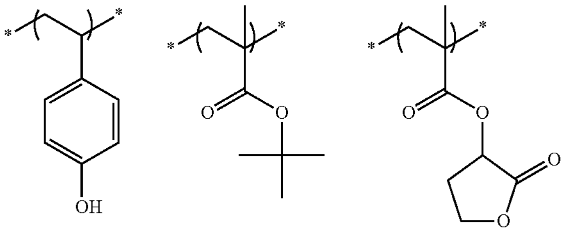
R-28
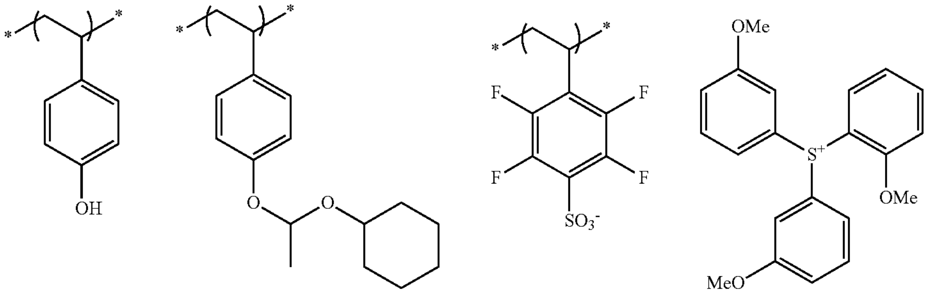
R-29
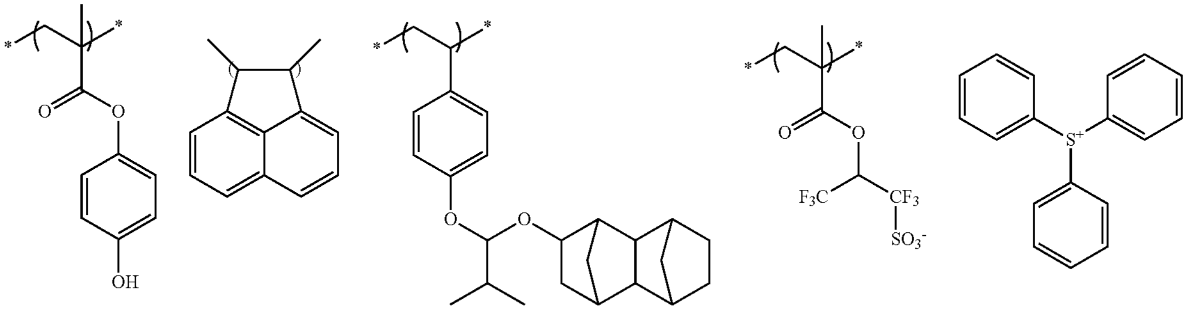
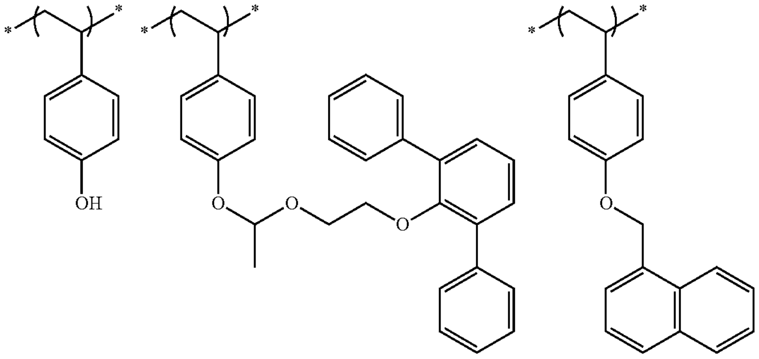
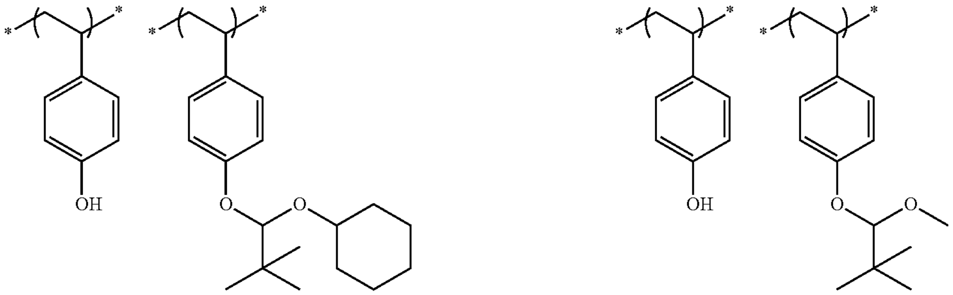

-continued
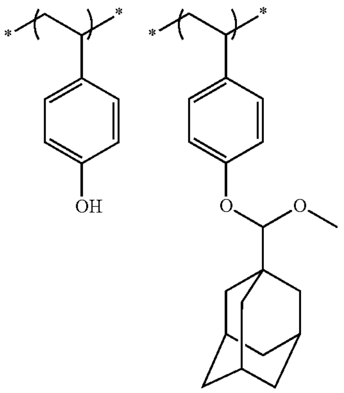
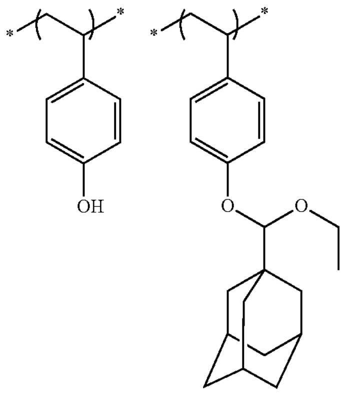
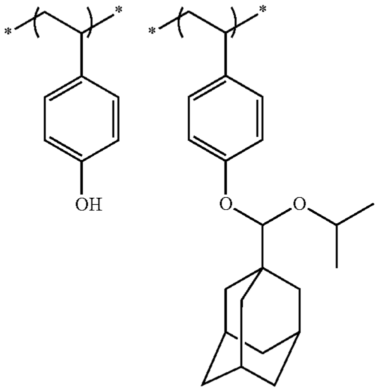
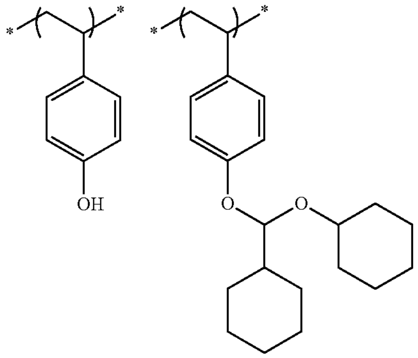
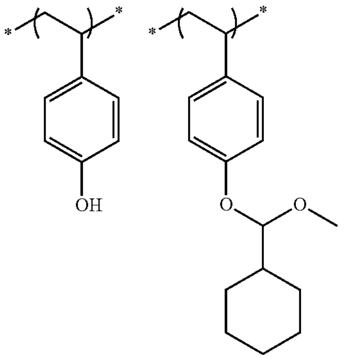
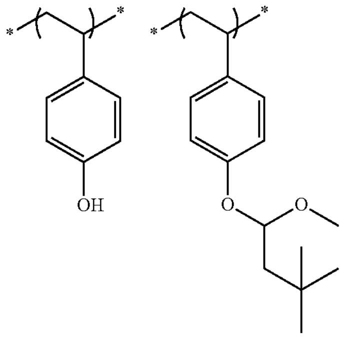
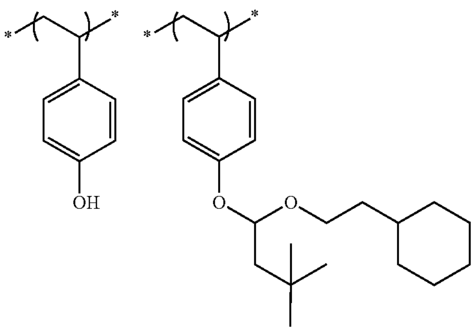
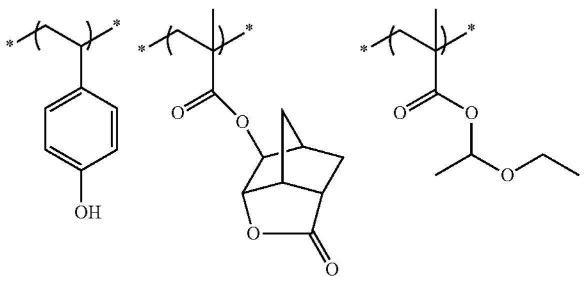

-continued
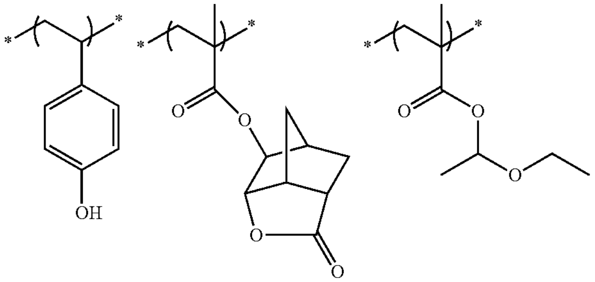
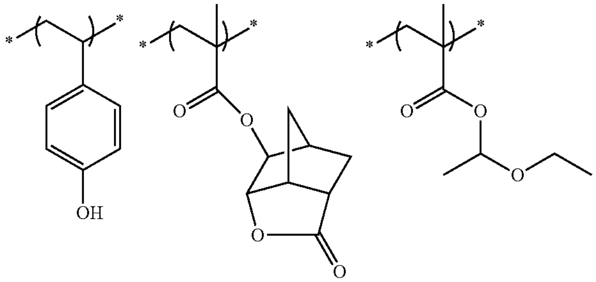
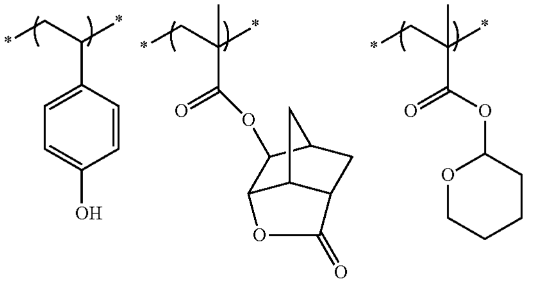
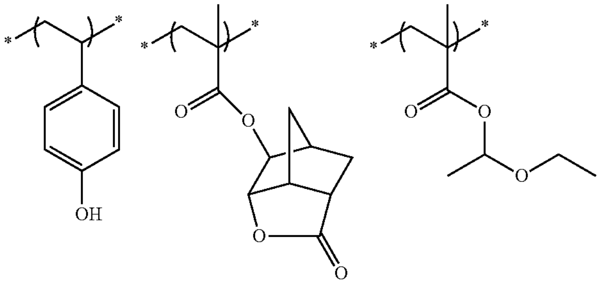
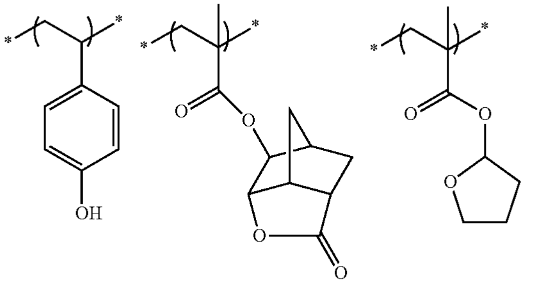
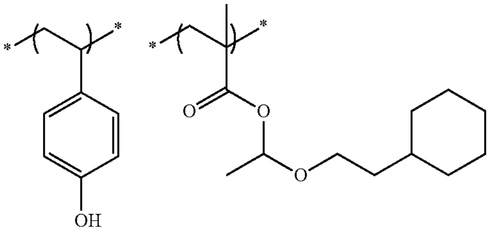
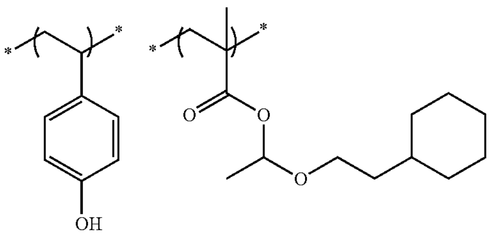
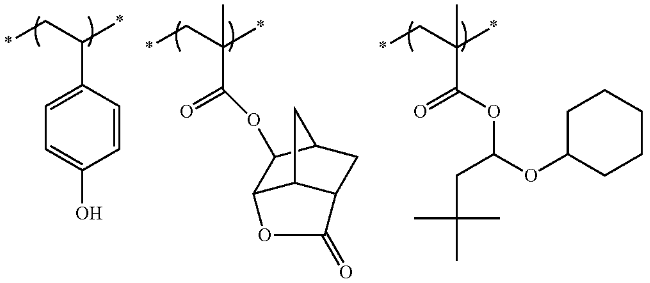
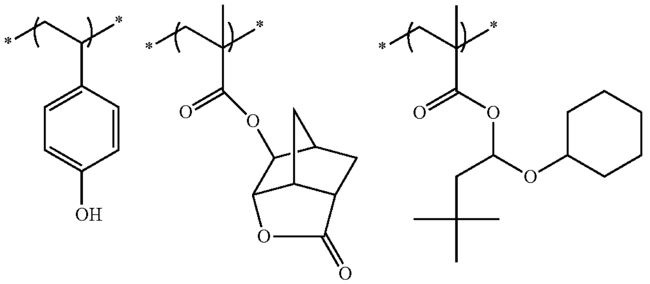
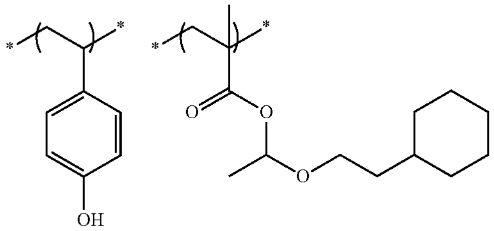
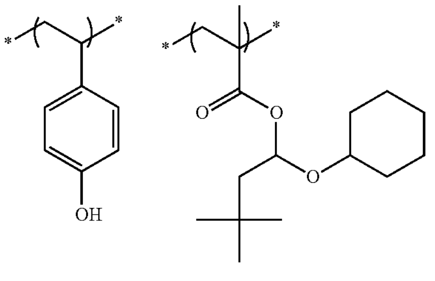
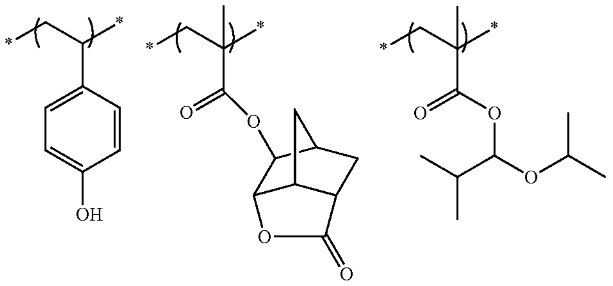

-continued
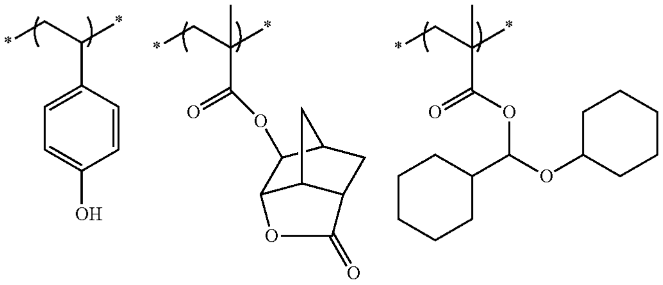
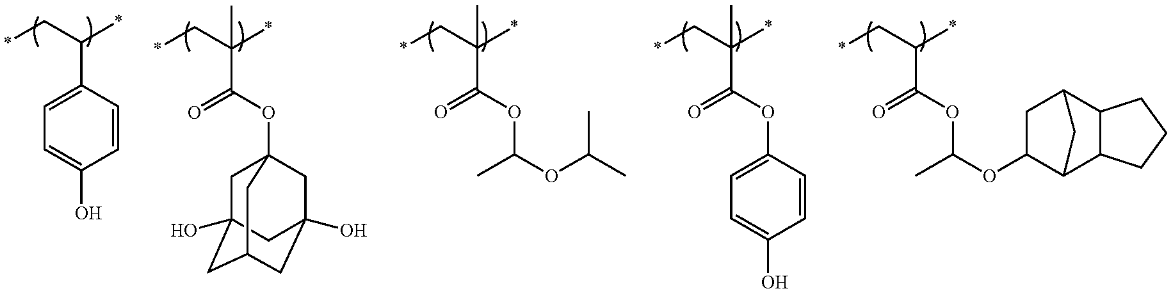
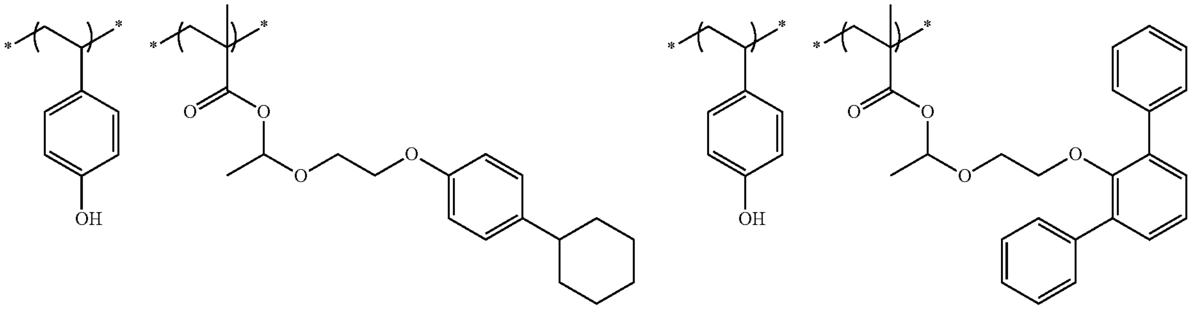
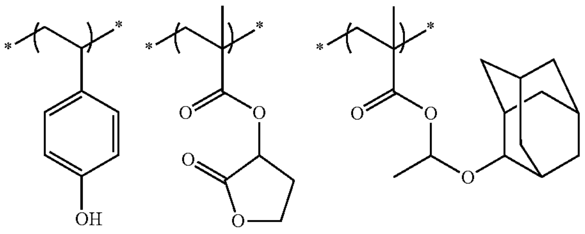
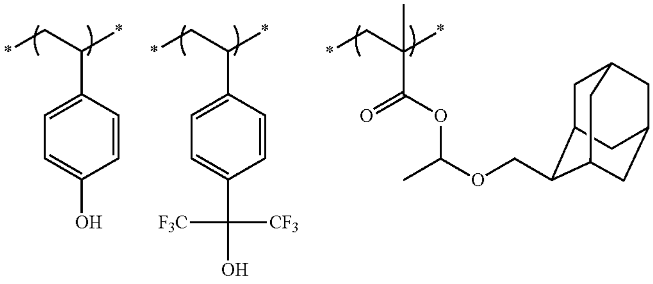
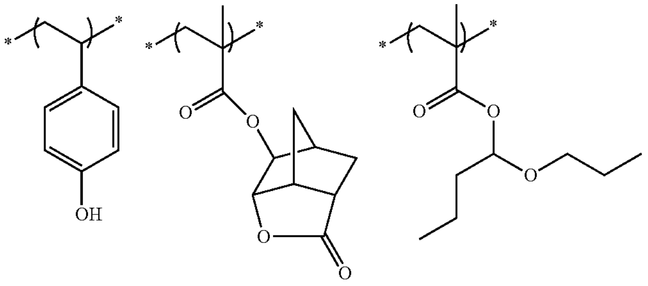

-continued
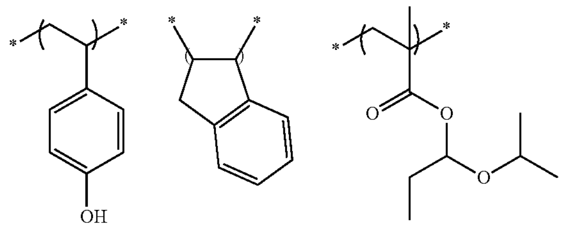
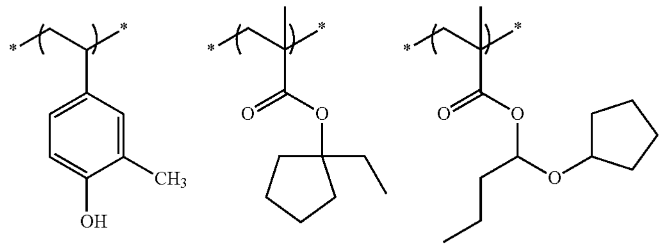
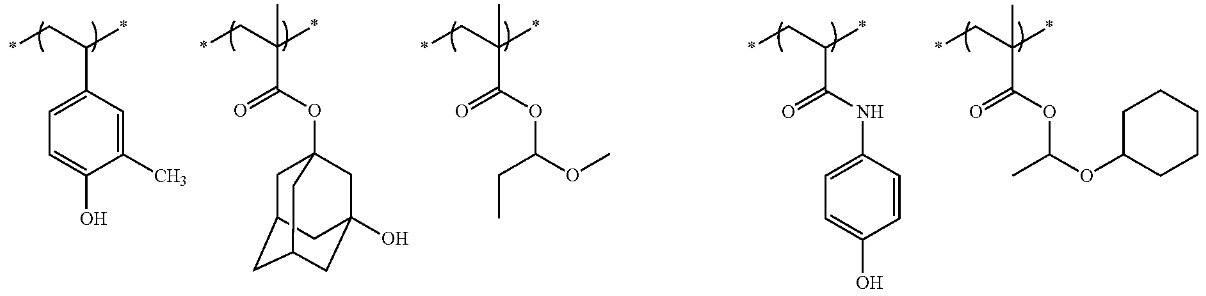
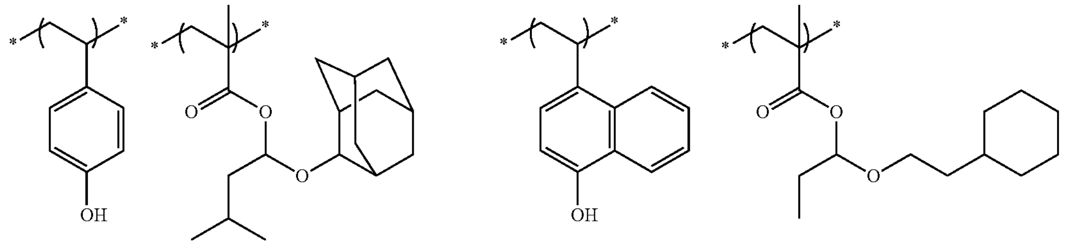
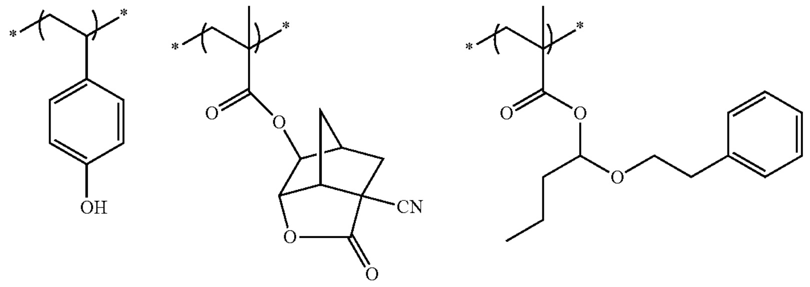
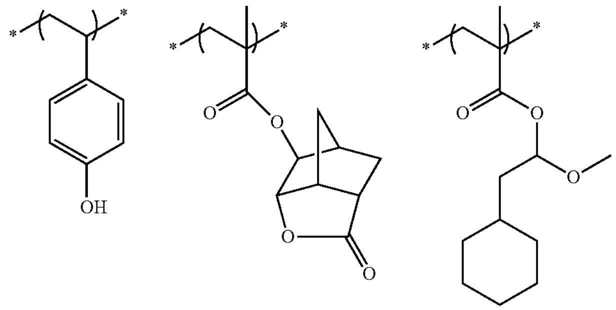

-continued
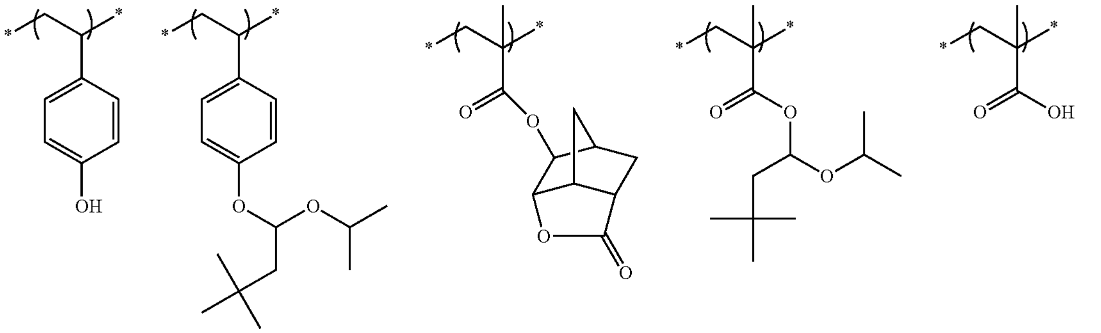
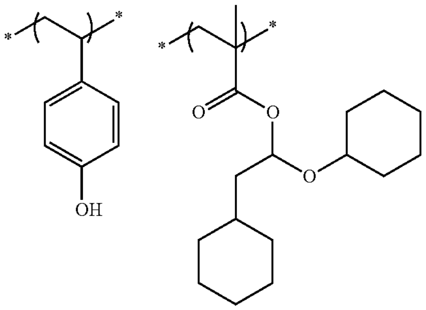
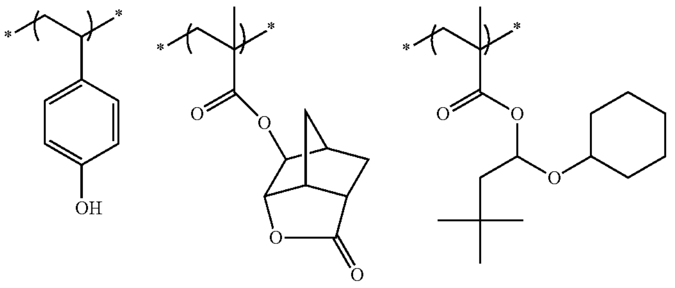
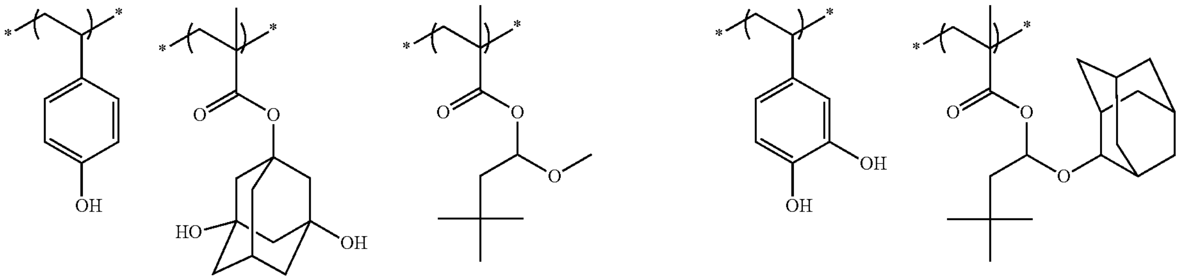
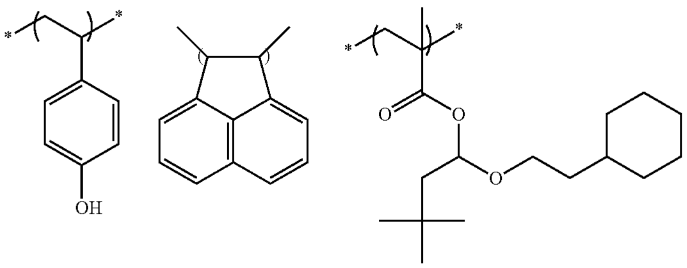

-continued
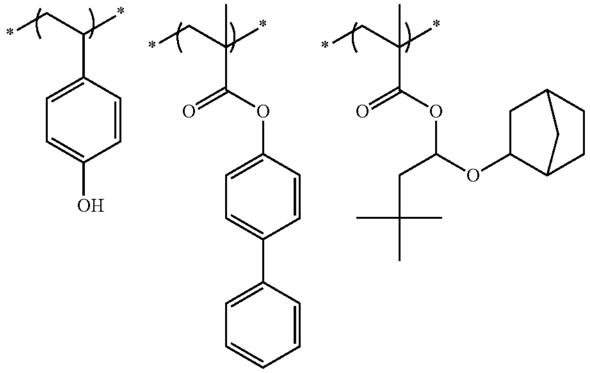
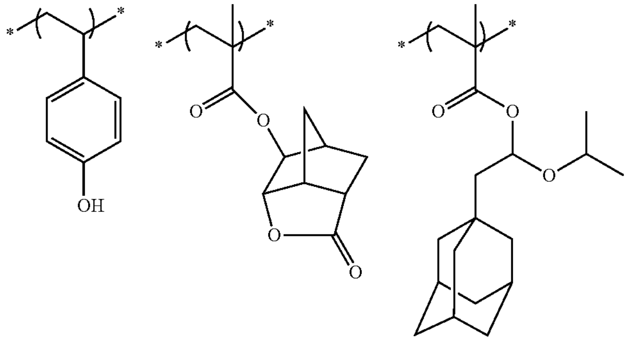
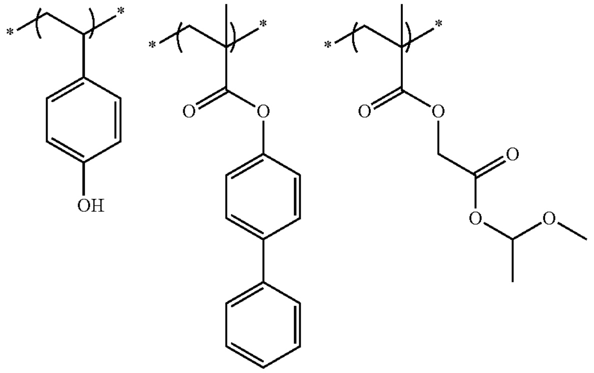
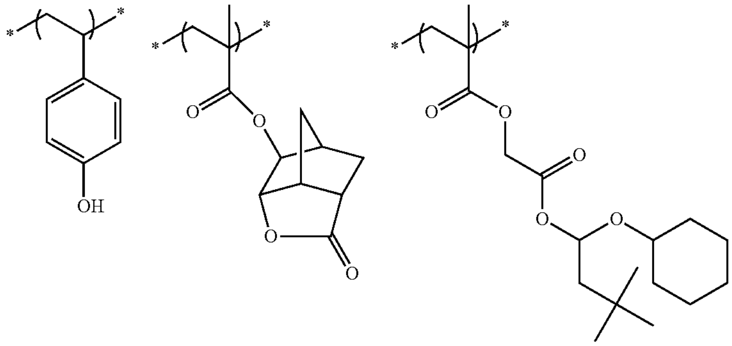
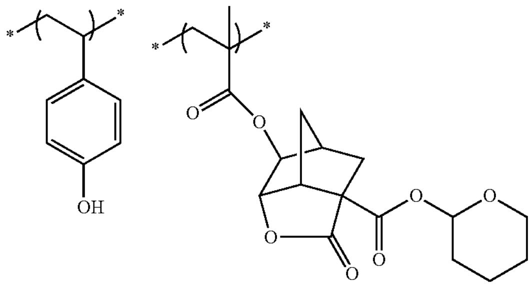

-continued
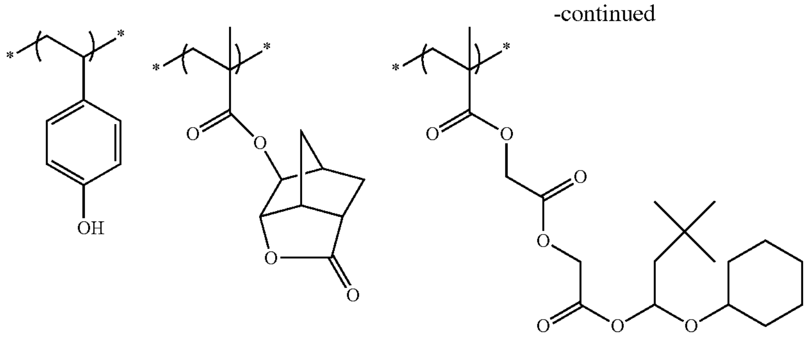
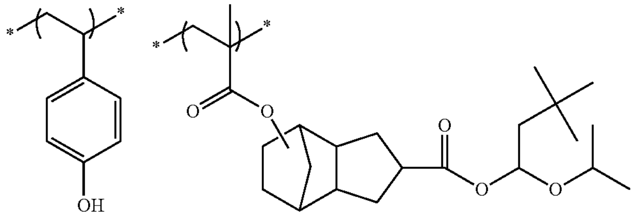
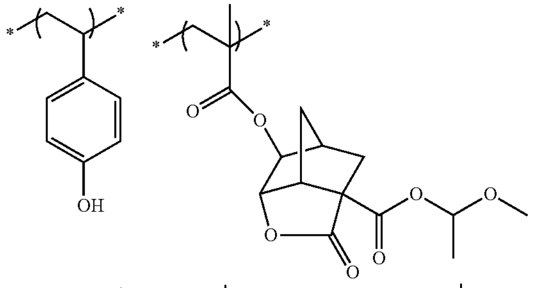
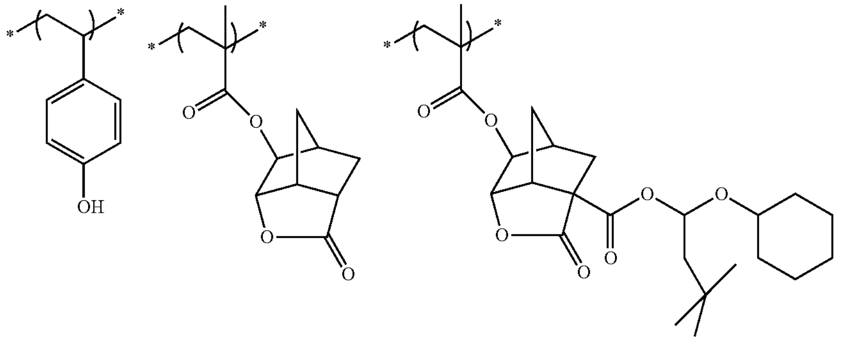
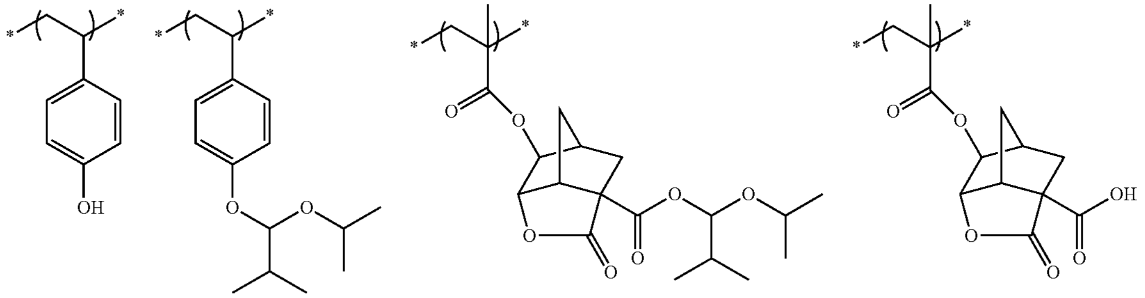
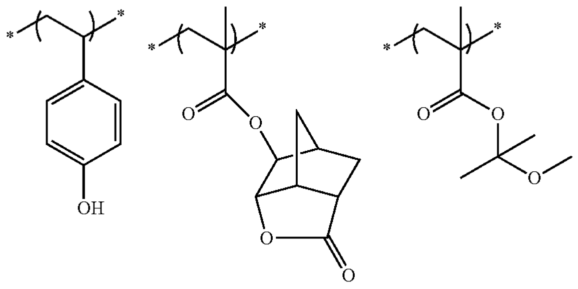

-continued
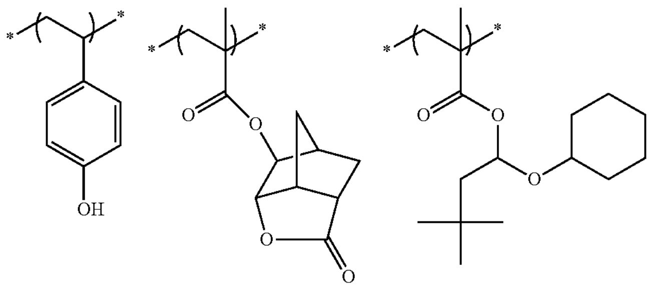
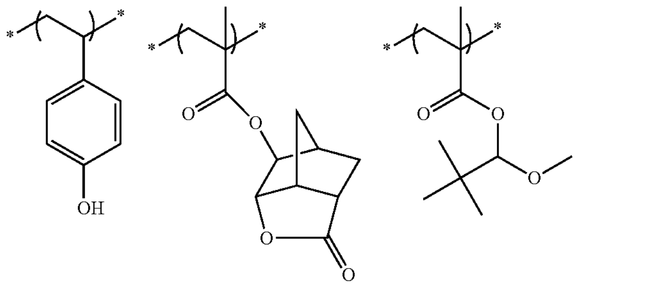
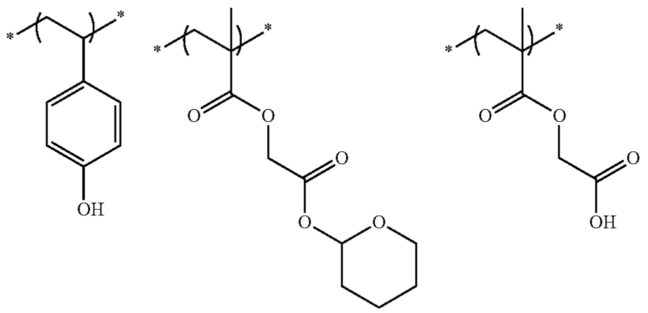
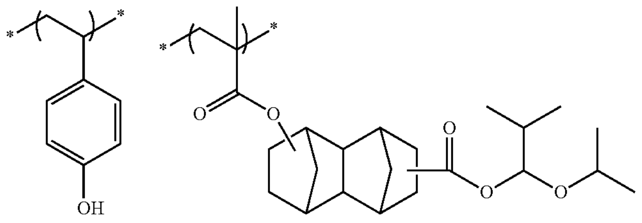
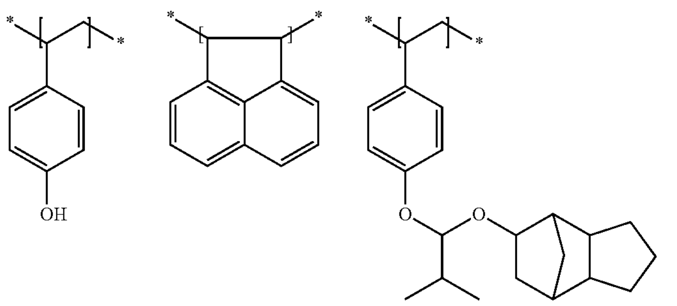
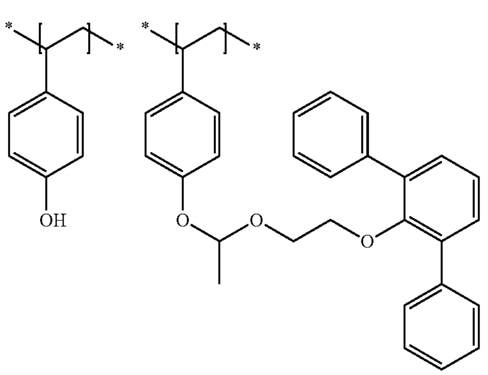

-continued
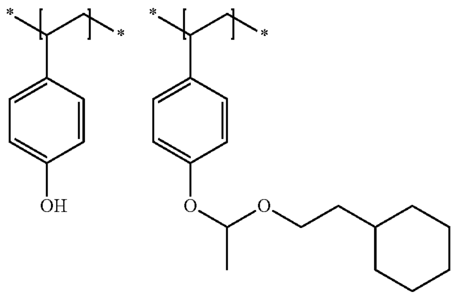
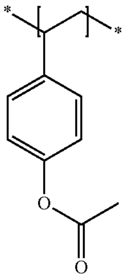
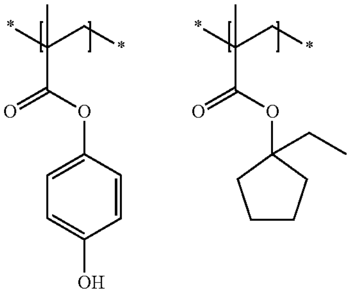
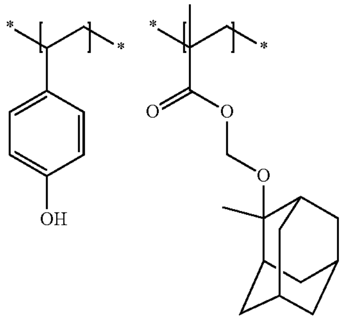
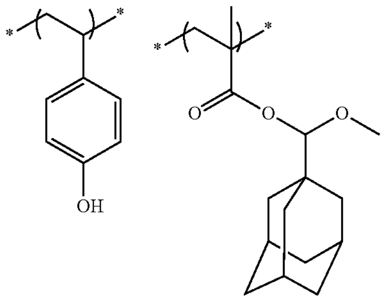
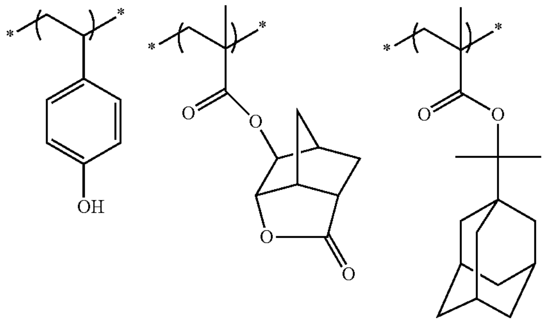
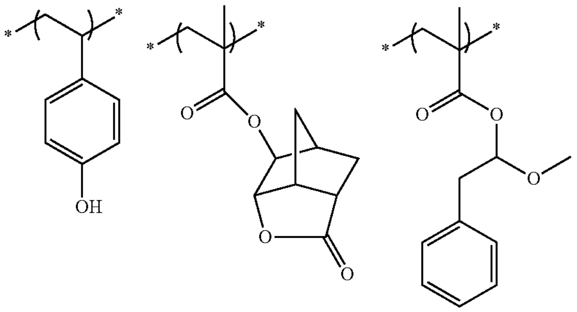
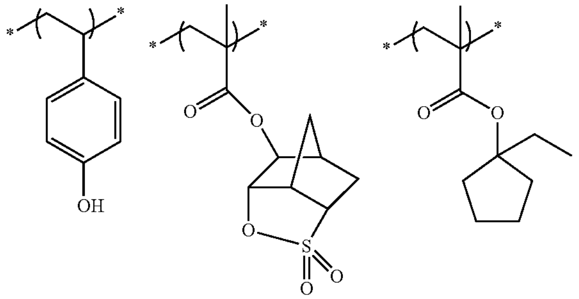
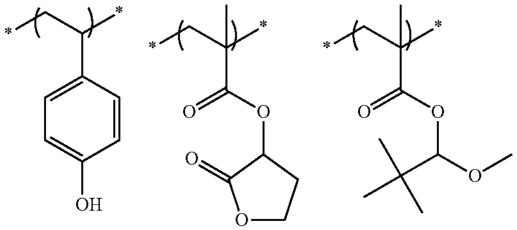

-continued

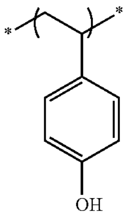
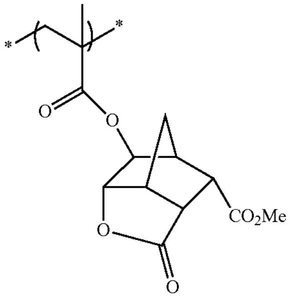
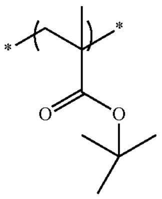
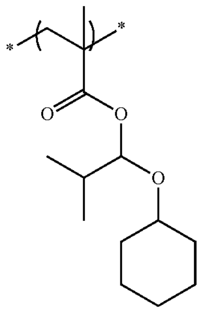

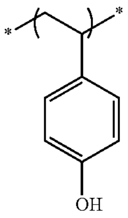
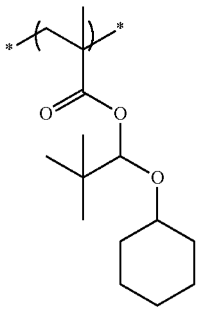
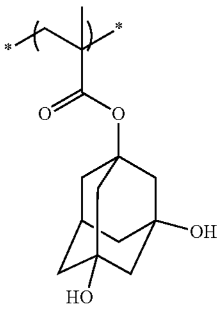

In the specific examples described above, tBu represents a t-butyl group.

The content of the groups able to be decomposed by acid is calculated by the expression B/(B+S) using the number (B) of groups which are able to be decomposed by acid in the resin and the number (S) of alkali-soluble groups not protected by a group which is released by acid. This content ratio is preferably 0.01 to 0.7, more preferably 0.05 to 0.50, and even more preferably 0.05 to 0.40.

The compound (B) may have a monocyclic or polycyclic alicyclic hydrocarbon structure.

The compound (B) may have a repeating unit which includes at least one group which is selected from a lactone group and a sultone group. The lactone group is preferably a group which has a 5- to 7-membered ring lactone structure, and particularly preferably a lactone group in which another ring structure is condensed in a form which forms a bicyclo structure or a spiro structure in the 5- to 7-membered ring lactone structure.

Here, in the repeating unit which has a lactone structure, normally, an optical isomer is present and any optical isomer may be used. In addition, one type of optical isomer may be used alone, or a plurality of optical isomers may be used in a mixture. In a case of primarily using one type of optical isomer, the optical purity thereof is preferably 90% ee or more, and more preferably 95% ee or more.

Particularly preferable examples of a repeating unit which has a lactone group include the following repeating units. The pattern profile and the density dependence are made to be favorable by selecting an optimal lactone group. In the formulae, Rx and R represent H, $CH_3$, $CH_2OH$, or $CF_3$.

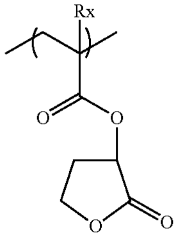
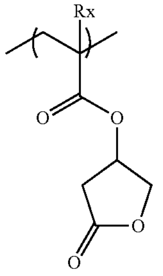
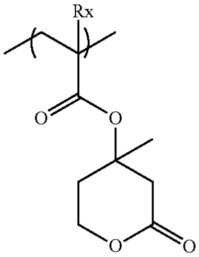
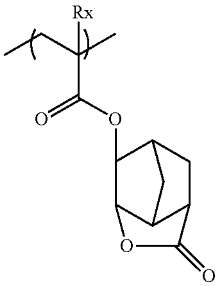
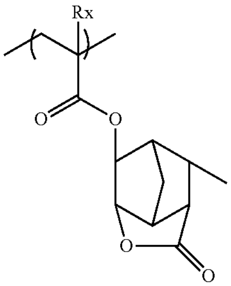
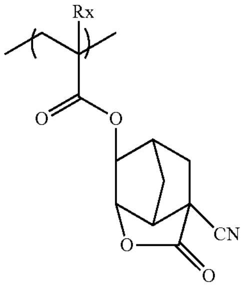
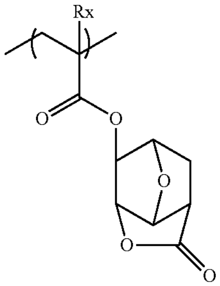

-continued
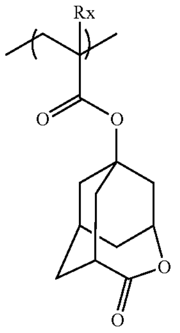
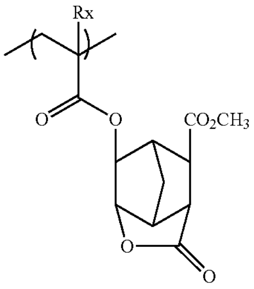
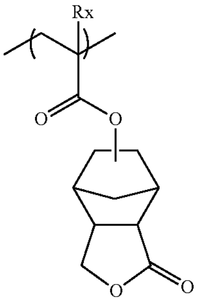
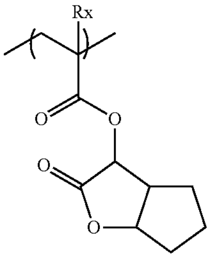
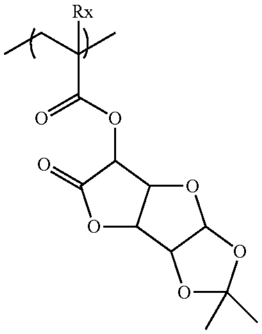
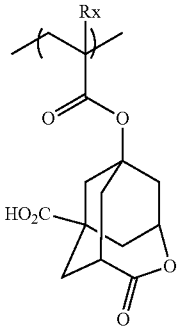
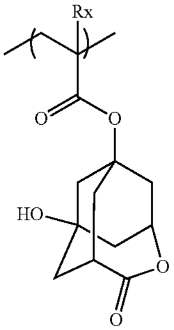
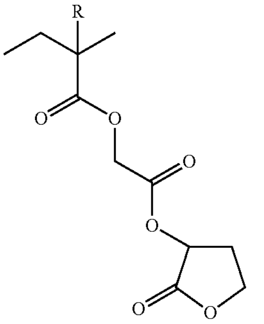
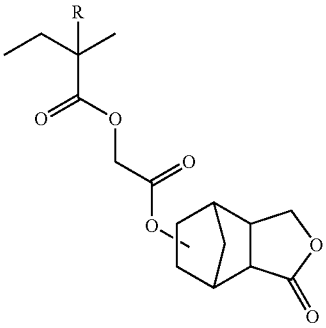
-continued
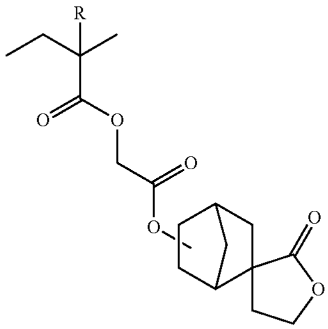
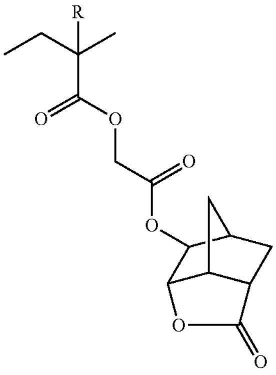
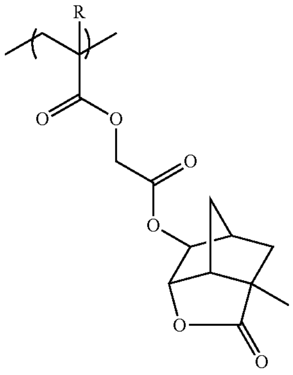
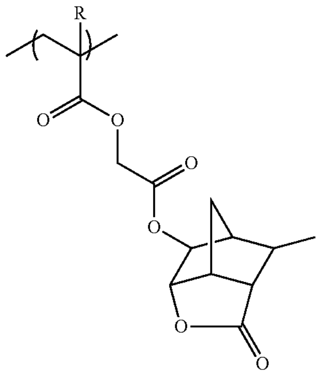
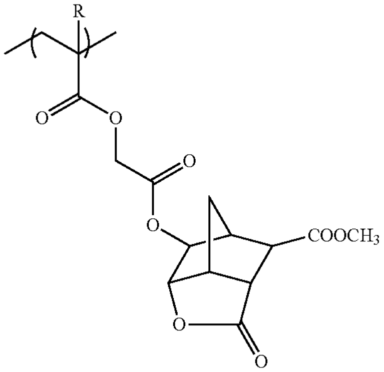

-continued
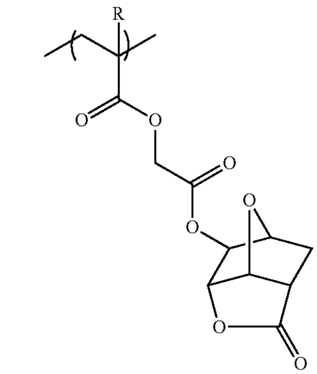
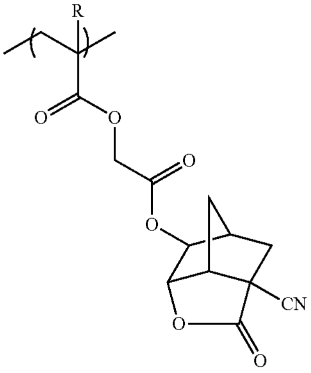
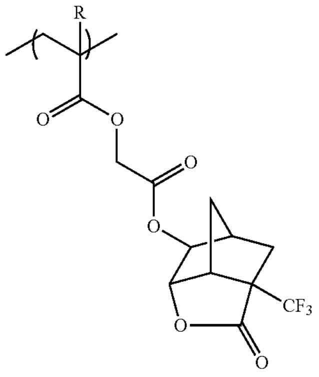
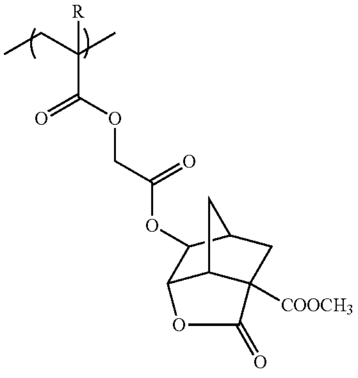
-continued
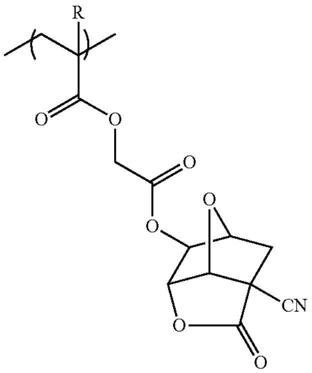
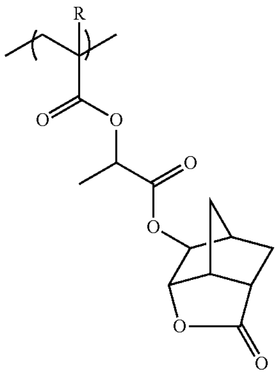
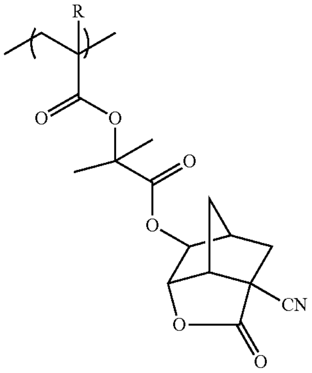
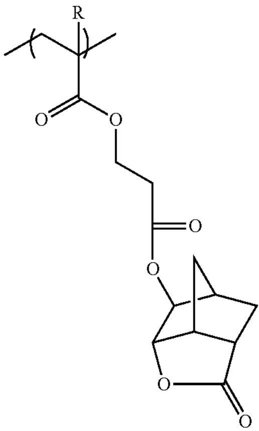
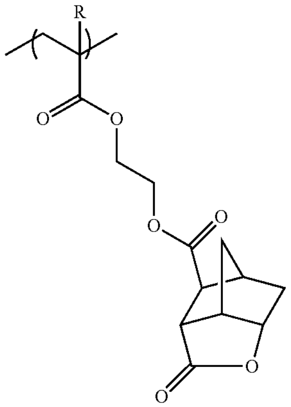

-continued

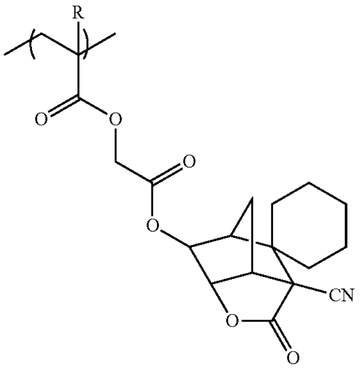

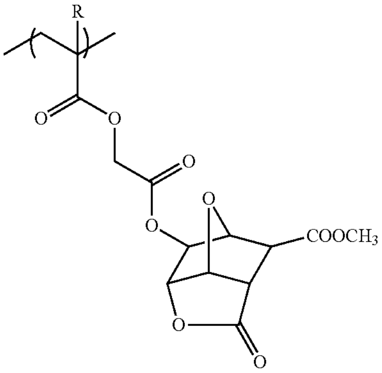

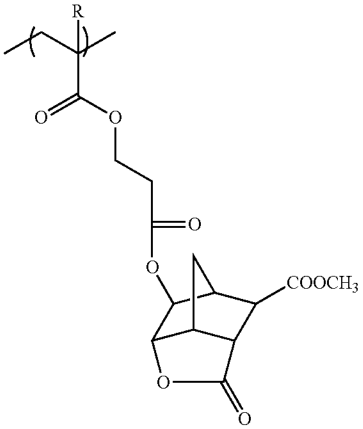

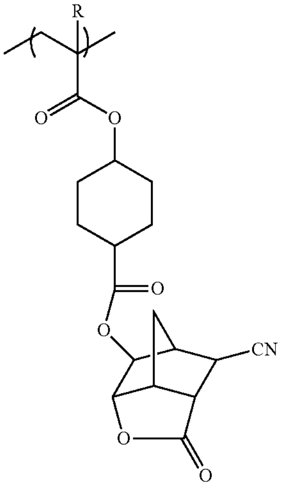

-continued

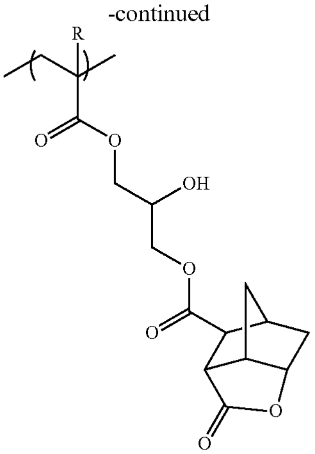

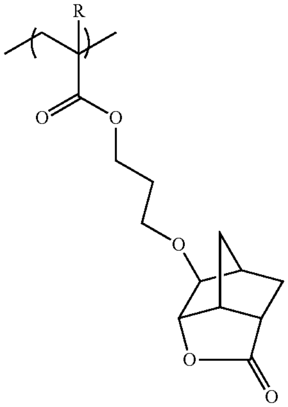

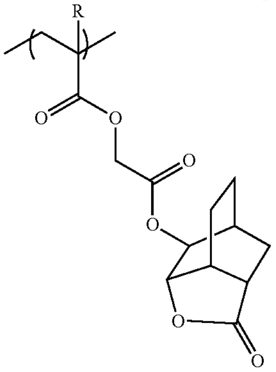

Preferable examples of the repeating unit of the resin also include repeating units in which the lactone group is substituted with a sultone group in the repeating units which have a lactone group described above.

The weight-average molecular weight of the resin which is decomposed by the action of an acid and of which the solubility is increased in the alkali developer is preferably in a range of 2,000 to 200,000 as a polystyrene conversion value determined by a GPC method. It is possible to particularly improve the heat resistance and the dry etching resistance by making the weight-average molecular weight 2,000 or more. By making the weight-average molecular weight 200,000 or less, it is possible to particularly improve the developability and it is also possible to improve the film-forming properties caused by a decrease in the viscosity of the composition.

The molecular weight is more preferably in a range of 1,000 to 200,000, even more preferably in a range of 2,000 to 50,000, and yet more preferably 2,000 to 10,000. In addition, in fine pattern forming using electron beams, X-rays, or high-energy beams with a wavelength of 50 nm or less (for example, EUV), the weight-average molecular weight is most preferably in a range of 3,000 to 6,000. By adjusting the molecular weight, it is possible to improve the heat resistance and resolving power of the composition, to reduce development defects, and the like at the same time.

The molecular weight of the compound (B) as a relatively low-molecular-weight compound such as a molecular resist is preferably 3,000 or less, more preferably 300 to 2,000, and even more preferably 500 to 1,500.

The dispersity (Mw/Mn) of the resin which is decomposed due to the action of an acid and of which the solubility in an alkali developer is increased is preferably 1.0 to 3.0, more preferably 1.0 to 2.5, and even more preferably 1.0 to 1.6. By adjusting the dispersity, for example, it is possible to improve the line edge roughness performance.

The blending ratio of the resin in the composition according to the present invention is preferably 30 mass % to 99.9 mass %, more preferably 50 mass % to 99 mass %, and even more preferably 60 mass % to 99 mass %, based on the total solid content.

In a case where the composition of the present invention is irradiated with ArF excimer laser light, the content ratio of the compound (B) in the total solid content is preferably 0 mass % to 30 mass %, more preferably 0 mass % to 10 mass %, and even more preferably 0 mass % to 5 mass %. Due to this, the transparency of the resist film with respect to ArF light is improved.

In a case where the composition of the present invention is irradiated with ArF excimer light, the composition preferably includes an acid-decomposable resin. Examples of typical acid-decomposable resins include the acid-decomposable resins described in paragraphs "0118" to "0206" in JP2014-6491A. The content ratio of the acid-decomposable resin in the total solid content is preferably 50 mass % to 99 mass %, more preferably 60 mass % to 98 mass %, and even more preferably 70 mass % to 95 mass %.

[3] Acid Cross-Linkable Compound (C)

The active light sensitive or radiation sensitive resin composition of the present invention may contain an acid cross-linkable compound (C). In a case where the active light sensitive or radiation sensitive resin composition of the present invention is used as a negative type active light sensitive or radiation sensitive resin composition, a compound (referred to below as an acid cross-linking agent or simply as a cross-linking agent as appropriate) which has two or more hydroxymethyl groups or alkoxymethyl groups in the molecule is preferably contained as the acid cross-linkable compound (C).

Examples of preferable cross-linking agents include hydroxymethylated or alkoxymethylated phenolic compounds, alkoxymethylated melamine-based compounds, alkoxymethyl glycoluril based compounds, and alkoxymethylated urea-based compounds, and, among these, hydroxymethylated or alkoxymethylated phenolic compounds are more preferable since it is possible to obtain a favorable pattern shape. Particularly preferable examples of the compounds (C) as the cross-linking agent include phenolic derivatives including 3 to 5 benzene rings in the molecule, further having two or more hydroxymethyl groups or alkoxymethyl groups in total, and with a molecular weight of 1,200 or less, or melamine formaldehyde derivatives or alkoxymethyl glycoluril derivatives which have at least two free N-alkoxymethyl groups.

The active light sensitive or radiation sensitive resin composition of the present invention more preferably contains at least two types of compounds which have two or more alkoxymethyl groups in the molecule as the acid cross-linkable compound (C) from the point of view of the pattern shape, and even more preferably contains at least two types of phenolic compounds which have two or more alkoxymethyl groups in the molecule, and at least one type of the at least two types of phenolic compound is particularly preferably a phenolic derivative including 3 to 5 benzene rings in the molecule, further having two or more alkoxymethyl groups in total, and with a molecular weight of 1,200 or less.

As the alkoxymethyl group, a methoxymethyl group or an ethoxy methyl group is preferable.

Among the cross-linking agents described above, it is possible to obtain the phenolic derivatives having a hydroxymethyl group by reacting a phenolic compound which does not have a corresponding hydroxymethyl group with formaldehyde in the presence of a base catalyst. In addition, it is possible to obtain a phenolic derivative which has an alkoxymethyl group by reacting a phenolic derivative which has a corresponding hydroxymethyl group with alcohol in the presence of an acid catalyst.

In this manner, among the synthesized phenolic derivatives, a phenolic derivative which has an alkoxymethyl group is particularly preferable from the point of view of sensitivity and storage stability.

Other preferable examples of cross-linking agents further include compounds which have an N-hydroxymethyl group or an N-alkoxymethyl group such as alkoxymethylated melamine-based compounds, alkoxymethyl glycoluril-based compounds, and alkoxymethylated urea-based compounds.

Examples of such compounds include hexamethoxymethyl melamine, hexaethoxymethyl melamine, tetramethoxy methyl glycoluril, 1,3-bismethoxymethyl-4,5-bismethoxy ethylene urea, bismethoxymethyl urea, and the like as described in EP0133216A, DE3634671B, DE3711264B, and EP0212482A.

Particularly preferable examples of these cross-linking agents include the following.

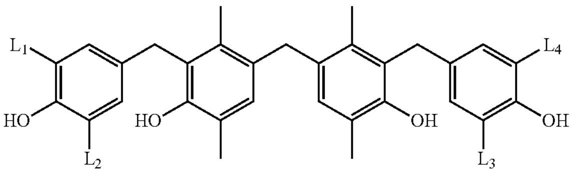

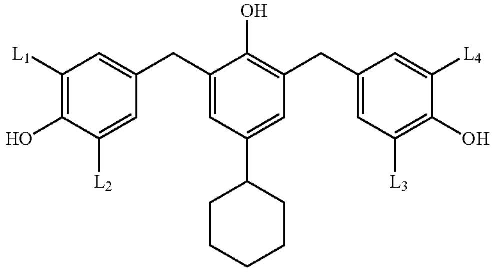

-continued

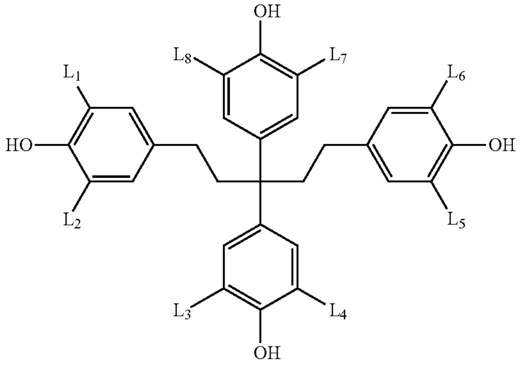

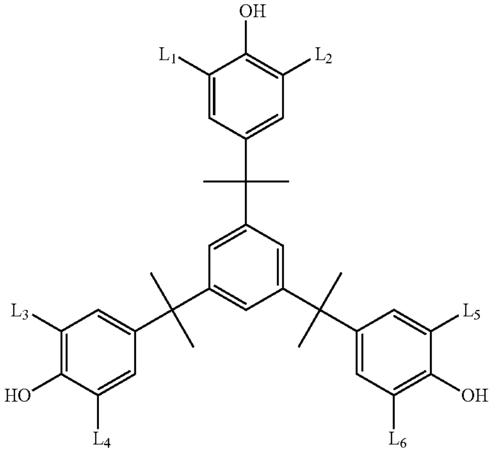

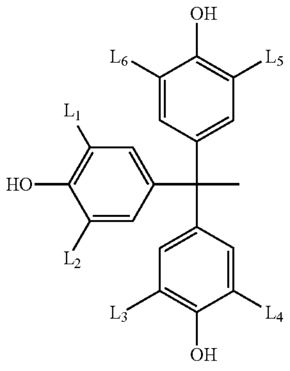

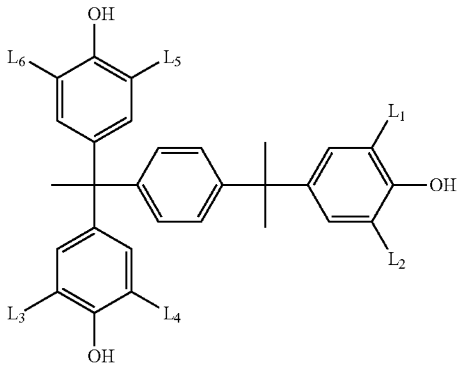

-continued

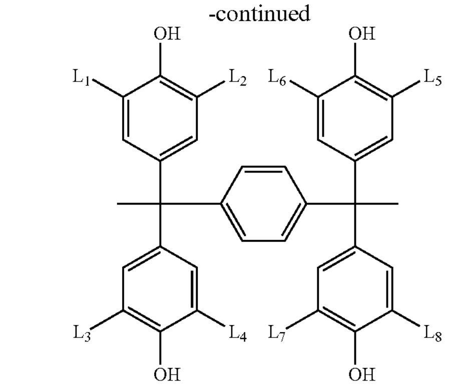

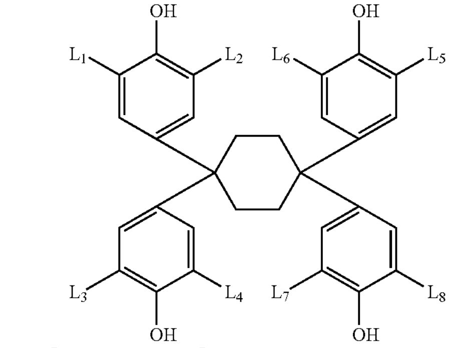

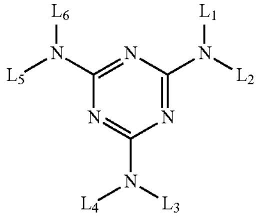

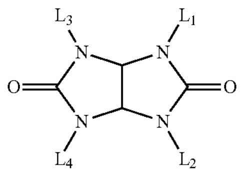

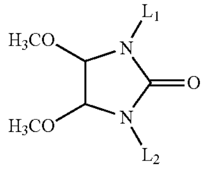

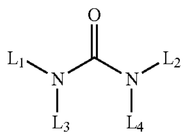

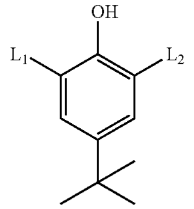

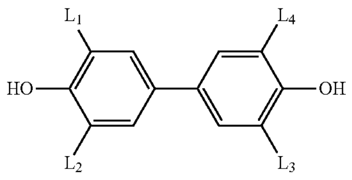

In the formulae, $L_1$ to $L_8$ each independently represent a hydrogen atom, a hydroxymethyl group, a methoxymethyl group, an ethoxymethyl group, or an alkyl group having 1 to 6 carbon atoms.

The cross-linking agent in the present invention is used with an added amount of preferably 3 mass % to 65 mass %, and more preferably 5 mass % to 50 mass %, in the solid content of the active light sensitive or radiation sensitive resin composition.

By setting the added amount of the cross-linking agent to 3 mass % to 65 mass %, it is possible to prevent decreases in the residual film ratio and resolving power and to favorably preserve the stability of the resist solution during storage.

In the present invention, the cross-linking agent may be used alone, or may be used as a combination of two or more agents, and is preferably used as a combination of two or more agents from the point of view of the pattern shape.

For example, in a case where another cross-linking agent, for example, a compound or the like which has an N-alkoxymethyl groups described above, is also used in addition to the phenolic derivative described above, the ratio of the phenolic derivative described above and the other cross-linking agent is 100/0 to 20/80, preferably 90/10 to 40/60, and even more preferably 80/20 to 50/50 in a molar ratio.

The acid cross-linkable compound (C) may be a resin which has a repeating unit having an acid-cross-linkable group (also referred to below as resin (C")). In a case where the acid cross-linkable compound (C) is the resin (C") described above, since the repeating unit in the resin (C") described above has an acid-cross-linkable group, it is possible to form a hard film with a higher cross-linking reactivity in comparison with the active light sensitive or radiation sensitive resin composition which contains a resin which does not have a repeating unit having an acid-cross-linkable group. As a result, it is considered that the dry etching resistance is improved. In addition, since the diffusion of the acid in the sections exposed to active light or radiation is suppressed, it is considered that, as a result, in a case of forming a fine pattern, the resolving power is improved, the pattern shape is improved, and the line edge roughness (LER) is further reduced. In addition, as in the repeating unit represented by General Formula (1) below, in a case where the reaction point of the resin and the reaction point of the cross-linkable group are close, it is considered that the sensitivity of the active light sensitive or radiation sensitive resin composition is improved.

Examples of the resin (C') include a resin which has the repeating unit represented by General Formula (1) below. The repeating unit represented by General Formula (1) is a structure including at least one methylol group which may have a substituent group.

Here, the "methylol group" is a group represented by General Formula (M) below and is preferably a hydroxymethyl group or an alkoxymethyl group in an aspect of the present invention.

(M)

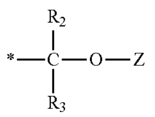

$R_2$ and $R_3$ represent a hydrogen atom, an alkyl group, or a cycloalkyl group.

Z represents a hydrogen atom or a substituent group.

Description will be given below of General Formula (1).

(1)

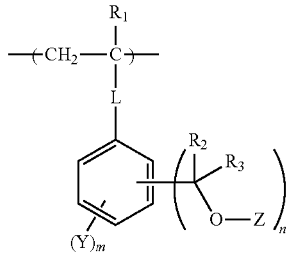

In General Formula (1), $R_2$, $R_3$, and Z are the same as in General Formula (M) described above.

$R_1$ represents a hydrogen atom, a methyl group, or a halogen atom.

L represents a divalent linking group or a single bond.

Y represents a substituent group other than a methylol group.

m represents an integer of 0 to 4.

n represents an integer of 1 to 5.

m+n is 5 or less.

In a case where m is 2 or more, a plurality of Y's may be the same, or may be different from each other.

In a case where n is 2 or more, a plurality of $R_2$'s, $R_3$'s, and Z's may be the same, or may be different from each other.

In addition, two or more of Y, $R_2$, $R_3$, and Z may bond with each other to form a ring structure.

$R^1$, $R_2$, $R_3$, L, and Y may each have a substituent group.

The content ratio of the repeating unit which has an acid-cross-linkable group in the resin (C") is preferably 3 mass % to 40 mass % and more preferably 5 mass % to 30 mass %, with respect to all of the repeating units of the resin (C").

The content of the resin (C") is preferably 5 mass % to 95 mass % and more preferably 10 mass % to 90 mass %, in the total solid content of the negative type resist composition.

The resin (C") may include two or more types of repeating unit having an acid-cross-linkable group, or two or more types of resin (C") may be used in combination. In addition, it is also possible to use the compound (C) and the resin (C") in combination.

Specific examples of the repeating unit which has an acid-cross-linkable group included in the resin (C") include the following structures.

(Q-1)

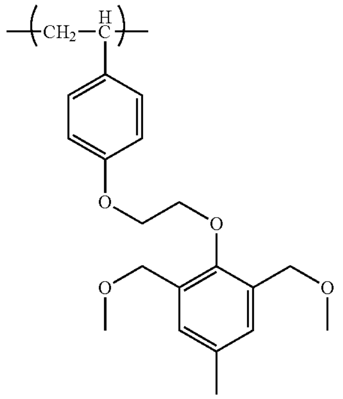

(Q-2)

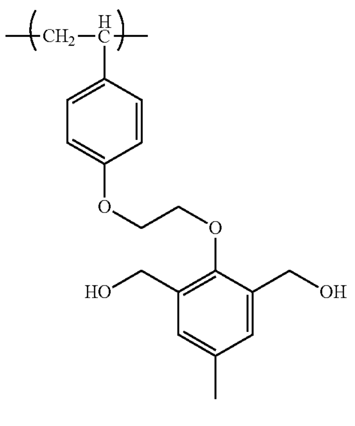

-continued
(Q-3)
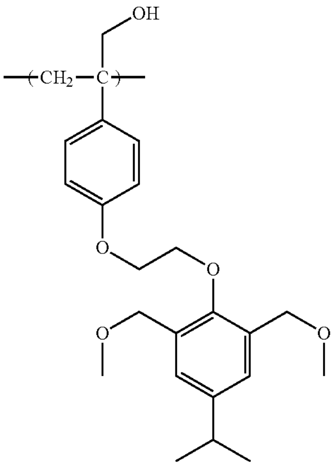
(Q-4)
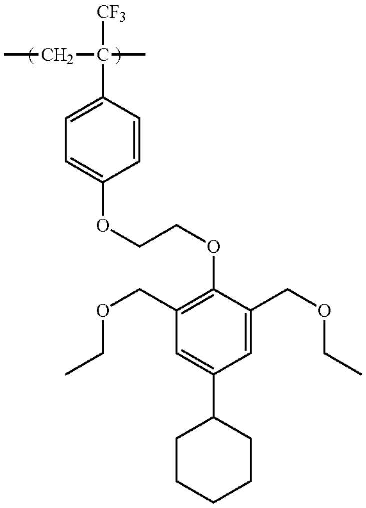
(Q-5)
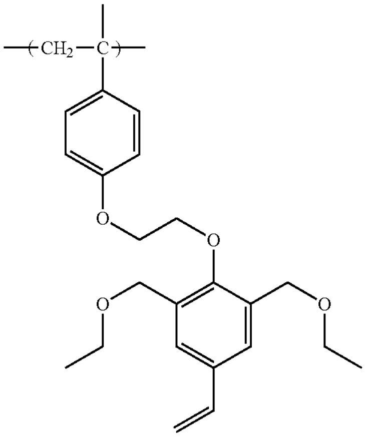
-continued
(Q-6)
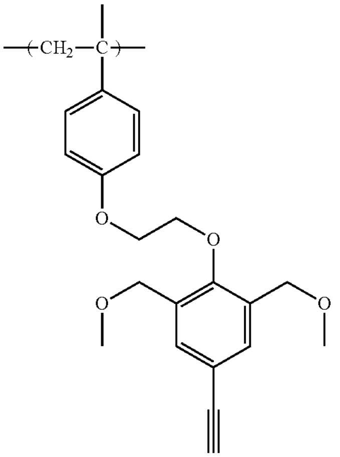
(Q-7)
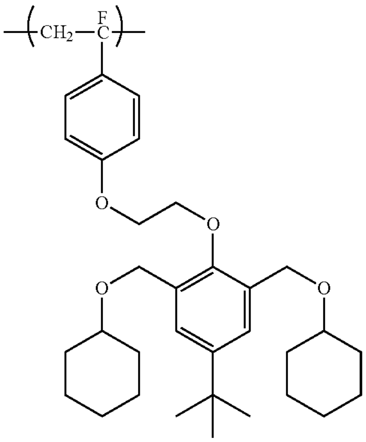
(Q-8)
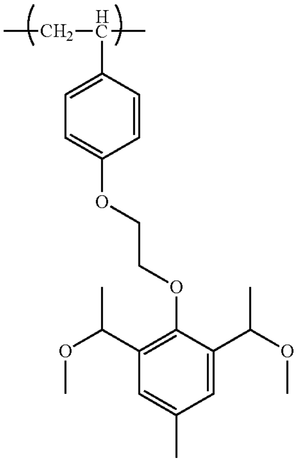

-continued
(Q-9)
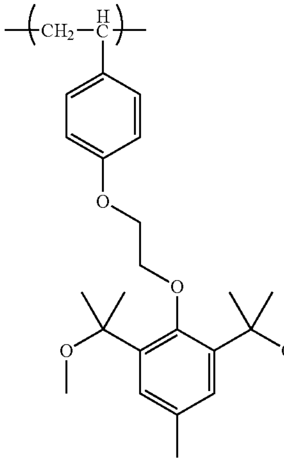
(Q-10)
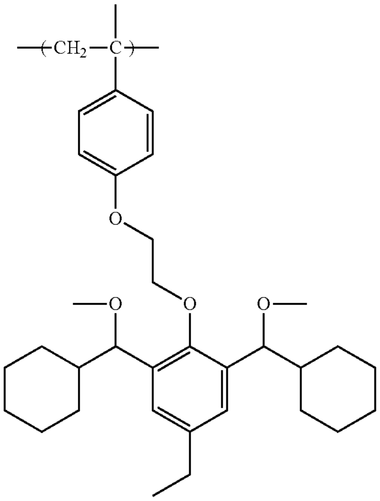
(Q-11)
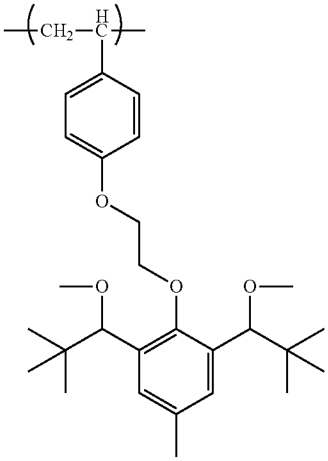
-continued
(Q-12)
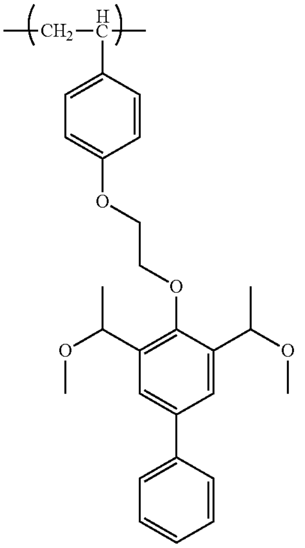
(Q-13)
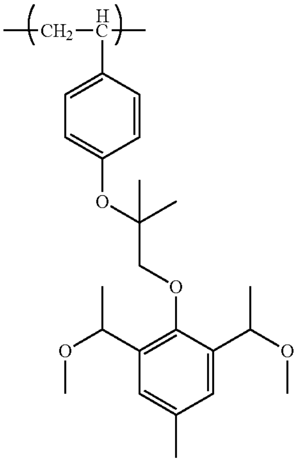
(Q-14)
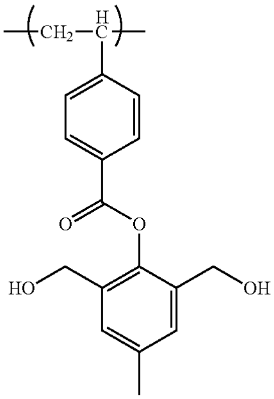

-continued
(Q-15)
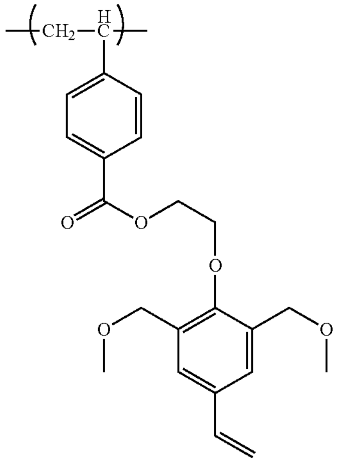
(Q-16)
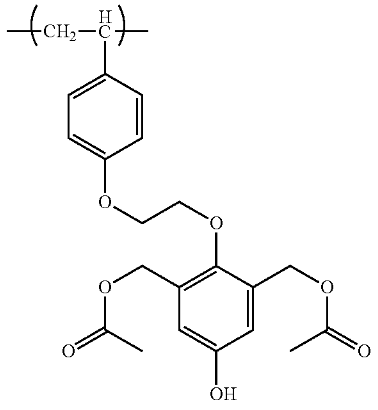
(Q-17)
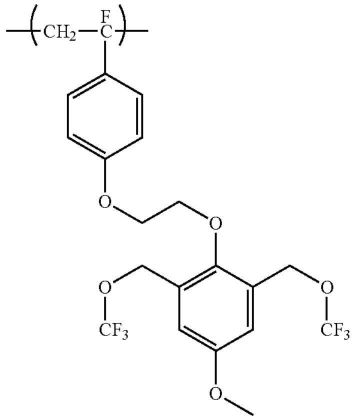
-continued
(Q-18)
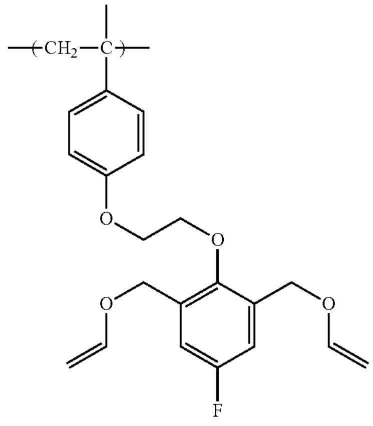
(Q-19)
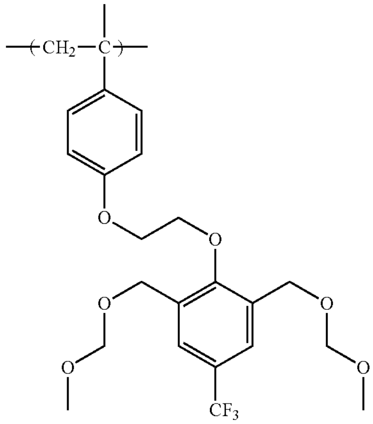
(Q-20)
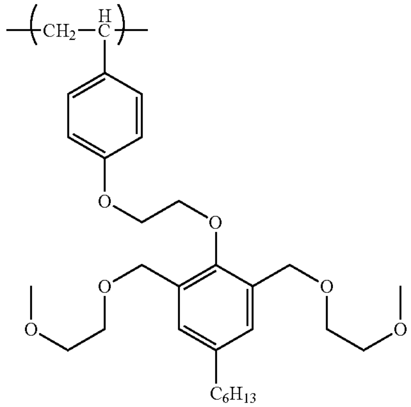

-continued
(Q-21)
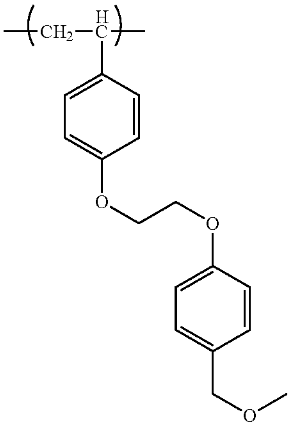
(Q-22)
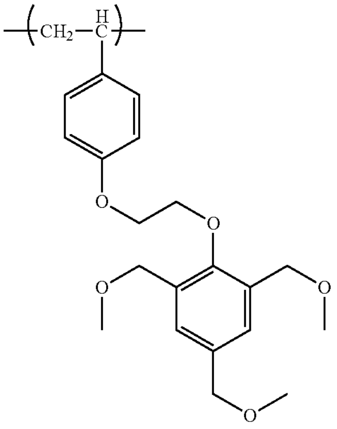
(Q-23)
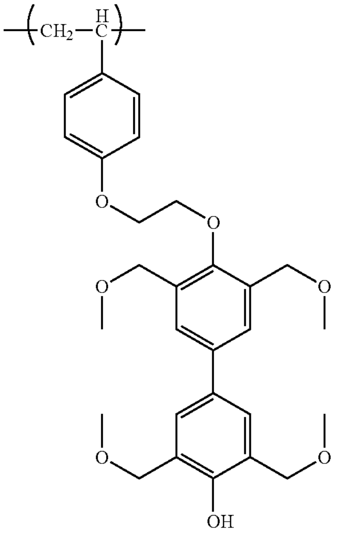
-continued
(Q-24)
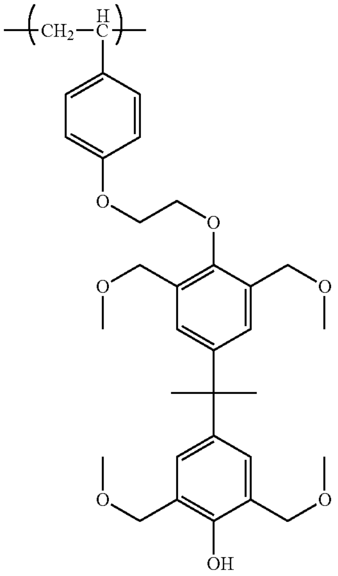
(Q-25)
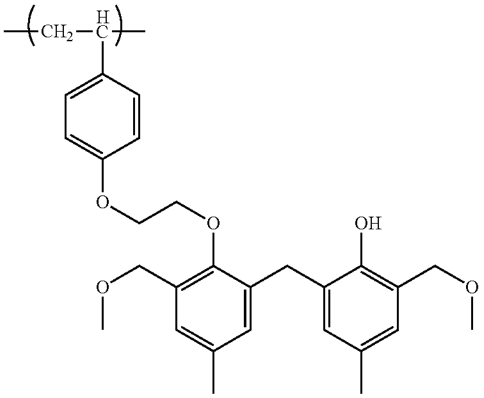
(Q-26)
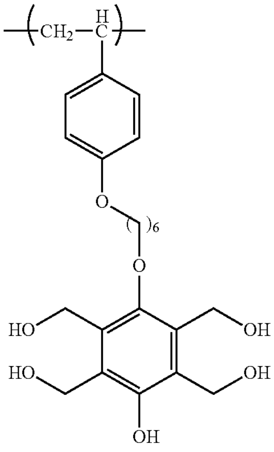

-continued (Q-27)

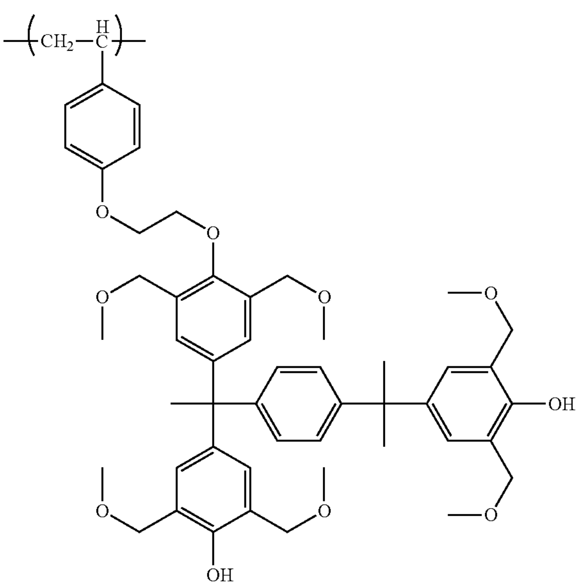

(Q-28)

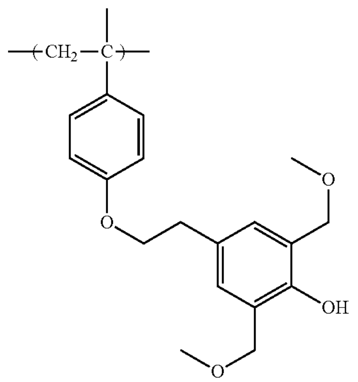

(Q-29)

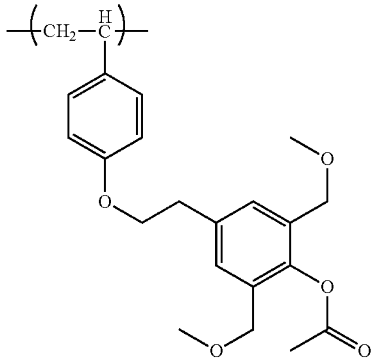

[4] Basic Compound

The active light sensitive or radiation sensitive resin composition of the present invention preferably contains a basic compound as an acid supplement in addition to the components. By using a basic compound, it is possible to reduce changes in the performance over time from exposure until post-heating. As such a basic compound, an organic basic compound is preferable, and more specific examples thereof include aliphatic amines, aromatic amines, heterocyclic amines, nitrogen-containing compounds having a carboxyl group, nitrogen-containing compounds having a sulfonyl group, nitrogen-containing compounds having a hydroxyl group, nitrogen-containing compounds having a hydroxyphenyl group, alcoholic nitrogen-containing compounds, amide derivatives, imide derivatives, and the like. It is also possible to appropriately use amine oxide compounds (preferably having a methyleneoxy unit and/or an ethyleneoxy unit, with examples including the compounds described in JP2008-102383A), and ammonium salts (preferably a hydroxide or a carboxylate, more specifically, tetraalkyl ammonium hydroxide typified by tetrabutyl ammonium hydroxide is preferable from the point of view of LER).

Furthermore, it is also possible to use a compound of which the basicity increases due to the action of an acid as one type of the basic compound.

Specific examples of the amines include tri-n-butylamine, tri-n-pentylamine, tri-n-octylamine, tri-n-decylamine, triisodecyl amine, dicyclohexyl methylamine, tetradecyl amine, pentadecyl amine, hexadecylamine, octadecylamine, didecylamine, methyl octadecyl amine, dimethyl undecyl amine, N,N-dimethyldodecylamine, methyl dioctadecyl amine, N,N-dibutyl aniline, N,N-dihexyl aniline, 2,6-diisopropyl aniline, 2,4,6-tri(t-butyl) aniline, triethanolamine, N,N-dihydroxyethyl aniline, tris(methoxyethoxyethyl) amine, compounds illustrated in column 3, line 60 and beyond in U.S. Pat. No. 6,040,112A, 2-[2-{2-(2,2-dimethoxy-phenoxyethoxy) ethyl}-bis-(2-methoxy-ethyl)]amine, compounds (C1-1) to (C3-3) illustrated in paragraph "0066" of US2007/0224539A1, and the like. Examples of the compound having a nitrogen-containing heterocyclic structure include 2-phenyl benzimidazole, 2,4,5-triphenyl imidazole, N-hydroxyethyl piperidine, bis (1,2,2,6,6-pentamethyl-4-piperidyl) sebacate, 4-dimethylaminopyridine, antipyrine, hydroxy antipyrine, 1,5-diazabicyclo[4.3.0]non-5-ene, 1,8-diazabicyclo[5.4.0]-undec-7-ene, tetrabutyl ammonium hydroxide, and the like.

In addition, it is also possible to appropriately use photodegradable basic compounds (compounds which initially exhibit basicity due to a basic nitrogen atom acting as a base, but generate amphoteric ionic compounds which have a basic nitrogen atom and an organic acid moiety by being decomposed due to irradiation with active light or radiation, and of which the basicity is reduced or lost by these ions being neutralized in the molecule, and examples thereof including the onium salts described in JP3577743B, JP2001-215689A, JP2001-166476A, JP2008-102383A), or photobase generators (for example, the compounds described in JP2010-243773A).

Since it is possible to obtain a favorable LER even in these basic compounds, ammonium salts or photodegradable basic compounds are preferable.

In the present invention, the basic compound may be used alone, or may be used in a combination of two or more types.

The content of the basic compound used in the present invention is preferably 0.01 mass % to 10 mass %, and more preferably 0.03 mass % to 5 mass %, and particularly preferably 0.05 mass % to 3 mass %, with respect to the total solid content of the active light sensitive or radiation sensitive resin composition.

[5] Surfactant

The active light sensitive or radiation sensitive resin composition of the present invention may further contain a surfactant in order to improve the coating properties. Examples of surfactants are not particularly limited; however, examples include non-ionic surfactants such as polyoxyethylene alkyl ethers, polyoxyethylene alkylaryl ethers, polyoxyethylene polyoxypropylene block copolymers, sorbitan fatty acid esters, and polyoxyethylene sorbitan fatty acid esters; fluorinated surfactants such as Megafac F171, F176 (manufactured by DIC Corporation), Fluorad FC430 (produced by Sumitomo 3M Ltd.), Surfynol E1004 (produced by Asahi Glass Co., Ltd.), PF656 and PF6320 produced by Omnova Solutions Inc., and organosiloxane polymers such as polysiloxane polymer KP-341 (produced by Shin-Etsu Chemical Co., Ltd.).

In a case where the active light sensitive or radiation sensitive resin composition contains a surfactant, the usage amount of the surfactant is preferably 0.0001 mass % to 2 mass % with respect to the total amount (excluding a solvent) of the active light sensitive or radiation sensitive resin composition, and more preferably 0.0005 mass % to 1 mass %.

[6] Organic Carboxylic Acid

The active light sensitive or radiation sensitive resin composition of the present invention preferably contains an organic carboxylic acid in addition to the components from the point of view of the scum characteristics. Examples of such organic carboxylic acid compounds include aliphatic carboxylic acid, alicyclic carboxylic acids, unsaturated aliphatic carboxylic acids, oxycarboxylic acids, alkoxy carboxylic acid, ketocarboxylic acid, benzoic acid, benzoic acid derivatives, phthalic acid, terephthalic acid, isophthalic acid, 2-naphthoic acid, 1-hydroxy-2-naphthoic acid, 2-hydroxy-3-naphthoic acid, and the like; however, since there is a concern that the inside of a drawing chamber will be contaminated due to volatilization of the resist film surface when performing an electron beam exposure under vacuum, preferable compounds include aromatic organic carboxylic acids, among which suitable examples include benzoic acid, 1-hydroxy-2-naphthoic acid, and 2-hydroxy-3-naphthoic acid.

The blending amount of the organic carboxylic acid is preferably in a range of 0.01 parts by mass to 10 parts by mass, more preferably 0.01 parts by mass to 5 parts by mass, and even more preferably 0.01 parts by mass to 3 parts by mass with respect to 100 parts by mass of the compound (B) which has a phenolic hydroxyl group.

The active light sensitive or radiation sensitive resin composition of the present invention may further contain, as necessary, dyes, plasticizers, acid-increasing agents other than compound (A) (described in WO095/29968A, WO98/24000A, JP1996-305262A (JP-H08-305262A), JP1997-34106A (JP-H09-34106A), JP1996-248561A (JP-H08-248561A), JP1996-503082A (JP-S08-503082A), U.S. Pat. No. 5,445,917A, JP1996-503081A (JP-S08-503081A), U.S. Pat. No. 5,534,393A, U.S. Pat. No. 5,395,736A, U.S. Pat. No. 5,741,630A, U.S. Pat. No. 5,334,489A, U.S. Pat. No. 5,582,956A, U.S. Pat. No. 5,578,424A, U.S. Pat. No. 5,453,345A, U.S. Pat. No. 5,445,917A, EP665960B, EP757628B, EP665961B, U.S. Pat. No. 5,667,943A, JP1998-1508A (JP-H10-1508A), JP1998-282642A (JP-H10-282642A), JP1997-512498A (JP-H09-512498A), JP2000-62337A, JP2005-17730A, JP2008-209889A, or the like), or the like. Examples of these compounds include each of the compounds described in JP2008-268935A.

[Carboxylic Acid Onium Salt]

The active light sensitive or radiation sensitive resin composition of the present invention may contain a carboxylic acid onium salt. Examples of the carboxylic acid onium salt include carboxylic acid sulfonium salt, carboxylic acid iodonium salt, carboxylic acid ammonium salt, and the like. In particular, the carboxylic acid onium salt is preferably a carboxylic acid iodonium salt, or a carboxylic acid sulfonium salt. Furthermore, in the present invention, the carboxylate residue of the carboxylic acid onium salt preferably does not contain an aromatic group or a carbon-carbon double bond. As a particularly preferable anion moiety, a straight-chain, branched, monocyclic or polycyclic alkyl carboxylic acid anion having 1 to 30 carbon atoms is preferable. More preferably, anions of a carboxylic acid in which some or all of these alkyl groups are substituted with a fluorine atom are preferable. In addition, an oxygen atom may be included in the alkyl chain. Due to this, transparency with respect to light with a wavelength of 220 nm or less is ensured, the sensitivity and resolving power are increased, and the density dependence and exposure margin are improved.

[7] Compound Generating an Acid Due to the Action of an Acid

The active light sensitive or radiation sensitive resin composition of the present invention may further include one type or two or more types of compounds which generates an acid by being decomposed due to the action of an acid. The acid which is generated by the compound which generates an acid by being decomposed due to the action of an acid described above is preferably a sulfonic acid, a methide acid, or imide acid.

Examples of the compounds which are able to be used in the present invention are described below; however, the present invention is not limited thereto.

(PA-1)

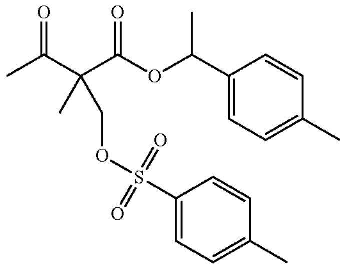

(PA-2)

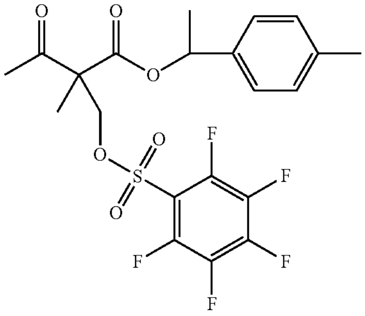

(PA-3)

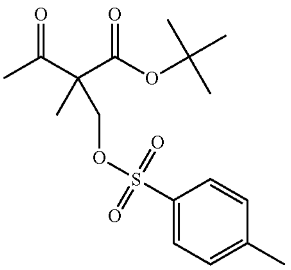

-continued
(PA-4)
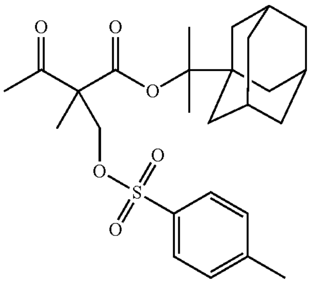
(PA-5)
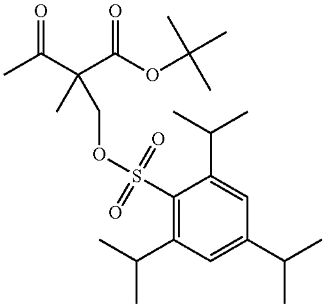
(PA-6)
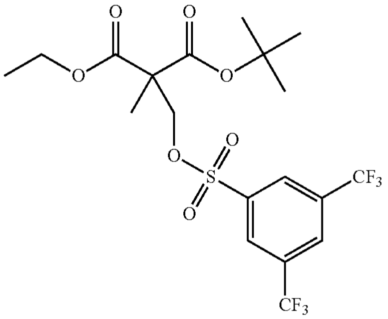
(PA-7)
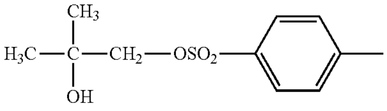
(PA-8)
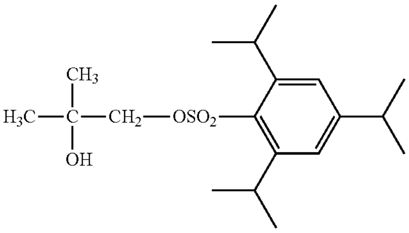
(PA-9)
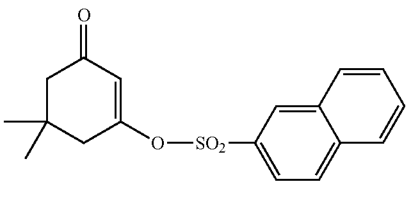
-continued
(PA-10)
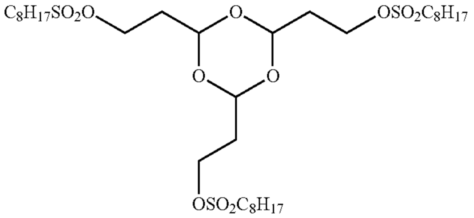
(PA-11)
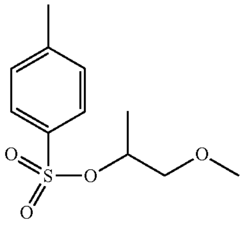
(PA-12)
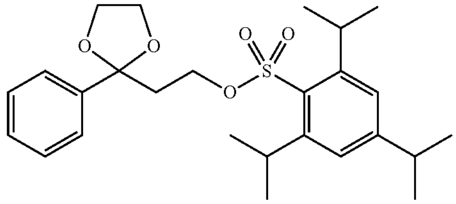
(PA-13)
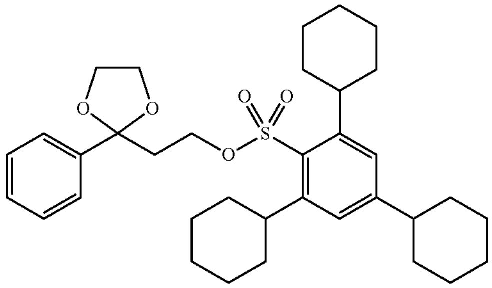
(PA-14)
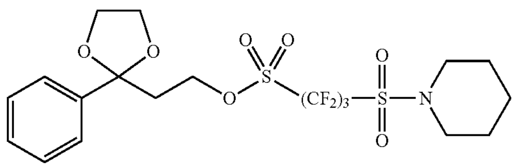
(PA-15)
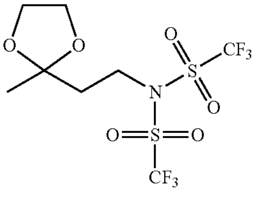

-continued (PA-16)

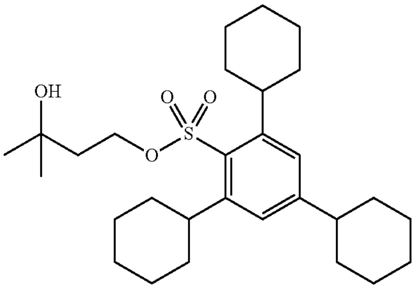

(PA-17)

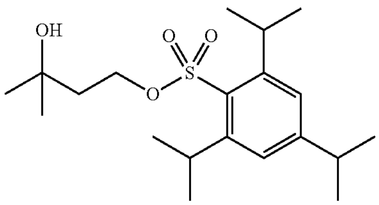

(PA-18)

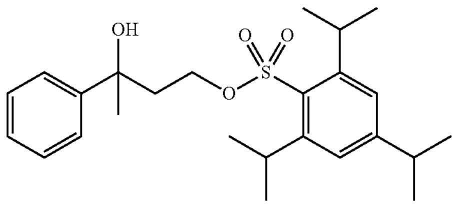

[8] Hydrophobic Resin

The active light sensitive or radiation sensitive resin composition of the present invention may have a hydrophobic resin (HR) separate to the compound (B) described above. By adding such a resin, it is possible to expect an effect of making the pattern close to rectangular and an effect of suppressing outgassing. In addition, it is possible to preferably use such a resin composition in a case where exposure is performed by filling a liquid (pure water or the like) with a higher refractive index than air between the photosensitive film and the lens, that is, in a case of performing liquid dipping exposure.

The hydrophobic resin (HR) described above preferably contains a group which has a fluorine atom, a group which has a silicon atom, or a hydrocarbon group having 5 or more carbon atoms in order to carry out uneven distribution on the film surface. These groups may be present in the main chain of the resin or may be substituted in the side chain.

Specific examples of the hydrophobic resin (HR) described above include the resins described in paragraphs "0240" to "0247" of JP2010-175858A or the resins described in paragraphs "0349" to "0354" of JP2013-80006A.

[9] Solvent

Preferable examples of solvents to be used in the active light sensitive or radiation sensitive resin composition of the present invention include ethylene glycol monoethyl ether acetate, cyclohexanone, 2-heptanone, propylene glycol monomethyl ether (PGME, also known as 1-methoxy-2-propanol), propylene glycol monomethyl ether acetate (PGMEA, also known as 1-methoxy-2-acetoxypropane), propylene glycol monomethyl ether propionate, propylene glycol monoethyl ether acetate, 3-methoxypropionate methyl, 3-ethoxypropionate ethyl, methyl β-methoxyisobutyrate, ethyl butyrate, propyl butyrate, methyl isobutyl ketone, ethyl acetate, isoamyl acetate, ethyl lactate, toluene, xylene, cyclohexyl acetate, diacetone alcohol, N-methylpyrrolidone, N,N-dimethylformamide, γ-butyrolactone, N,N-dimethylacetamide, propylene carbonate, ethylene carbonate, and the like. It is possible to use these solvents alone or in combination.

The solid content of the active light sensitive or radiation sensitive resin composition is preferably 1 mass % to 40 mass % of the solid content concentration, more preferably 1 mass % to 30 mass %, and even more preferably 3 mass % to 20 mass %.

The present invention also relates to a resist film formed using the active light sensitive or radiation sensitive resin composition of the present invention, and such a resist film is, for example, formed by coating a support body such as a substrate with the active light sensitive or radiation sensitive resin composition. The thickness of the resist film is preferably 0.02 μm to 0.1 μm. The coating is carried out on the substrate using an appropriate coating method such as spin coating, roll coating, flow coating, dip coating, spray coating, doctor coating as the method for coating the substrate; however, spin coating is preferable, and the rotation speed is preferably 1,000 rpm to 3,000 rpm. The coating film forms a thin film by being prebaked for 1 to 20 minutes at 60° C. to 150° C., preferably for 1 to 10 minutes at 80° C. to 120° C.

As the material forming the substrate to be processed and the outermost layer thereof, for example, it is possible to use a silicon wafer in a case of a wafer for a semiconductor, and examples of the material forming the outermost layer include Si, $SiO_2$, SiN, SiON, TiN, WSi, BPSG, SOG organic anti-reflection films, and the like.

In addition, the present invention also relates to a resist-coated mask blank (and a photomask obtained by exposing and developing a resist-coated mask blank) coated with the resist film obtained in the manner described above. In order to obtain such a resist-coated mask blank, in a case where a resist pattern is formed on a photomask blank for manufacturing a photomask, examples of a transparent substrate to be used include transparent substrates of quartz, calcium fluoride, and the like. Generally, necessary functional films such as a light-shielding film, an anti-reflection film, a phase shift film, and additionally an etching stopper film, or an etching mask film are laminated on the substrate. A film which contains a transition metal such as silicon, chromium, molybdenum, zirconium, tantalum, tungsten, titanium, niobium is laminated as the material of the functional film. In addition, examples of the material to be used in the outermost layer include material where silicon or a material which contains oxygen and/or nitrogen in silicon is set as the main constituent material, silicon compound material where a material which contains transition metals in these is set as the main constituent material, or transition metal compound material where a material which includes one type or more which is selected from transition metals, in particular, chromium, molybdenum, zirconium, tantalum, tungsten, titanium, niobium, and the like, or a material which includes one or more elements selected from oxygen, nitrogen, and carbon in the transition metals is set as the main constituent material.

The shielding film may be a single layer, however, the shielding film is more preferably a multi-layer structure in which a plurality of materials are coated on top of each other. In the case of a multi-layer structure, the film thickness of one layer is not particularly limited; however, 5 nm to 100 nm is preferable, and 10 nm to 80 nm is more preferable. The thickness of the whole light-shielding film is not particularly limited; however, 5 nm to 200 nm is preferable, and 10 nm to 150 nm is more preferable.

Among these materials, generally, in a case where pattern forming is performed using an active light sensitive or radiation sensitive resin composition on a photomask blank which has a material containing oxygen or nitrogen in chromium on the outermost layer, a constricted shape is formed in the vicinity of the substrate, that is, there is a tendency to form an undercut shape; however, when using the present invention, it is possible to improve the undercutting problem in comparison with the related art.

Next, developing is carried out after irradiating the resist film with active light or radiation (electron beams or the like) and preferably performing baking (normally at 80° C. to 150° C., more preferably 90° C. to 130° C., and normally for 1 to 20 minutes, and more preferably for 1 to 10 minutes). Due to this, it is possible to obtain a favorable pattern. Then, by using this pattern as a mask, appropriate etching processing, ion implantation, and the like are performed, and a semiconductor microcircuit and a mold structure, a photomask, or the like for imprinting is created.

Here, the process in a case of creating a mold for imprinting using the composition of the present invention is described in, for example, JP4109085B, and JP2008-162101A.

Next, the form for using the active light sensitive or radiation sensitive resin composition of the present invention and the pattern forming method will be described.

The present invention also relates to a pattern forming method including exposing the resist film or the resist-coated mask blank described above, and developing the exposed resist film or the resist-coated mask blank. In the present invention, the exposure is preferably performed using ArF light, KrF light, electron beams or extreme ultraviolet light.

In the manufacturing of precision integrated circuit elements and the like, regarding the exposure (the pattern forming step) on the resist film, it is first preferable to irradiate the resist film of the present invention with electron beams or extreme ultraviolet light (EUV) in the pattern shape. The exposure is carried out with an exposure amount of approximately 0.1 $\mu C/cm^2$ to 20 $\mu C/cm^2$ in the case of electron beams, preferably approximately 3 $\mu C/cm^2$ to 15 $\mu C/cm^2$, and approximately 0.1 $mJ/cm^2$ to 20 $mJ/cm^2$ in the case of extreme ultraviolet light, preferably approximately 3 $mJ/cm^2$ to 15 $mJ/cm^2$. Next, post-heating exposure (post exposure bake) is performed at 60° C. to 150° C. for 1 to 20 minutes on a hot plate, preferably 80° C. to 120° C. for 1 to 10 minutes, then a resist pattern is formed by carrying out developing, rinsing, and drying.

In the development step, normally, an alkali developer or a developer which contains an organic solvent (referred to below as an organic developer) is used. As the alkali developer, it is possible to use alkaline aqueous solutions such as inorganic alkalis such as sodium hydroxide, potassium hydroxide, sodium carbonate, sodium silicate, sodium metasilicate, and ammonia water; primary amines such as ethylamine, and n-propylamine; secondary amines such as diethylamine, and di-n-butylamine; tertiary amines such as triethylamine, and methyldiethylamine; alcohol amines such as dimethylethanolamine, and triethanolamine; tetraalkyl ammonium hydroxides such as tetramethyl ammonium hydroxide, tetraethyl ammonium hydroxide, tetrapropyl ammonium hydroxide, tetrabutyl ammonium hydroxide, tetrapentyl ammonium hydroxide, tetrahexyl ammonium hydroxide, tetraoctyl ammonium hydroxide, ethyl trimethyl ammonium hydroxide, butyl trimethyl ammonium hydroxide, methyl triamyl ammonium hydroxide, and dibutyl dipentyl ammonium hydroxide; quaternary ammonium salts such as trimethyl phenyl ammonium hydroxide, trimethyl benzyl ammonium hydroxide, and triethyl benzyl ammonium hydroxide; or cyclic amines such as pyrrole or piperidine. Furthermore, use is also possible by adding alcohols or a surfactant in appropriate amounts to the alkaline aqueous solution described above. The alkali concentration of the alkali developer is usually 0.1 mass % to 20 mass %. The particularly preferable alkali developer is an aqueous solution with 2.38% by mass of tetramethyl ammonium hydroxide.

The pH of the alkali developer is usually 10.0 to 15.0. The alkali developer may contain the surfactants or organic solvents described above. In a case where the developer is an alkali developer, it is also possible to use pure water as the rinsing liquid and add a surfactant thereto in appropriate amounts.

The organic developer is particularly preferably used when obtaining a negative type pattern using a composition which includes a resin of which the solubility is increased with respect to the alkali developer due to the action of an acid (in other words, a resin which has a group of which the polarity is increased due to the action of an acid). As the organic developer, it is possible to use polar solvents such as ester solvents (butyl acetate, propylene glycol monomethyl ether, or the like), ketone solvents (2-nonanone, 2-heptanone, cyclohexanone, or the like), alcohol solvents, amide solvents, ether solvents, and hydrocarbon solvents. The water content of the entire organic developer is preferably less than 10 mass %, and moisture is more preferably substantially not contained.

That is, the usage amount of the organic solvent with respect to the organic developer is preferably 90 mass % or more to 100 mass % or less with respect to the total amount of the developer, and 95 mass % or more to 100 mass % or less is preferable.

It is possible to add an appropriate amount of alcohols and/or surfactants to the developer as necessary.

The surfactant is not particularly limited; however, for example, it is possible to use ionic or non-ionic fluorine-based and/or silicon-based surfactants or the like. Examples of these fluorine and/or silicon-based surfactants include the surfactants described in JP1987-36663A (JP-S62-36663A), JP1986-226746A (JP-S61-226746A), JP1986-226745A (JP-S61-226745A), JP1987-170950A (JP-S62-170950A), JP1988-34540A (JPS63-34540A), JP1995-230165A (JP-H07-230165A), JP1996-62834A (JP-H08-62834A), JP1997-54432A (JP-H09-54432A), JP1997-5988A (JP-H09-5988A), U.S. Pat. No. 5,405,720A, U.S. Pat. No. 5,360,692A, U.S. Pat. No. 5,529,881A, U.S. Pat. No. 5,296,330A, U.S. Pat. No. 5,436,098A, U.S. Pat. No. 5,576,143A, U.S. Pat. No. 5,294,511A, and U.S. Pat. No. 5,824,451A, and non-ionic surfactants are preferable. The non-ionic surfactant is not particularly limited; however, a fluorine-based surfactant or a silicon-based surfactant is more preferably used.

The usage amount of the surfactant is normally 0.001 mass % to 5 mass % with respect to the total amount of the developer, preferably 0.005 mass % to 2 mass %, and even more preferably 0.01 mass % to 0.5 mass %.

The developer used in the present invention may include a basic compound. Specific examples and preferable examples of basic compounds able to be included in the developer to be used in the present invention include the compounds given as basic compounds able to be included in the active light sensitive or radiation sensitive resin composition described above.

As the developing method, it is possible to apply, for example, a method for dipping a substrate in a tank which is filled with a developer for a certain time (a dipping method), a method for carrying out developing by raising the developer onto the substrate surface using surface tension and leaving the substrate to stand still for a certain time (a paddling method), a method for spraying the developer onto the substrate surface (a spraying method), a method for continuously discharging a developer onto a substrate which is rotating at a certain speed while scanning a developer discharging nozzle at a certain speed (a dynamic dispensing method), and the like.

In a case where the various types of the developing methods described above include a step of discharging the developer from the developing nozzle of the developing apparatus toward the resist film, the discharging pressure of the discharged developer (the flow rate of the discharged developer per unit area) is preferably 2 $mL/sec/mm^2$ or less, more preferably 1.5 $mL/sec/mm^2$ or less, and even more preferably 1 $mL/sec/mm^2$ or less. There is no particular lower limit on the flow rate; however, when considering throughput, 0.2 $mL/sec/mm^2$ or more is preferable.

By setting the discharging pressure of the developer to be discharged to the ranges described above, it is possible to greatly reduce defects in the pattern deriving from residual resist after the development.

The details of this mechanism are not certain; however, it is considered to be likely that, by setting the discharging pressure to the range described above, the pressure which the developer applies to the resist film is reduced and accidental scratching or destruction of the resist film and the resist pattern is suppressed.

Here, the discharging pressure ($mL/sec/mm^2$) of the developer is the value in the developer nozzle outlet in the developer apparatus.

Examples of a method for adjusting the discharging pressure of the developer include a method for adjusting the discharging pressure with a pump or the like, a method for adjusting and changing the pressure through the supply from a pressure tank, and the like.

In addition, after the step of developing using a developer, a step of stopping the development may be carried out while carrying out substitution with another solvent.

As a rinsing liquid in a rinsing process after the alkali development, it is also possible to use pure water and add a surfactant thereto in appropriate amounts.

In a case where the developer is an organic developer, it is preferable to use a rinsing liquid which contains at least one type of an organic solvent which is selected from a group formed of ketone solvents, ester solvents, alcohol solvents, and amide solvents. Among these, 4-methyl-2-pentanol, 1-hexanol, or methyl isobutyl carbinol are preferably used.

In the pattern forming method of the present invention, it is possible to combine a step of developing using a developer which includes an organic solvent (organic solvent developing step), and a step of performing development using an alkaline aqueous solution and forming a resist pattern (alkali development step). Due to this, it is possible to form a finer pattern.

In the present invention, a portion where the exposure strength is weak is removed by the organic solvent development step, while a portion where the exposure strength is strong is also removed by further performing an alkali development step. According to this multi-development process in which the development is performed a plurality of times, since it is possible to form a pattern where only a region where the exposure strength is intermediate is not dissolved, it is possible to form a finer pattern than usual (the mechanism is the same as in paragraph "0077" in JP2008-292975A).

In the pattern forming method of the present invention, the order of the alkali development step and the organic solvent development step is not particularly limited; however, it is preferable to perform the alkali development before the organic solvent development step.

In this manner, regarding the resist film formed from the active light sensitive or radiation sensitive resin composition of the present invention, the resist film in the unexposed portion is dissolved by the developer, and the exposed portion is not easily dissolved by the developer since the compound which has a phenolic hydroxyl group is cross-linked, and the desired pattern is formed on the substrate.

In addition, the present invention also relates to a photomask obtained by exposing and developing the resist-coated mask blank. The steps described above are applied as the exposure and the development. The photomask is favorably used for semiconductor manufacturing.

The photomask of the present invention may be a light transmission type mask used with an ArF excimer laser or the like, or may be an optical reflection type mask used in reflection-based lithography with EUV light as the light source.

It is also possible to use the pattern forming method of the present invention in guide pattern forming in Directed Self-Assembly (DSA) (for example, refer to ACS Nano Vol. 4 No. 8, page 4815 to 4823).

In addition, in the resist pattern formed by the method described above, it is also possible to use as a core material (core) of the spacer process described in, for example, JP1991-270227A (JP-H03-270227 A) and JP2013-164509A.

The present invention also relates to a method for manufacturing an electronic device including the pattern forming method of the present invention described above, and to an electronic device manufactured using this manufacturing method.

The electronic device of the present invention is suitable for mounting on electric or electronic devices (home appliances, OA or media-related equipment, optical equipment, and communications equipment, and the like).

EXAMPLES

More detailed description will be given below of the present invention using Examples; however, the content of the present invention is not limited thereto.

<Synthesis of Compound (A1)>

5.0 g of sodium 2-mercapto ethanesulfonate, 1.20 g of sodium hydroxide, 50 g of pure water, and 10 g of tetrahydrofuran (THF) were mixed and cooled to 0° C., then 6.05 g of adamantane carbonyl chloride was added thereto, and stirring was carried out for two hours at room temperature. Next, after adding a methanol solution of 10.45 g of triphenylsulfonium bromide and stirring for 30 minutes at room temperature, separation was carried out by adding pure water and ethyl acetate to the reaction mixture and the organic phase was cleaned with pure water, then the compound (A1) (12.3 g) was obtained by vacuum drying after distilling off the solvent under reduced pressure.

Here, the $^1$H-NMR spectrum of the compound (A1) (400 MHz, $CDCl_3$) is δ=7.86-7.66 (m, 15H), 3.32-3.28 (m, 2H), 3.06-3.02 (m, 2H), and 2.06-1.64 (m, 15H).

<Synthesis of Compound (A2)>

12.5 g of the compound (A2) was obtained with the same method as in the synthesis of the compound (A1) except that the 10.45 g of triphenylsulfonium bromide was changed to 11.73 g of the following sulfonium salt (B).

(B)

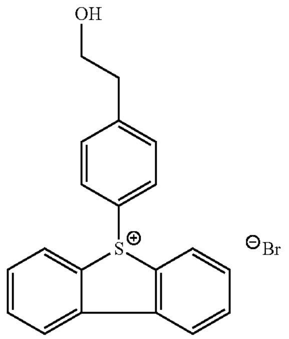

$^1$H-NMR (400 MHz, $CDCl_3$) δ=8.35 (d, 2H), 8.11 (d, 2H), 7.79 (t, 2H), 7.74 (d, 2H), 7.57 (t, 2H), 7.31 (d, 2H), 3.79 (t, 2H), 3.32-3.28 (m, 2H), 3.06-3.02 (m, 2H), 2.82 (t, 2H), 2.06-1.64 (m, 15H).

<Compound (A3)>

4.42 g of 2-amino ethanesulfonic acid, 2.4 g of sodium hydroxide, 50 g of pure water, and 10 g of THF were mixed and cooled to 0° C., then 6.05 g of adamantane carbonyl chloride was added thereto, and stirring was carried out for four hours at 50° C. Next, after adding a methanol solution of 10.45 g of triphenylsulfonium bromide and stirring for 30 minutes at room temperature, separation was carried out by adding pure water and chloroform to the reaction mixture and the organic phase was cleaned with pure water, then the compound (A3) (11.3 g) was obtained by vacuum drying after distilling off the solvent under reduced pressure.

$^1$H-NMR (400 MHz, $CDCl_3$) δ=7.83-7.67 (15H, m), 3.71-3.66 (m, 2H), 2.93-2.89 (m, 2H), 1.98-1.62 (m, 15H)

<Compound (A4)>

12.9 g of the compound (A4) was obtained with the same method as in the synthesis of the compound (A1) except that the 10.45 g of triphenylsulfonium bromide was changed to 13.19 g of the following sulfonium salt (C).

(C)

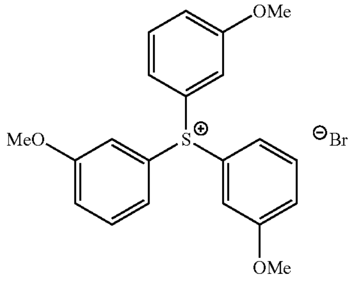

<Compound (A5)>

12.1 g of the compound (A5) was obtained with the same method as in the synthesis of the compound (A1) except that the 5.0 g of sodium 2-mercapto ethanesulfonate was changed to 5.36 g of sodium 3-mercapto propanesulfonate.

<Compound (A6)>

11.5 g of the compound (A6) was obtained with the same method as in the synthesis of the compound (A1) except that the 10.45 g of triphenylsulfonium bromide was changed to 10.67 g of the following iodonium salt.

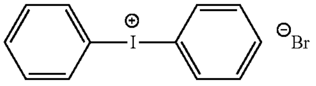 [SMILES: c1ccc([I+]c2ccccc2)cc1 ; [Br-]]

$^1$H-NMR (400 MHz, $CDCl_3$) δ=7.91 (d, 4H), 7.57 (t, 2H), 7.41 (t, 4H), 3.32-3.28 (m, 2H), 3.06-3.02 (m, 2H), 2.06-1.64 (m, 15H)

<Compound (A7)>

13.1 g of the compound (A7) was obtained with the same method as in the synthesis of the compound (A3) except that the 10.45 g of triphenylsulfonium bromide was changed to 12.1 g of the following sulfonium salt.

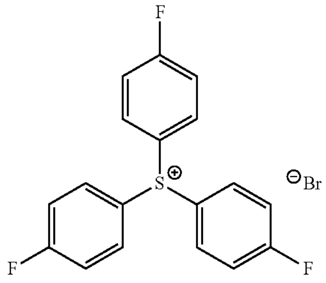 [SMILES: Fc1ccc([S+](c2ccc(F)cc2)c2ccc(F)cc2)cc1 ; [Br-]]

$^1$H-NMR (400 MHz, d6-DMSO) δ=7.96-7.91 (6H, m), 7.69-7.63 (6H, m), 7.59 (1H, brs), 3.32-3.27 (m, 2H), 2.52-2.49 (m, 2H), 1.98-1.59 (m, 15H)

<Compound (A8)>

12.9 g of the compound (A8) was obtained with the same method as in the synthesis of the compound (A1) except that the 10.45 g of triphenylsulfonium bromide was changed to 10.09 g of the following sulfonium salt.

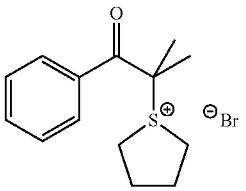 [SMILES: CC(C)(C(=O)c1ccccc1)[S+]1CCCC1 ; [Br-]]

<Compound (A9)>

12.2 g of the compound (A9) was obtained with the same method as in the synthesis of the compound (A3) except that the 10.45 g of triphenylsulfonium bromide was changed to 9.90 g of the following sulfonium salt.

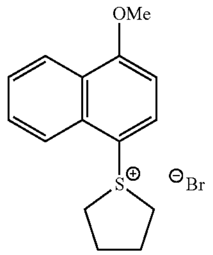 [SMILES: COc1ccc([S+]2CCCC2)c2ccccc12 ; [Br-]]

<Compound (A10)>

10.1 g of the compound (A10) was obtained with the same method as in the synthesis of the compound (A3) except that the 6.05 g of adamantane carbonyl chloride was changed to 3.67 g of pivaloyl chloride.

$^1$H-NMR (400 MHz, d6-DMSO) δ=7.89-7.76 (15H, m), 7.64 (1H, brs), 3.31 (m, 2H), 2.55 (t, 2H), 1.06 (s, 9H)

<Compound (A11)>

10.3 g of the compound (A11) was obtained with the same method as in the synthesis of the compound (A1) except that the 6.05 g of adamantane carbonyl chloride was changed to 4.27 g of benzoyl chloride.

$^1$H-NMR (400 MHz, $D_2O$) δ=7.98 (d, 2H), 7.80-7.63 (m, 17H), 7.55 (t, 2H), 3.11-3.06 (2H, m), 3.02-2.97 (2H, m)

<Compound (A12)>

21.4 g of phthalic anhydride, 17 g of taurine, and 14.2 g of potassium acetate were added to 48 mL of acetic acid and stirred while carrying out refluxing for 2.5 hours. After cooling to 0° C. after the reaction and filtering the precipitate, spray washing was carried out with acetic acid and ethanol. Next, after adding the obtained crystals to a methanol solution of 38.6 g of triphenylsulfonium bromide and stirring for 30 minutes at room temperature, separation was carried out by adding pure water and ethyl acetate to the reaction mixture and the organic phase was cleaned with pure water, then the compound (A12) (52.3 g) was obtained by vacuum drying after distilling off the solvent under reduced pressure.

$^1$H-NMR (400 MHz, $D_2O$) δ=7.85 (4H, m), 7.80-7.63 (m, 15H), 4.05 (2H, t), 3.25 (2H, t)

<Compound (A13)>

13.3 g of the compound (A13) was obtained with the same method as in the synthesis of the compound (A3) except that the 10.45 g of triphenylsulfonium bromide was changed to 10.67 g of the following iodonium salt.

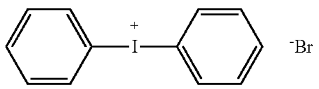

$^1$H-NMR (400 MHz, $CDCl_3$) δ=7.91 (d, 4H), 7.57 (t, 2H), 7.41 (t, 4H), 3.71-3.66 (m, 2H), 2.93-2.89 (m, 2H), 1.98-1.62 (m, 15H)

<Compound (A14)>

10.2 g of the compound (A14) was obtained with the same method as in the synthesis of the compound (A3) except that the 6.05 g of adamantane carbonyl chloride was changed to 5.38 g of benzenesulfonyl chloride.

<Compound (A15)>

10.3 g of the compound (A15) was obtained with the same method as in the synthesis of the compound (A3) except that the 4.42 g of 2-aminoethanesulfonic acid was changed to 3.92 g of amino methanesulfonic acid and 10.45 g of triphenylsulfonium bromide was changed to 10.88 g of the following sulfonium salt.

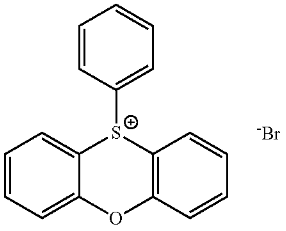

<Compound (A16)>

10.8 g of the compound (A16) was obtained with the same method as in the synthesis of the compound (A3) except that the 4.42 g of 2-aminoethanesulfonic acid was changed to 4.91 g of 3-amino propane sulfonic acid and 10.45 g of triphenylsulfonium bromide was changed to 12.65 g of the following sulfonium salt.

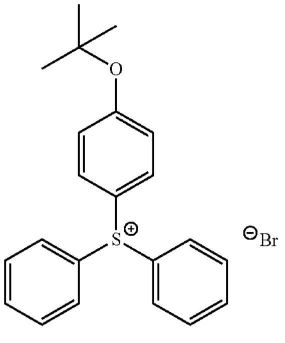 [SMILES: CC(C)(C)Oc1ccc([S+](c2ccccc2)c2ccccc2)cc1 ; [Br-]]

<Compound (A17)>

Compound (A17) was obtained by performing salt exchange between sodium taurocholate (produced by Tokyo Chemical Industry Co., Ltd.) and the sulfonium salt (C).

$^1$H-NMR (400 MHz, d6-DMSO) 0.6 (s, 3H), 0.8 (s, 3H), 0.9 (d, 3H), 2.6 (dd, 2H), 3.2 (m, 1H), 3.3 (dd, 2H), 3.6 (m, 1H), 3.8 (m, 1H), 3.9 (s, 10H), 4.0 (bsd, 1H), 4.3 (bsd, 1H), 7.7 (m, 4H), 7.47 (t, 3H), 7.20-7.12 (m, 6H)

<Compound (A18)>

The compound (A18) was obtained with the same method as in the synthesis of the compound (A3) except that adamantane carbonyl chloride was changed to dehydrocholic acid chloride.

The compound (A) used in the Examples and Comparative Examples is shown below.

TABLE 1

| Compound (for Examples) | Chemical Formula |
|---|---|
| Compound (A1) | 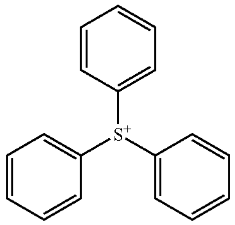 [SMILES: c1ccc([S+](c2ccccc2)c2ccccc2)cc1] |

TABLE 1-continued
| Compound (for Examples) | Chemical Formula |
|---|---|
| | 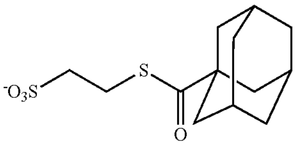 |
| Compound (A2) | 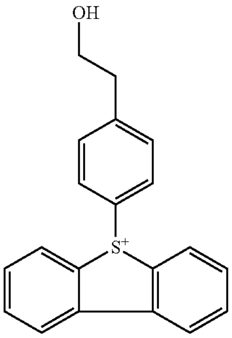 [SMILES: OCCc1ccc(-[s+]2c3ccccc3c3ccccc32)cc1] |
| | 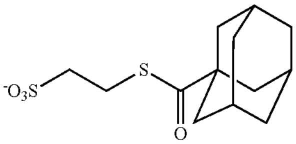 |
| Compound (A3) | 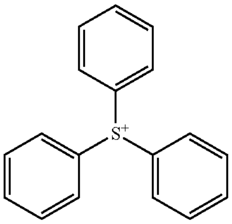 [SMILES: c1ccc([S+](c2ccccc2)c2ccccc2)cc1] |
| | 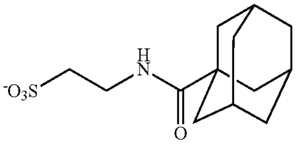 |
| Compound (A4) | 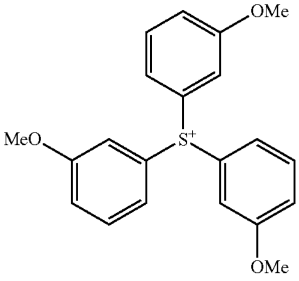 [SMILES: COc1cccc([S+](c2cccc(OC)c2)c2cccc(OC)c2)c1] |
| | 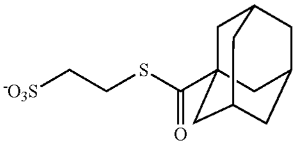 |
| Compound (A5) | 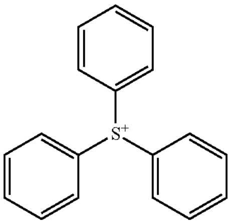 [SMILES: c1ccc([S+](c2ccccc2)c2ccccc2)cc1] |
| | 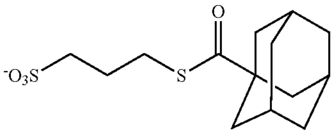 |
| Compound (A6) | 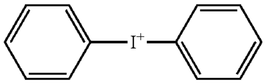 [SMILES: c1ccc([I+]c2ccccc2)cc1] |
| | 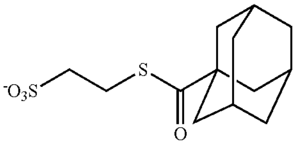 |
| Compound (A7) | 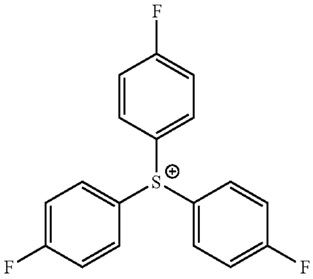 [SMILES: Fc1ccc([S+](c2ccc(F)cc2)c2ccc(F)cc2)cc1] |
| | 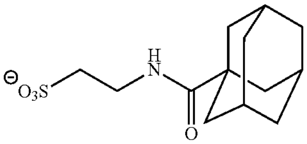 |
| Compound (A8) | 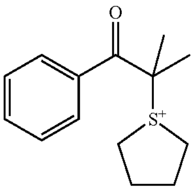 [SMILES: CC(C)(C(=O)c1ccccc1)[S+]1CCCC1] |
| | 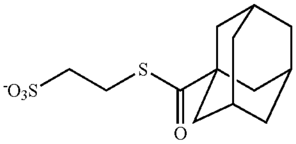 |

TABLE 2
| Compound (for Examples) | Chemical Formula |
| --- | --- |
| Compound (A9) | 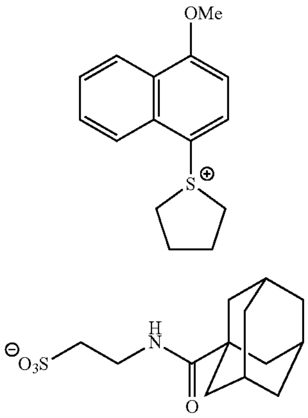 |
| Compound (A10) | 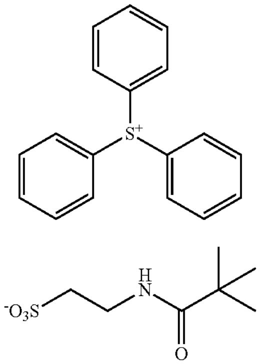 |
| Compound (A11) | 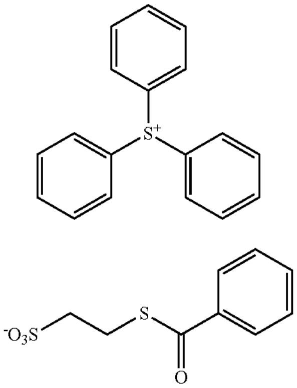 |
| Compound (A12) | 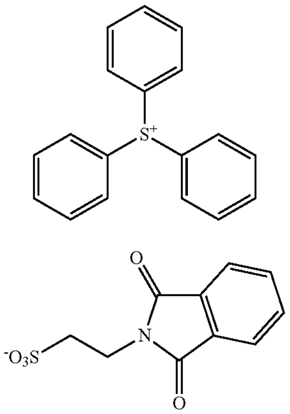 |

TABLE 2-continued
| Compound (for Examples) | Chemical Formula |
|---|---|
| Compound (A13) | 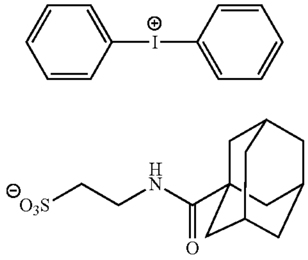 |
| Compound (A14) | 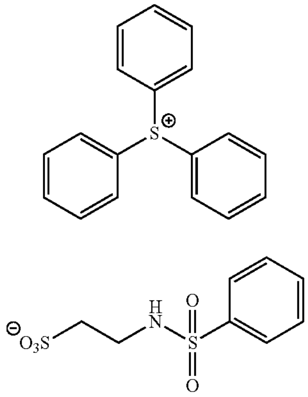 |
| Compound (A15) | 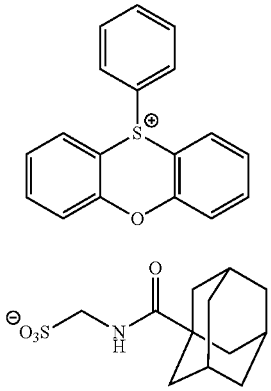 |
| Compound (A16) | 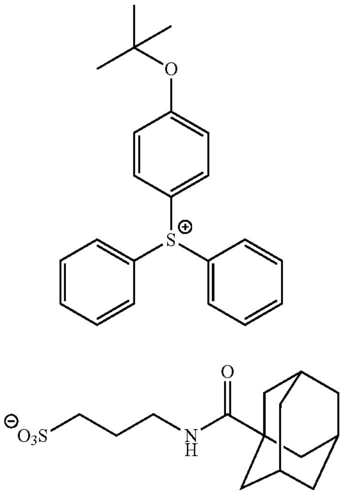 |

TABLE 2-continued
| Compound (for Examples) | Chemical Formula |
| --- | --- |
| Compound (A17) | 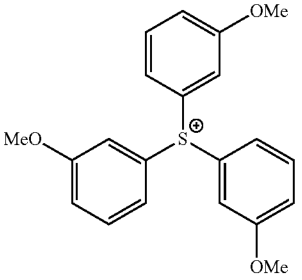 [SMILES: COc1cccc([S+](c2cccc(OC)c2)c2cccc(OC)c2)c1]<br>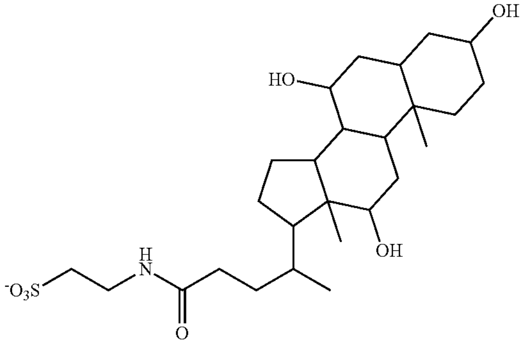 |
| Compound (A18) | 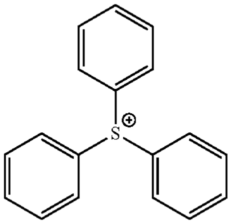 [SMILES: c1ccc([S+](c2ccccc2)c2ccccc2)cc1]<br>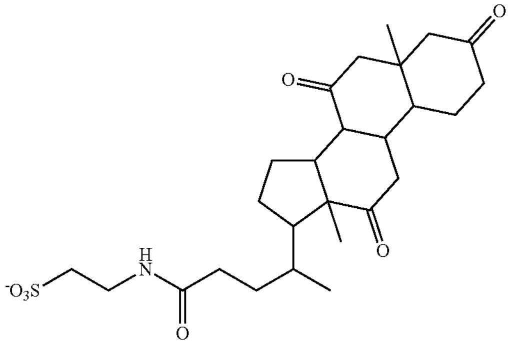 |
TABLE 3
| Compound (for Comparative Examples) | Chemical Formula |
| --- | --- |
| Comparative Compound 1 | 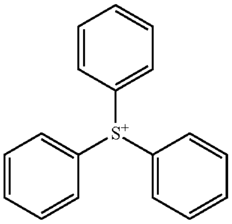 [SMILES: c1ccc([S+](c2ccccc2)c2ccccc2)cc1] |
TABLE 3-continued
| Compound (for Comparative Examples) | Chemical Formula |
| --- | --- |
| | 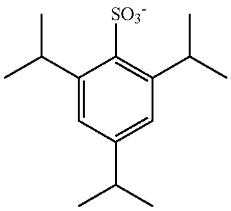 |

TABLE 3-continued

| Compound (for Comparative Examples) | Chemical Formula |
| --- | --- |
| Comparative Compound 2 | 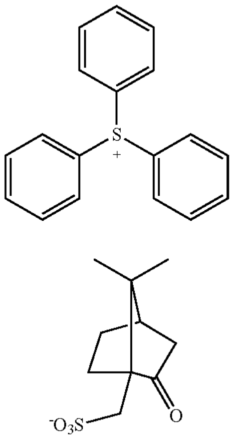 |
| Comparative Compound 3 | 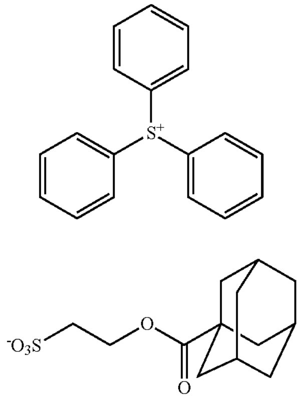 |
| Comparative Compound 4 | 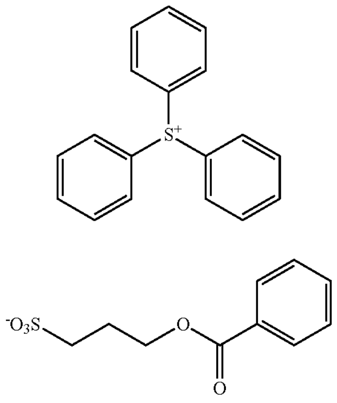 |

Example 1P (1) Preparation of Support

A 6-inch wafer on which Cr oxide was deposited (a wafer subjected to a film shielding process used for conventional photomask blanks) was prepared.

(2) Preparation of Resist Coating Solution (Coating Solution Composition of Positive Type Resist Composition P1)

Resin (P-4) 0.60 g

Compound (A1) (photoacid generator, the structural formula described above) 0.12 g Tetrabutyl ammonium hydroxide (basic compound) 0.02 g Surfactant PF6320 (produced by Omnova Solutions Inc.) 0.001 g Propylene glycol monomethyl ether acetate (solvent) 18.0 g A resist coating solution was obtained by passing the composition solution through a microfilter with a polytetrafluoroethylene filter which has a pore size of 0.04 μm.

(3) Creation of Resist Film

A resist film with a film thickness of 50 nm was obtained by coating the 6-inch wafers described above with a resist coating solution using a spin coater Mark 8 manufactured by Tokyo Electron Ltd., and carrying out drying on a hot plate for 90 seconds at 110° C. That is, a resist-coated mask blank was obtained.

(4) Preparation of Positive Type Resist Pattern

Pattern irradiation was performed on this resist film using an electron beam drawing apparatus (ELS-7500 manufactured by Elionix Inc., acceleration voltage 50 KeV). After the irradiation, heating was carried out on a hot plate for 90 seconds at 120° C., and immersion was carried out for 60 seconds using a 2.38 mass % tetramethyl ammonium hydroxide (TMAH) solution, rinsing was carried out for 30 seconds with water, and drying was carried out.

(5) Resist Pattern Evaluation

The sensitivity, the resolving power, the pattern shape, and the line edge roughness (LER) of the obtained pattern were evaluated using the following methods.

[Sensitivity]

The cross-sectional shape of the obtained pattern was observed using a scanning electron microscope (S-4300 manufactured by Hitachi, Ltd.). The exposure amount (the electron beam irradiation amount) when resolving a 1:1 line and space resist pattern with a line width of 50 nm was set as the sensitivity. The smaller this value is, the higher the sensitivity.

[LS Resolution Evaluation]

The limit resolving power (the minimum line width at which the lines and spaces are separately resolved) in the exposure amount (electron beam irradiation amount) indicating the sensitivity described above was set as the LS resolving power.

[IL Resolving Power]

The limit resolving power (the minimum line width at which the lines and spaces are separately resolved) in the minimum radiation amount when resolving an isolated line pattern with a line width of 50 nm (line:space=1:>50) was set as the IL resolving power (nm).

[Pattern Shape]

The cross-sectional shape of a 1:1 line and space resist pattern with a line width of 50 nm in the exposure amount (electron beam irradiation amount) indicating the sensitivity described above was observed using a scanning electron microscope (S-4300 manufactured by Hitachi, Ltd.). In the cross-sectional shape of the line pattern, for the ratio represented by [the line width in the bottom section of the line pattern/the line width in the center section (the height position of half the height of the line pattern) of the line pattern], a line pattern having a ratio of 1.2 or more was set as a "forward taper", a line pattern having a ratio of a ratio of 1.05 or more to less than 1.2 was set as a "slightly forward taper", and a line pattern having a ratio of a ratio of less than 1.05 was set as a "rectangle", and evaluation was performed.

[Line Edge Roughness (LER)]

A 1:1 line and space resist pattern with a line width of 50 nm was formed with a radiation amount (electron beam irradiation amount) indicating the sensitivity described above. Then, for an arbitrary 30 points included in 10 μm in the length direction thereof, the distance from a reference line where an edge should be present was measured using a scanning electron microscope (S-9220 manufactured by Hitachi, Ltd.). Then, the standard deviation of this distance was determined and 3σ was calculated. A smaller value indicates a more favorable performance.

[Example 2P] to [Example 27P] and [Comparative Example 1P] to [Comparative Example 4P]

In the resist solution formula, the preparation of the resist solution (the positive type resist compositions P2 to P27 and positive type resist comparative compositions P1 to P4), the positive type pattern forming, and the evaluation were performed in the same manner as Example 1P except for the components described in Table 4 below.

TABLE 4

[Electron beam exposure; positive type]
*0.01 g of benzoic acid was further added to Composition P16

| Composition | Photoacid generator (0.12 g) | Resin (0.60 g) | Basic Compound (0.02 g) | Surfactant (0.001 g) | Solvent (mass ratio) (18.0 g) |
|---|---|---|---|---|---|
| P1 | A1 | P-4 | B1 | W-1 | S1 |
| P2 | A2 | P-4 | B1 | W-1 | S1/S2(6/4) |
| P3 | A3 | P-4 | B1 | W-1 | S1/S2(6/4) |
| P4 | A4 | P-4 | B1 | W-1 | S1/S2(6/4) |
| P5 | A5 | P-4 | B1 | W-1 | S1/S2(6/4) |
| P6 | A6 | P-4 | B1 | W-1 | S1/S2(6/4) |
| P7 | A7 | P-4 | B1 | W-1 | S1/S2(6/4) |
| P8 | A8 | P-4 | B1 | W-1 | S1/S2(6/4) |
| P9 | A9 | P-4 | B1 | W-1 | S1/S2(6/4) |
| P10 | A10 | P-4 | B1 | W-1 | S1/S2(6/4) |
| P11 | A11 | P-4 | B1 | W-1 | S1/S2(6/4) |
| P12 | A12 | P-4 | B1 | W-1 | S1/S2(6/4) |
| P13 | A13 | P-4 | B1 | W-1 | S1/S4(6/4) |
| P14 | A14 | P-4 | B5 | W-1 | S1/S3(6/4) |
| P15 | A7 | P-9 | B2 | W-1 | S1/S5(6/4) |
| P16 | A1 | P-11 | B2 | W-1 | S1/S2/S6(6/3/1) |
| P17 | A1 | P-10 | B2 | W-2 | S1/S7(6/4) |
| P18 | A1 | P-12 | B3 | W-2 | S1/S2(6/4) |
| P19 | A12 | P-3 | B4 | W-3 | S1/S2(6/4) |
| P20 | A13 | P-7 | B5 | W-1 | S1/S2(6/4) |
| P21 | A14 | P-8 | B3 | W-3 | S1/S2(6/4) |
| P22 | A4/A1 (0.06 g/0.06 g) | P-2/P-5 (0.3 g/0.3 g) | B6 | None | S1/S2(6/4) |
| P23 | A1 | P-6 | B1 | W-1 | S1/S2(6/4) |
| P24 | A15 | P-4 | B1 | W-1 | S1/S4(6/4) |
| P25 | A16 | P-4 | B1 | W-1 | S1/S4(6/4) |
| P26 | A17 | P-4 | B1 | W-1 | S1/S2(6/4) |
| P27 | A18 | P-4 | B1 | W-1 | S1/S2(6/4) |
| Comparative Composition P1 | Comparative Compound 1 | P-1 | B2 | W-1 | S1/S2(6/4) |
| Comparative Composition P2 | Comparative Compound 2 | P-1 | B2 | W-1 | S1/S2(6/4) |
| Comparative Composition P3 | Comparative Compound 3 | P-1 | B2 | W-1 | S1/S2(6/4) |
| Comparative Composition P4 | Comparative Compound 4 | P-1 | B2 | W-1 | S1/S2(6/4) |

Other components used in the Examples and Comparative Examples are shown below.

The structure of the resin, composition ratio (molar ratio), weight-average molecular weight, and degree of dispersity used in the Examples and the Comparative Examples are shown below.

[Resin]

P-1

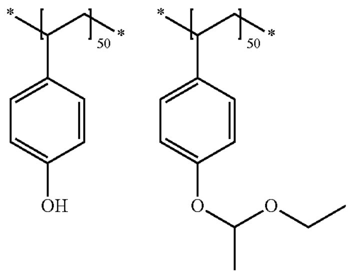

Mw = 12000, Mw/Mn = 1.2

-continued
P-2
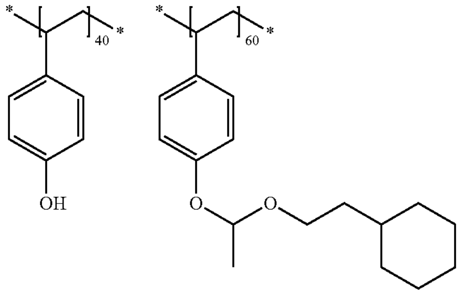
Mw = 4800, Mw/Mn = 1.2
P-3
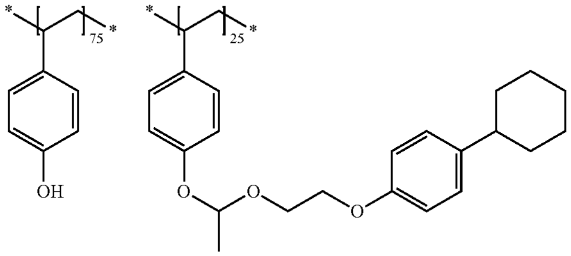
Mw = 11000, Mw/Mn = 1.1
P-4
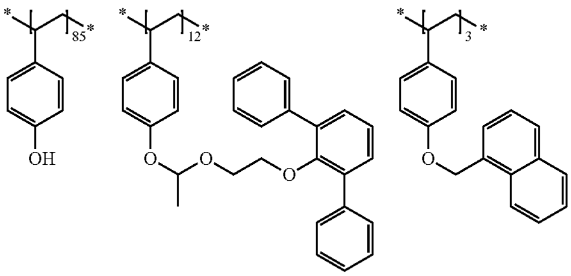
Mw = 11000, Mw/Mn = 1.1
P-5
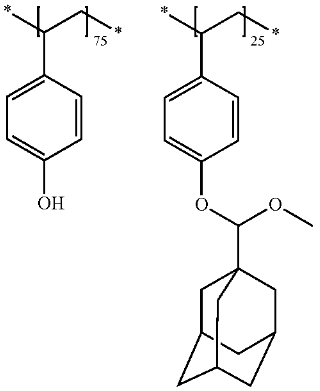
Mw = 4800, Mw/Mn = 1.2
-continued
P-6
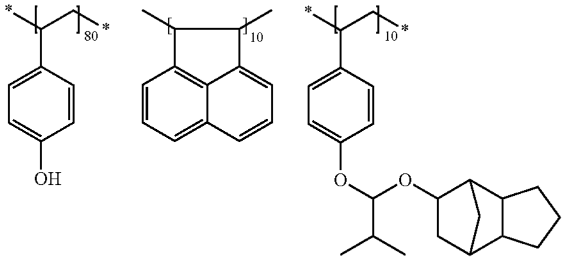
Mw = 5500, Mw/Mn = 1.5
P-7
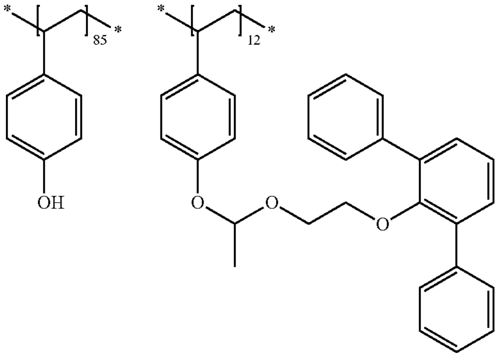
Mw = 10000, Mw/Mn = 1.1
P-8
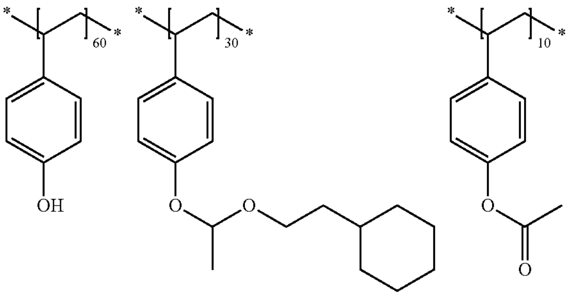
Mw = 4800, Mw/Mn = 1.1
P-9
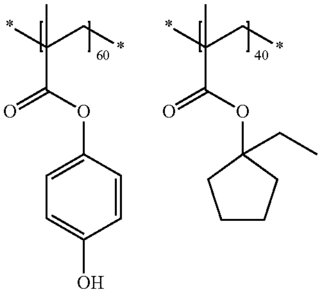
Mw = 4800, Mw/Mn = 1.3

-continued

P-10

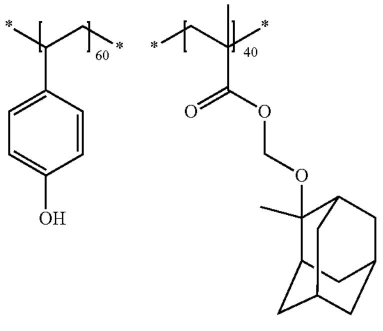

Mw = 5700, Mw/Mn = 1.3

P-11

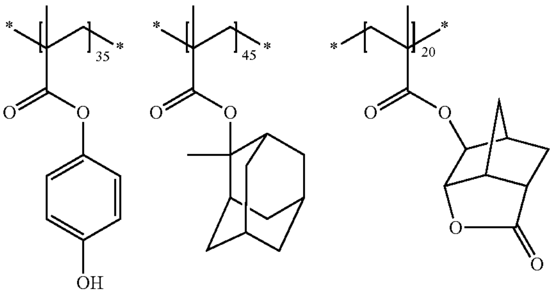

Mw = 6500, Mw/Mn = 1.3

P-12

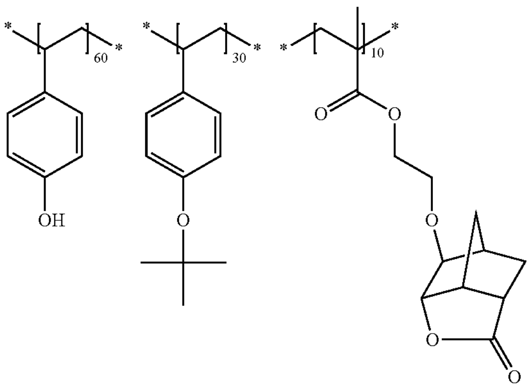

Mw = 7500, Mw/Mn = 1.3

[Basic Compound]

B1: tetrabutyl ammonium hydroxide

B2: tri(n-octyl) amine

B3: 2,4,5-triphenyl imidazole

B4:

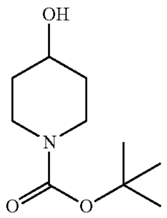

B5:

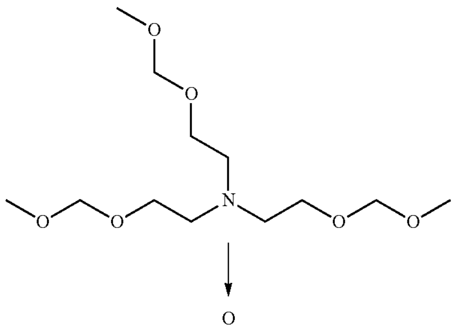

B6:

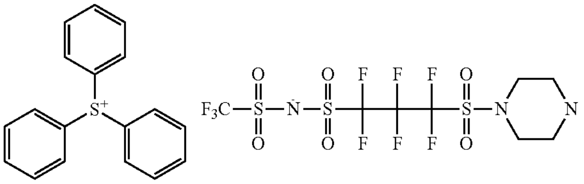

[Surfactant]

W-1: PF6320 (produced by Omnova Solutions Inc.)

W-2: Megafac F176 (produced by DIC Corporation; fluorine-based)

W-3: Polysiloxane polymer KP-341 (produced by Shin-Etsu Chemical Co., Ltd.; silicon-based)

[Solvent]

S1: Propylene glycol monomethyl ether acetate (1-methoxy-2-acetoxypropane)

S2: Propylene glycol monomethyl ether (1-methoxy-2-propanol)

S3: 2-heptanone

S4: Ethyl lactate

S5: Cyclohexanone

S6: γ-butyrolactone

S7: Propylene carbonate

The evaluation results are shown in Table 5.

TABLE 5

[Electron beam exposure; positive type]

| Example | Composition | Sensitivity (μC/cm$^2$) | LS Resolving Power (nm) | IL Resolving Power (nm) | Pattern Forming | LER (nm) |
|---|---|---|---|---|---|---|
| 1P | P1 | 10.8 | 22 | 25 | Rectangle | 3.5 |
| 2P | P2 | 10.9 | 22 | 25 | Rectangle | 3.5 |
| 3P | P3 | 10.7 | 20 | 25 | Rectangle | 3.8 |
| 4P | P4 | 10.7 | 22 | 25 | Rectangle | 3.5 |
| 5P | P5 | 11.8 | 22 | 25 | Rectangle | 3.5 |
| 6P | P6 | 10.8 | 22 | 25 | Rectangle | 3.5 |
| 7P | P7 | 10.7 | 20 | 25 | Rectangle | 3.8 |
| 8P | P8 | 10.8 | 22 | 25 | Rectangle | 3.5 |
| 9P | P9 | 10.9 | 20 | 25 | Rectangle | 3.8 |
| 10P | P10 | 10.8 | 20 | 25 | Rectangle | 3.8 |
| 11P | P11 | 10.8 | 22 | 25 | Rectangle | 3.5 |
| 12P | P12 | 10.8 | 20 | 25 | Rectangle | 3.8 |
| 13P | P13 | 10.7 | 20 | 25 | Rectangle | 3.8 |
| 14P | P14 | 10.8 | 20 | 25 | Rectangle | 3.8 |
| 15P | P15 | 10.8 | 20 | 25 | Rectangle | 3.8 |
| 16P | P16 | 10.6 | 22 | 25 | Rectangle | 3.5 |
| 17P | P17 | 10.8 | 22 | 25 | Rectangle | 3.5 |
| 18P | P18 | 10.6 | 22 | 25 | Rectangle | 3.5 |
| 19P | P19 | 10.6 | 20 | 25 | Rectangle | 3.8 |
| 20P | P20 | 10.8 | 20 | 25 | Rectangle | 3.8 |
| 21P | P21 | 10.8 | 20 | 25 | Rectangle | 3.8 |
| 22P | P22 | 10.8 | 22 | 25 | Rectangle | 3.5 |
| 23P | P23 | 11.8 | 22 | 25 | Rectangle | 3.5 |
| 24P | P24 | 10.8 | 20 | 25 | Rectangle | 3.8 |
| 25P | P25 | 10.7 | 20 | 25 | Rectangle | 3.8 |
| 26P | P26 | 10.8 | 20 | 25 | Rectangle | 3.8 |
| 27P | P27 | 10.9 | 20 | 25 | Rectangle | 3.8 |
| Comparative Example 1P | Comparative Composition P1 | 10.9 | 30 | 35 | Forward taper | 5.0 |
| Comparative Example 2P | Comparative Composition P2 | 10.9 | 30 | 35 | Forward taper | 5.0 |
| Comparative Example 3P | Comparative Composition P3 | 10.9 | 30 | 35 | Slightly forward taper | 4.5 |
| Comparative Example 4P | Comparative Composition P4 | 10.8 | 30 | 35 | Slightly forward taper | 4.6 |

From the results shown in Table 5, it is understood that the composition according to the present invention is excellent in resolving power, pattern shape, and LER. In addition, it is understood that Examples 1P, 2P, 4P to 6P, 8P, 11P, 16P to 18P, 22P, and 23P which used a compound where $X_1$ or $X_2$ was a group represented by —S— in General Formula (I) or (II) are particularly excellent in LER performance, while Examples 3P, 7P, 9P, 10P, 12P to 15P, 19P to 21P, and 24P to 27P which used a compound where $X_1$ or $X_2$ was a group represented by —NH— or —$NR^1$— in General Formula (I) or (II) are particularly excellent in resolving power.

Examples 1Q to 11Q and Comparative Examples 1Q to 4Q (Preparation of Resist Solution)

A positive type resist solution was prepared by filtering the positive type resist composition shown in Table 4 above through a polytetrafluoroethylene filter having a pore size of 0.04 μm.

(Resist Evaluation)

The prepared positive type resist solution was evenly coated on a silicon substrate subjected to a hexamethyldisilazane treatment using a spin coater, and a resist film having a film thickness of 50 nm was formed by heating and drying on a hot plate for 60 seconds at 100° C.

The sensitivity, the resolving power, the pattern shape, and the line edge roughness (LER) of the obtained resist film were evaluated using the following methods.

[Sensitivity]

After performing exposure on the obtained resist film via a reflective-type mask with a 1:1 line and space pattern with a line width of 50 nm while changing the exposure amount by 0.1 mJ/cm$^2$ at a time in a range of 0 mJ/cm$^2$ to 20.0 mJ/cm$^2$ using EUV light (wavelength 13 nm), baking was carried out for 90 seconds at 110° C. Thereafter, development was carried out by using a 2.38 mass % tetramethyl ammonium hydroxide (TMAH) aqueous solution.

The exposure amount for reproducing a 1:1 line and space mask pattern with a line width of 50 nm was set as the sensitivity. The smaller this value is, the higher the sensitivity.

[LS Resolving Power]

The limit resolving power (the minimum line width at which the lines and spaces are separately resolved) in the exposure amount indicating the sensitivity described above was set as the LS resolving power (nm).

[Pattern Shape]

The cross-sectional shape of a 1:1 line and space resist pattern with a line width of 50 nm in the exposure amount indicating the sensitivity described above was observed using a scanning electron microscope (S-4300 manufactured by Hitachi, Ltd.). In the cross-sectional shape of the line pattern, for the ratio represented by [the line width in the bottom section of the line pattern/the line width in the center section (the height position of half the height of the line pattern) of the line pattern], a line pattern having a ratio of 1.2 or more was set as a "forward taper", a line pattern having a ratio of a ratio of 1.05 or more to less than 1.2 was set as a "slightly forward taper", and a line pattern having a ratio of a ratio of less than 1.05 was set as a "rectangle", and evaluation was performed.

[Line Edge Roughness (LER)]

A 1:1 line and space resist pattern with a line width of 50 nm was formed with the exposure amount indicating the sensitivity described above. Then, for an arbitrary 30 points in 10 μm in the length direction, the distance from a reference line where an edge should be present was measured using a scanning electron microscope (S-9220 manufactured by Hitachi, Ltd.). Then, the standard deviation of this distance was determined and 3σ was calculated. A smaller value indicates a more favorable performance.

TABLE 6

[EUV exposure; positive type]

| | Composition | Sensitivity ($mJ/cm^2$) | LS resolving power (nm) | Pattern Forming | LER (nm) |
|---|---|---|---|---|---|
| 1Q | P1 | 10.8 | 20 | Rectangle | 3.5 |
| 2Q | P2 | 10.8 | 20 | Rectangle | 3.5 |
| 3Q | P10 | 10.8 | 18 | Rectangle | 3.8 |
| 4Q | P11 | 10.7 | 20 | Rectangle | 3.5 |
| 5Q | P14 | 10.8 | 18 | Rectangle | 3.8 |
| 6Q | P15 | 10.8 | 18 | Rectangle | 3.8 |
| 7Q | P16 | 10.7 | 20 | Rectangle | 3.5 |
| 8Q | P17 | 10.8 | 20 | Rectangle | 3.5 |
| 9Q | P12 | 10.9 | 18 | Rectangle | 3.8 |
| 10Q | P26 | 10.8 | 18 | Rectangle | 3.8 |
| 11Q | P27 | 10.8 | 18 | Rectangle | 3.8 |
| Comparative Example 1Q | Comparative Compound P1 | 10.9 | 30 | Forward taper | 5.0 |
| Comparative Example 2Q | Comparative Compound P2 | 10.9 | 30 | Forward taper | 5.0 |
| Comparative Example 3Q | Comparative Compound P3 | 13.9 | 30 | Slightly Forward taper | 5.0 |
| Comparative Example 4Q | Comparative Compound P4 | 13.9 | 30 | Slightly Forward taper | 5.0 |

From the results shown in Table 6, it is understood that the composition according to the present invention is excellent in resolving power, pattern shape, and line edge roughness (LER) performance. In addition, it is understood that Examples 1Q, 2Q, 4Q, 7Q, and 8Q which used a compound where $X_1$ or $X_2$ was a group represented by —S— in General Formula (I) or (II) are particularly excellent in the LER performance, while Examples 3Q, 5Q, 6Q, and 9Q to 11Q which used a compound where $X_1$ or $X_2$ was a group represented by —NH— or —$NR^1$— in General Formula (I) or (II) are particularly excellent in resolving power.

(1) Preparation of Support Body

A 6-inch wafer on which Cr oxide was deposited (a wafer subjected to a film shielding process used for conventional photomask blanks) was prepared.

Example 1E (2) Preparation of Resist Coating Solution (Coating Liquid Composition of Negative Type Resist Composition N1)

| | |
|---|---|
| Resin (P'-4) | 4.21 g |
| Compound (A1) (photoacid generator, structural formula described above) | 0.47 g |
| Cross-linking agent CL-1 (structural formula described below) | 0.59 g |
| Cross-linking agent CL-4 (structural formula described below) | 0.30 g |
| Tetrabutyl ammonium hydroxide (basic compound) | 0.04 g |
| 2-hydroxy-3-naphthoic acid (organic carboxylic acid) | 0.11 g |

-continued

| | |
|---|---|
| Surfactant PF6320 (produced by Omnova Solutions Inc.) | 0.005 g |
| Propylene glycol monomethyl ether acetate (solvent) | 75.0 g |
| Propylene glycol monomethyl ether (solvent) | 18.8 g |

A resist coating solution was obtained by passing the composition solution described above through a microfilter with a polytetrafluoroethylene filter which has a pore size of 0.04 μm.

(3) Creation of Resist Film

A resist film with a film thickness of 50 nm was obtained by coating the 6-inch wafers described above with a resist coating solution using a spin coater Mark 8 manufactured by Tokyo Electron Ltd., and carrying out drying on a hot plate for 90 seconds at 110° C. That is, a resist-coated mask blank was obtained.

(4) Preparation of Negative Type Resist Pattern

Pattern irradiation was performed on this resist film using an electron beam drawing apparatus (ELS-7500 manufactured by Elionix Inc., acceleration voltage 50 KeV). After the irradiation, heating was carried out on a hot plate for 90 seconds at 120° C., and immersion was carried out for 60 seconds using a 2.38 mass % tetramethyl ammonium hydroxide (TMAH) solution, rinsing was carried out for 30 seconds with water, and drying was carried out.

(5) Resist Pattern Evaluation

The sensitivity, the resolving power, the pattern shape, and the line edge roughness (LER) of the obtained pattern were evaluated using the following methods.

[Sensitivity]

The cross-sectional shape of the obtained pattern was observed using a scanning electron microscope (S-4300 manufactured by Hitachi, Ltd.). The exposure amount (the electron beam irradiation amount) when resolving a 1:1 line and space resist pattern with a line width of 50 nm was set as the sensitivity. The smaller this value is, the higher the sensitivity.

[LS Resolving Power]

The limit resolving power (the minimum line width at which the lines and spaces are separately resolved) in the exposure amount (the electron beam irradiation amount) indicating the sensitivity described above was set as the LS resolving power (nm).

[IS Resolving Power]

The limit resolving power (the minimum line width at which the spaces and lines are separately resolved) in the minimum radiation amount when resolving an isolated space pattern with a line width of 50 nm (space:line=1:>50) was set as the IS resolving power (nm).

[Pattern Shape]

The cross-sectional shape of a 1:1 line and space resist pattern with a line width of 50 nm in the exposure amount (the electron beam irradiation amount) indicating the sensitivity described above was observed using a scanning electron microscope (S-4300 manufactured by Hitachi, Ltd.). In the cross-sectional shape of the line pattern, for the ratio represented by [the line width in the top section (surface section) of the line pattern/the line width in the center section (the height position of half the height of the line pattern) of the line pattern], a line pattern having a ratio of 1.5 or more was set as a "reverse taper", a line pattern having a ratio of 1.2 or more to less than 1.5 was set as a "slightly reverse taper", and a line pattern having a ratio of less than 1.2 was set as a "rectangle", and evaluation was performed.

[Line Edge Roughness (LER)]

A 1:1 line and space resist pattern with a line width of 50 nm was formed with an exposure amount (the electron beam irradiation amount) indicating the sensitivity described above. Then, for an arbitrary 30 points included in 50 μm in the length direction, the distance from a reference line where an edge should be present was measured using a scanning electron microscope (S-9220 manufactured by Hitachi, Ltd.). Then, the standard deviation of this distance was determined and 3σ was calculated. A smaller value indicates a more favorable performance.

[Example 2E] to [Example 27E] and [Comparative Example 1E] to [Comparative Example 4E]

In the resist solution formula, the preparation of the resist solution (negative type resist compositions N2 to N27, negative type resist comparative compositions N1 to N4), the negative type pattern forming, and the evaluation were performed in the same manner as Example 1E except for the components described in Table 7 below.

TABLE 7

| Composition | Photoacid generator | Resin | Organic Carboxylic acid | Basic Compound | Surfactant | Cross-linking agent | Solvent |
|---|---|---|---|---|---|---|---|
| N1 | A1 (0.47 g) | P'-4 (4.21 g) | D1 (0.11 g) | B1 (0.04 g) | W-1 (0.005 g) | CL-1/CL-4 (0.59 g/0.30 g) | S1/S2 (75.0 g/18.8 g) |
| N2 | A2 (0.47 g) | P'-4 (4.21 g) | D1 (0.11 g) | B1 (0.04 g) | W-1 (0.005 g) | CL-1/CL-4 (0.59 g/0.30 g) | S1/S3 (75.0 g/18.8 g) |
| N3 | A3 (0.47 g) | P'-4 (4.21 g) | D1 (0.11 g) | B1 (0.04 g) | W-1 (0.005 g) | CL-1/CL-4 (0.59 g/0.30 g) | S2/S3 (75.0 g/18.8 g) |
| N4 | A4 (0.47 g) | P'-4 (4.21 g) | D1 (0.11 g) | B1 (0.04 g) | W-1 (0.005 g) | CL-1/CL-4 (0.59 g/0.30 g) | S2/S7 (75.0 g/18.8 g) |
| N5 | A5 (0.47 g) | P'-4 (4.21 g) | D1 (0.11 g) | B1 (0.04 g) | W-1 (0.005 g) | CL-1/CL-4 (0.59 g/0.30 g) | S2/S1 (75.0 g/18.8 g) |
| N6 | A6 (0.47 g) | P'-4 (4.21 g) | D1 (0.11 g) | B1 (0.04 g) | W-1 (0.005 g) | CL-1/CL-4 (0.59 g/0.30 g) | S2/S1 (75.0 g/18.8 g) |
| N7 | A7 (0.47 g) | P'-4 (4.21 g) | D1 (0.11 g) | B1 (0.04 g) | W-1 (0.005 g) | CL-1/CL-4 (0.59 g/0.30 g) | S2/S1 (75.0 g/18.8 g) |
| N8 | A8 (0.47 g) | P'-4 (4.21 g) | D1 (0.11 g) | B1 (0.04 g) | W-1 (0.005 g) | CL-1/CL-4 (0.59 g/0.30 g) | S2/S1 (75.0 g/18.8 g) |
| N9 | A9 (0.47 g) | P'-4 (4.21 g) | D1 (0.11 g) | B1 (0.04 g) | W-1 (0.005 g) | CL-1/CL-4 (0.59 g/0.30 g) | S2/S1 (75.0 g/18.8 g) |
| N10 | A10 (0.47 g) | P'-4 (4.21 g) | D1 (0.11 g) | B1 (0.04 g) | W-1 (0.005 g) | CL-1/CL-4 (0.59 g/0.30 g) | S2/S1 (75.0 g/18.8 g) |
| N11 | A11 (0.47 g) | P'-4 (4.21 g) | D1 (0.11 g) | B1 (0.04 g) | W-1 (0.005 g) | CL-1/CL-4 (0.59 g/0.30 g) | S2/S1 (75.0 g/18.8 g) |
| N12 | A12 (0.47 g) | P'-4 (4.21 g) | D1 (0.11 g) | B1 (0.04 g) | W-1 (0.005 g) | CL-1/CL-4 (0.59 g/0.30 g) | S1/S2/S6 (50.0 g/25.0 g/18.8 g) |
| N13 | A13 (0.47 g) | P'-4 (4.21 g) | D1 (0.11 g) | B1 (0.04 g) | W-1 (0.005 g) | CL-1/CL-4 (0.59 g/0.30 g) | S1/S2/S5 (50.0 g/25.0 g/18.8 g) |
| N14 | A14 (0.47 g) | P'-4 (4.21 g) | D1 (0.11 g) | B1 (0.04 g) | W-1 (0.005 g) | CL-1/CL-4 (0.59 g/0.30 g) | S1/S2/S4 (50.0 g/25.0 g/18.8 g) |
| N15 | A3 (0.47 g) | P'-1 (4.21 g) | D1 (0.11 g) | B2 (0.04 g) | W-1 (0.005 g) | CL-1/CL-4 (0.59 g/0.30 g) | S2/S1 (75.0 g/18.8 g) |
| N16 | A1 (0.47 g) | P'-7 (5.10 g) | None | B3 (0.04 g) | None | None | S2/S1 (75.0 g/18.8 g) |
| N17 | A1 (0.47 g) | P'-5 (4.21 g) | D1 (0.11 g) | B1 (0.04 g) | None | CL-3 (0.89 g) | S2/S1 (75.0 g/18.8 g) |
| N18 | A1 (0.47 g) | P'-2 (4.21 g) | D1 (0.11 g) | B1/B6 (0.02 g/0.02 g) | None | CL-1/CL-5 (0.59 g/0.30 g) | S2/S1 (75.0 g/18.8 g) |
| N19 | A1 (0.47 g) | P'-3 (4.21 g) | D1 (0.11 g) | B5 (0.04 g) | None | CL-2/CL-3 (0.59 g/0.30 g) | S2/S1 (75.0 g/18.8 g) |
| N20 | A1 (0.47 g) | P'-5 (4.21 g) | D1 (0.11 g) | B4 (0.04 g) | None | CL-3 (0.89 g) | S2/S1 (75.0 g/18.8 g) |
| N21 | A1 (0.47 g) | P'-6 (4.21 g) | D2 (0.11 g) | B1 (0.04 g) | W-2 (0.005 g) | CL-1/CL-5 (0.59 g/0.30 g) | S2/S1 (75.0 g/18.8 g) |
| N22 | A3 (0.47 g) | P'-3 (4.21 g) | D2 (0.11 g) | B3 (0.04 g) | W-3 (0.005 g) | CL-3 (0.89 g) | S2/S1 (75.0 g/18.8 g) |
| N23 | A1/A2 (0.20 g/0.27 g) | P'-1/ P'-3 (2.0 g/2.21 g) | D3 (0.11 g) | B2 (0.04 g) | None | CL-2 (0.89 g) | S2/S1 (75.0 g/18.8 g) |
| N24 | A15 (0.47 g) | P'-4 (4.21 g) | D1 (0.11 g) | B1 (0.04 g) | W-1 (0.005 g) | CL-1/CL-4 (0.59 g/0.30 g) | S1/S2/S4 (50.0 g/25.0 g/18.8 g) |

TABLE 7-continued

| Composition | Photoacid generator | Resin | Organic Carboxylic acid | Basic Compound | Surfactant | Cross-linking agent | Solvent |
|---|---|---|---|---|---|---|---|
| N25 | A16 (0.47 g) | P'-4 (4.21 g) | D1 (0.11 g) | B1 (0.04 g) | W-1 (0.005 g) | CL-1/CL-4 (0.59 g/0.30 g) | S1/S2/S4 (50.0 g/25.0 g/18.8 g) |
| N26 | A17 (0.47 g) | P'-4 (4.21 g) | D1 (0.11 g) | B1 (0.04 g) | W-1 (0.005 g) | CL-1/CL-4 (0.59 g/0.30 g) | S1/S2 (75.0 g/18.8 g) |
| N27 | A.18 (0.47 g) | P'-4 (4.21 g) | D1 (0.11 g) | B1 (0.04 g) | W-1 (0.005 g) | CL-1/CL-4 (0.59 g/0.30 g) | S1/S3 (75.0 g/18.8 g) |
| Comparative Composition N1 | Comparative Compound 1(0.47 g) | P'-2 (4.80 g) | D1 (0.11 g) | B2 (0.04 g) | W-1 (0.005 g) | CL-3 (0.89 g) | S1 (93.8 g) |
| Comparative Composition N2 | Comparative Compound 2(0.47 g) | P'-2 (4.21 g) | D1 (0.11 g) | B2 (0.04 g) | W-1 (0.005 g) | CL-3 (0.89 g) | S1 (93.8 g) |
| Comparative Composition N3 | Comparative Compound 3(0.47 g) | P'-2 (4.21 g) | D1 (0.11 g) | B2 (0.04 g) | W-1 (0.005 g) | CL-3 (0.89 g) | S1 (93.8 g) |
| Comparative Composition N4 | Comparative Compound 4(0.47 g) | P'-2 (4.21 g) | D1 (0.11 g) | B2 (0.04 g) | W-1 (0.005 g) | CL-3 (0.89 g) | S1 (93.8 g) |

Other components used in the Examples and Comparative Examples are shown below.

The structure of the resin, composition ratio (molar ratio), weight-average molecular weight, and degree of dispersity used in the Examples and the Comparative Examples are shown below.

[Resin]

P'-1

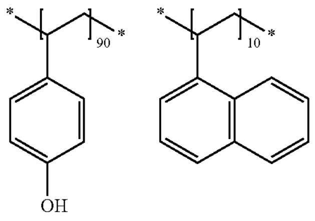

Mw = 12000, Mw/Mn = 2.3

P'-2

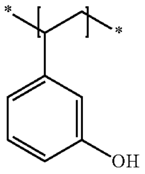

Mw = 4500, Mw/Mn = 1.1

P'-3

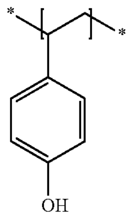

Mw = 3700, Mw/Mn = 1.1

-continued

P'-4

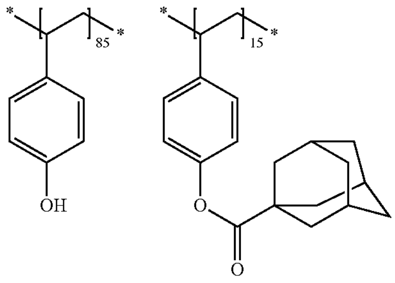

Mw = 4200, Mw/Mn = 1.1

P'-5

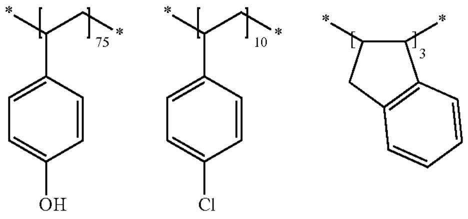

Mw = 4500, Mw/Mn = 1.5

P'-6

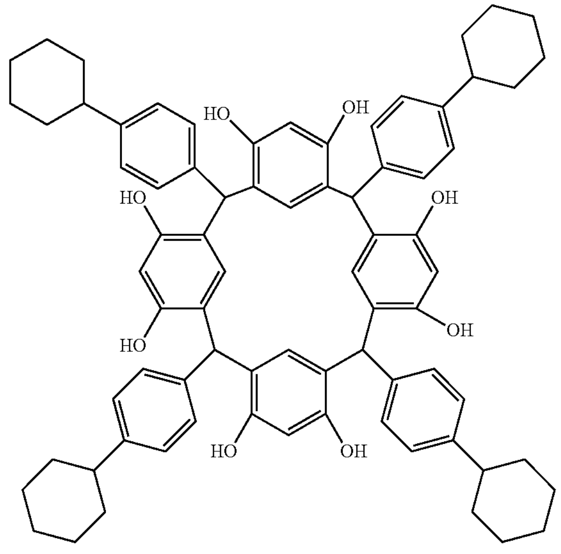

Mw = 3900, Mw/Mn = 1.1

-continued

P'-7

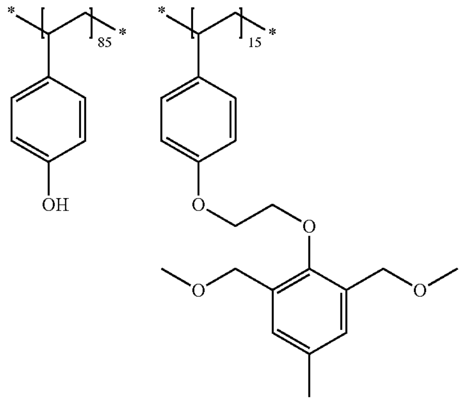

Mw = 3900, Mw/Mn = 1.1

[Cross-Linking Agent]

CL-1

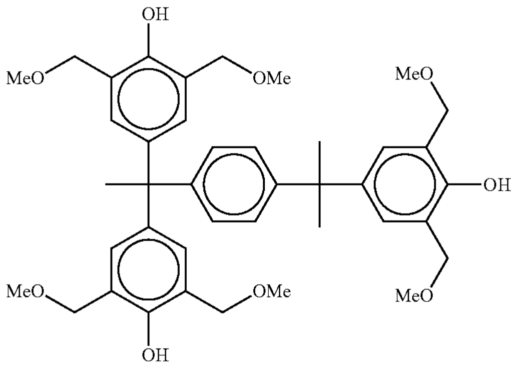

CL-2

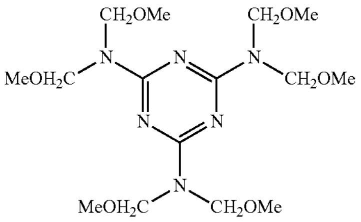

CL-3

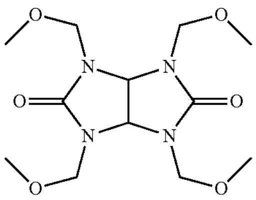

CL-4

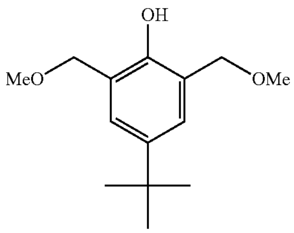

-continued

CL-5

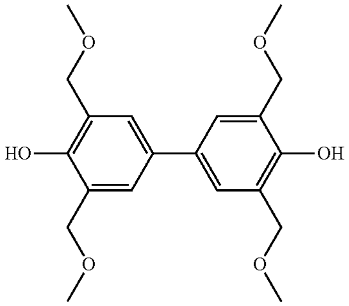

[Basic Compound]

B1: Tetrabutyl ammonium hydroxide

B2: Tri(n-octyl) amine

B3: 2,4,5-triphenyl imidazole

B4:

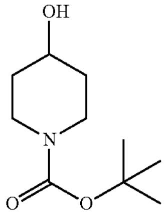

B5:

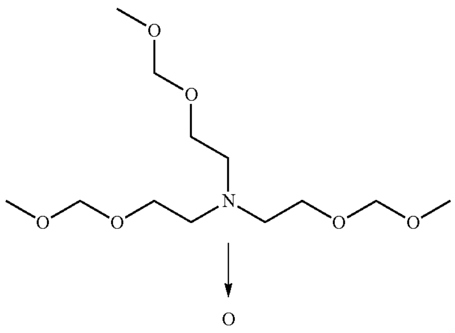

B6:

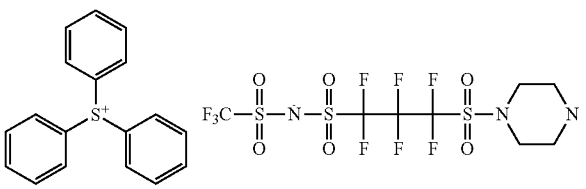

[Organic Carboxylic Acid]

D1: 2-hydroxy-3-naphthoic acid

D2: 2-naphthoic acid

D3: benzoic acid

[Surfactant]

W-1: PF6320 (produced by Omnova Solutions Inc.)

W-2: Megafac F176 (produced by DIC Corporation; fluorine-based)

W-3: Polysiloxane polymer KP-341 (produced by Shin-Etsu Chemical Co., Ltd.; silicon-based)

[Solvent]

S1: Propylene glycol monomethyl ether acetate (1-methoxy-2-acetoxypropane)

S2: Propylene glycol monomethyl ether (1-methoxy-2-propanol)

S3: 2-heptanone

S4: Ethyl lactate

S5: Cyclohexanone

S6: γ-butyrolactone

S7: Propylene carbonate

TABLE 8

(Electron beam exposure; negative type)

| Example | Composition | Sensitivity ($\mu C/cm^2$) | LS Resolving Power (nm) | IS Resolving Power (nm) | Pattern Forming | LER (nm) |
|---|---|---|---|---|---|---|
| 1E | N1 | 10.2 | 22 | 25 | Rectangle | 3.5 |
| 2E | N2 | 10.0 | 22 | 25 | Rectangle | 3.5 |
| 3E | N3 | 10.2 | 20 | 25 | Rectangle | 3.8 |
| 4E | N4 | 10.2 | 22 | 25 | Rectangle | 3.5 |
| 5E | N5 | 11.3 | 22 | 25 | Rectangle | 3.5 |
| 6E | N6 | 10.3 | 22 | 25 | Rectangle | 3.5 |
| 7E | N7 | 10.0 | 20 | 25 | Rectangle | 3.8 |
| 8E | N8 | 10.2 | 22 | 25 | Rectangle | 3.5 |
| 9E | N9 | 10.2 | 20 | 25 | Rectangle | 3.8 |
| 10E | N10 | 10.2 | 20 | 25 | Rectangle | 3.8 |
| 11E | N11 | 10.3 | 22 | 25 | Rectangle | 3.5 |
| 12E | N12 | 10.2 | 20 | 25 | Rectangle | 3.8 |
| 13E | N13 | 10.3 | 20 | 25 | Rectangle | 3.8 |
| 14E | N14 | 11.3 | 20 | 25 | Rectangle | 3.8 |
| 15E | N15 | 10.3 | 20 | 25 | Rectangle | 3.8 |
| 16E | N16 | 10.2 | 22 | 25 | Rectangle | 3.5 |
| 17E | N17 | 10.3 | 22 | 25 | Rectangle | 3.5 |
| 18E | N18 | 10.5 | 22 | 25 | Rectangle | 3.5 |
| 19E | N19 | 10.2 | 22 | 25 | Rectangle | 3.5 |
| 20E | N20 | 10.2 | 22 | 25 | Rectangle | 3.5 |
| 21E | N21 | 10.3 | 22 | 25 | Rectangle | 3.5 |
| 22E | N22 | 10.2 | 20 | 25 | Rectangle | 3.8 |
| 23E | N23 | 10.4 | 22 | 25 | Rectangle | 3.5 |
| 24E | N24 | 10.3 | 20 | 25 | Rectangle | 3.8 |
| 25E | N25 | 10.3 | 20 | 25 | Rectangle | 3.8 |
| 26E | N26 | 10.2 | 20 | 25 | Rectangle | 3.8 |
| 27E | N27 | 10.0 | 20 | 25 | Rectangle | 3.8 |
| Comparative Example 1E | Comparative Composition N1 | 11.8 | 35 | 40 | Reverse taper | 4.5 |
| Comparative Example 2E | Comparative Composition N2 | 11.9 | 35 | 40 | Reverse taper | 4.5 |
| Comparative Example 3E | Comparative Composition N3 | 11.8 | 35 | 40 | Slightly reverse taper | 4.5 |
| Comparative Example 4E | Comparative Composition N4 | 11.5 | 35 | 40 | Slightly reverse taper | 4.5 |

From the results shown in Table 8, it is understood that the composition according to the present invention is excellent in sensitivity, resolving power, pattern shape, and LER performance. In addition, it is understood that Examples 1E, 2E, 4E to 6E, 8E, 11E, 16E to 21E, and 23E which used a compound where $X_1$ or $X_2$ was a group represented by —S— in General Formula (I) or (II) are particularly excellent in the LER performance, while Examples 3E, 7E, 9E, 10E, 12E to 15E, 22E, 24E to 27E which used a compound where $X_1$ or $X_2$ was a group represented by —NH— or —$NR^1$— in General Formula (I) or (II) are particularly excellent in resolving power.

Example 1F-8F and Comparative Examples 1F-4F (Preparation of Resist Solution)

A negative type resist solution was prepared by filtering the negative type resist composition shown in Table 7 above through a polytetrafluoroethylene filter having a pore size of 0.04 μm.

(Resist Evaluation)

The prepared negative type resist solution was evenly coated on a silicon substrate subjected to a hexamethyldisilazane treatment using a spin coater, and a resist film having a film thickness of 50 nm was formed by heating and drying on a hot plate for 60 seconds at 100*C.

The sensitivity, the resolving power, the pattern shape, and the line edge roughness (LER) of the obtained resist film were evaluated using the following methods.

[Sensitivity]

After performing exposure on the obtained resist film via a reflective-type mask with a 1:1 line and space pattern with a line width of 50 nm while changing the exposure amount by 0.1 $mJ/cm^2$ at a time in a range of 0 $mJ/cm^2$ to 20.0 $mJ/cm^2$ using EUV light (wavelength 13 nm), baking was carried out for 90 seconds at 110° C. Thereafter, development was carried out by using a 2.38 mass % tetramethyl ammonium hydroxide (TMAH) aqueous solution.

The exposure amount for reproducing a 1:1 line and space mask pattern with a line width of 50 nm was set as the sensitivity. The smaller this value is, the higher the sensitivity.

[LS Resolving Power]

The limit resolving power (the minimum line width at which the lines and spaces are separately resolved) in the exposure amount indicating the sensitivity described above was set as the LS resolving power (nm).

[Pattern Shape]

The cross-sectional shape of a 1:1 line and space resist pattern with a line width of 50 nm in the exposure amount indicating the sensitivity described above was observed using a scanning electron microscope (S-4300 manufactured by Hitachi, Ltd.). In the cross-sectional shape of the line pattern, for the ratio represented by [the line width in the top section (surface section) of the line pattern/the line width in the center section (the height position of half the height of the line pattern) of the line pattern], a line pattern having a ratio of 1.5 or more was set as a “reverse taper”, a line pattern having a ratio of 1.2 or more to less than 1.5 was set as a “slightly reverse taper”, and a line pattern having a ratio of less than 1.2 was set as a “rectangle”, and evaluation was performed.

[Line Edge Roughness (LER)]

A 1:1 line and space resist pattern with a line width of 50 nm was formed with the exposure amount indicating the sensitivity described above. Then, for an arbitrary 30 points in 10 μm in the length direction, the distance from a reference line where an edge should be present was measured using a scanning electron microscope (S-9220 manufactured by Hitachi, Ltd.). Then, the standard deviation of this distance was determined and 3σ was calculated. A smaller value indicates a more favorable performance.

Surfactant PF6320 (manufactured by Omnova Solutions Inc.) 0.001 g

Propylene glycol monomethyl ether acetate (solvent) 5.4 g

Propylene glycol monomethyl ether (solvent) 3.6 g (Preparation of Resist Solution)

A resist solution was prepared by filtering a resist composition adjusted based on the coating solution composition described above through a polytetrafluoroethylene filter having a pore size of 0.04 μm.

(Resist Evaluation)

The prepared resist solution was evenly coated on a silicon substrate subjected to a hexamethyldisilazane treatment using a spin coater, and a resist film having a film thickness of 50 nm was formed by heating and drying on a hot plate for 60 seconds at 100° C.

The sensitivity, the resolving power, the pattern shape, and the line edge roughness (LER) of the obtained resist film were evaluated using the following methods.

[Sensitivity]

After performing exposure on the obtained resist film via a reflective-type mask with a 1:1 line and space pattern with a line width of 50 nm while changing the exposure amount by 0.1 $mJ/cm^2$ at a time in a range of 0 $ml/cm^2$ to 20.0 $mJ/cm^2$ using EUV light (wavelength 13 nm), baking was carried out for 90 seconds at 110° C. Thereafter, the organic-based developer described in the Table below was developed for 30 seconds by paddling, and rinsed using the rinsing liquids described in the Table below, then the wafer was rotated for 30 seconds at a rotation speed of 4,000 rpm, then a pattern was formed by performing baking for 60 seconds at 90° C.

The exposure amount for reproducing a 1:1 line and space mask pattern with a line width of 50 nm was set as the sensitivity. The smaller this value is, the higher the sensitivity.

[LS Resolving Power]

The limit resolving power (the minimum line width at which the lines and spaces are separately resolved) in the exposure amount indicating the sensitivity described above was set as the LS resolving power (nm).

[Pattern Shape]

The cross-sectional shape of a 1:1 line and space resist pattern with a line width of 50 nm in the exposure amount indicating the sensitivity described above was observed

TABLE 9

(EUV exposure; negative type)

| | Composition | Sensitivity ($mJ/cm^2$) | Resolving Power (nm) | Pattern Forming | LER (nm) |
|---|---|---|---|---|---|
| 1F | N1 | 12.8 | 22 | Rectangle | 4.0 |
| 2F | N2 | 12.7 | 22 | Rectangle | 4.0 |
| 3F | N3 | 12.8 | 20 | Rectangle | 4.2 |
| 4F | N12 | 12.8 | 20 | Rectangle | 4.2 |
| 5F | N14 | 12.0 | 20 | Rectangle | 4.2 |
| 6F | N22 | 12.5 | 20 | Rectangle | 4.2 |
| 7F | N26 | 12.8 | 20 | Rectangle | 4.2 |
| 8F | N27 | 12.7 | 20 | Rectangle | 4.2 |
| Comparative Example 1F | Comparative Composition N1 | 13.9 | 30 | Reverse taper | 5.0 |
| Comparative Example 2F | Comparative Composition N2 | 13.8 | 30 | Reverse taper | 5.0 |
| Comparative Example 3F | Comparative Composition N3 | 13.8 | 30 | Slightly reverse taper | 5.0 |
| Comparative Example 4F | Comparative Composition N4 | 13.5 | 30 | Slightly reverse taper | 5.0 |

From the results shown in Table 9, it is understood that the composition according to the present invention is excellent in sensitivity, resolving power, pattern shape, and LER performance. In addition, it is understood that Examples 1F and 2F which used the compound where $X_1$ or $X_2$ is —S— in the compound (A) are particularly excellent in LER performance. Furthermore, it is understood that Examples 3F to 8F which used the compound where $X_2$ or $X_2$ is —NH— or —$NR^1$— in the compound (A) are particularly excellent in resolving power.

Example 1G

Preparation of Resist Coating Solution (Coating Solution Composition of Organic Solvent-Based Negative Type Resist Composition 1D)

Acid-decomposable resin (P-13) 0.60 g

Compound (A2) (photoacid generator, structural formula described above) 0.12 g (Tri (n-octyl) amine) (basic compound) 0.002 g using a scanning electron microscope (S-4300 manufactured by Hitachi, Ltd.). In the cross-sectional shape of the line pattern, for the ratio represented by [the line width in the bottom section of the line pattern/the line width in the center section (the height position of half the height of the line pattern) of the line pattern], a line pattern having a ratio of 1.2 or more was set as a “forward taper”, a line pattern having a ratio of 1.05 or more to less than 1.2 was set as a “slightly forward taper”, and a line pattern having a ratio of less than 1.05 was set as a “rectangle”, and evaluation was performed.

[Example 2G] to [Example 14G] and [Comparative Example 1G] to [Comparative Example 4G]

In the resist solution formula, the preparation of the resist solution (negative type resist compositions 2D to 14D, negative type resist comparative compositions 1D to 4D), the negative type pattern forming, and the evaluation were performed in the same manner as Example 1G except for the components described in Table 10 below.

The evaluation results are shown in Table 11 below.

TABLE 10

[EUV exposure; organic-based developer (negative type)]

| Composition Example | Photoacid generator | Resin | Basic Compound (0.002 g) | Surfactant (0.001 g) | Solvent (9.0 g) (mass ratio) |
|---|---|---|---|---|---|
| 1D | A2(0.12 g) | P-13(0.6 g) | B2 | W-1 | S1/S2 (6/4) |
| 2D | A1(0.12 g) | P-13(0.6 g) | B2 | W-1 | S1/S2/S6 (6/3/1) |
| 3D | A7(0.12 g) | P-14(0.6 g) | B2 | W-2 | S1/S7 (6/4) |
| 4D | A8(0.12 g) | P-16(0.6 g) | B3 | W-2 | S1/S2 (6/4) |
| 5D | A10(0.12 g) | P-17(0.6 g) | B4 | W-3 | S1/S2 (6/4) |
| 6D | A11(0.12 g) | P-18(0.6 g) | B5 | W-1 | S1/S2 (6/4) |
| 7D | A12(0.12 g) | P-19(0.6 g) | B3 | W-3 | S1/S2 (6/4) |
| 8D | A2/A1 (0.06 g/0.06 g) | P-1/P-5 (0.3 g/0.3 g) | B6 | None | S1/S2 (6/4) |
| 9D | A14(0.12 g) | P-20(0.6 g) | B5 | W-1 | S1/S2 (6/4) |
| 10D | A12(0.12 g) | P-15(0.6 g) | B4 | W-1 | S1/S2 (6/4) |
| 11D | A7(0.12 g) | P-21(0.6 g) | B6 | W-1 | S1/S2 (6/4) |
| 12D | A14(0.12 g) | P-22(0.6 g) | B2 | W-1 | S1/S2 (6/4) |
| 13D | A17(0.12 g) | P-13(0.6 g) | B2 | W-1 | S1/S2 (6/4) |
| 14D | A18(0.12 g) | P-13(0.6 g) | B2 | W-1 | S1/S2/S6 (6/3/1) |
| Comparative Composition 1D | Comparative Compound 1 (0.12 g) | P-1(0.6 g) | B2 | W-1 | S1/S2 (6/4) |
| Comparative Composition 2D | Comparative Compound 2 (0.12 g) | P-1(0.6 g) | B2 | W-1 | S1/S2 (6/4) |
| Comparative Composition 3D | Comparative Compound 3 (0.12 g) | P-1(0.6 g) | B2 | W-1 | S1/S2 (6/4) |
| Comparative Composition 4D | Comparative Compound 4 (0.12 g) | P-1(0.6 g) | B2 | W-1 | S1/S2 (6/4) |

[Line Edge Roughness (LER)]

A 1:1 line and space resist pattern with a line width of 50 nm was formed with the exposure amount indicating the sensitivity described above. Then, for an arbitrary 30 points in 10 μm in the length direction, the distance from a reference line where an edge should be present was measured using a scanning electron microscope (S-9220 manufactured by Hitachi, Ltd.). Then, the standard deviation of this distance was determined and 3σ was calculated. A smaller value indicates a more favorable performance.

Abbreviations of the materials other than those described above used in the Examples/Comparative Examples described above are described below.

[Acid-Decomposable Resin]

The structure of the resin, composition ratio (molar ratio), weight-average molecular weight, and degree of dispersity used in the Examples and the Comparative Examples are shown below.

P-13
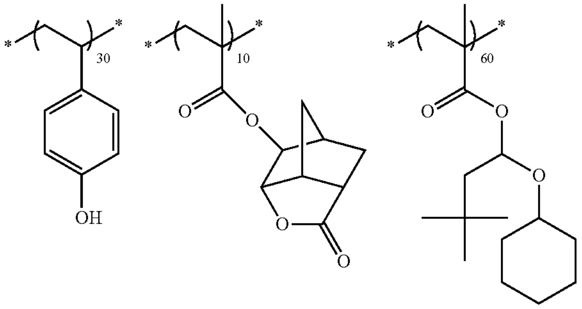
Mw = 11000
Mw/Mn = 1.42
P-14
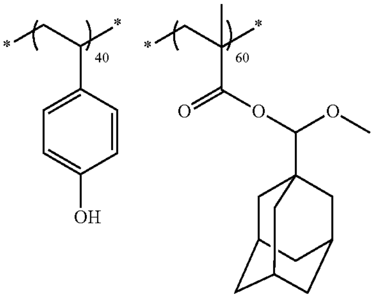
Mw = 7700
Mw/Mn = 1.55
P-15
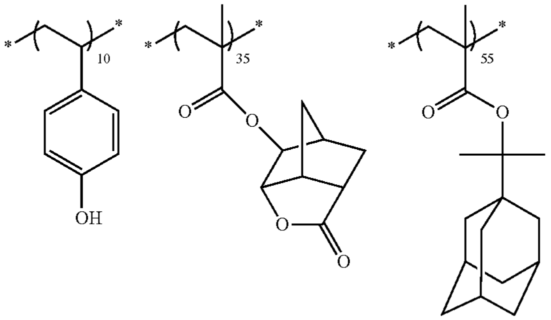
Mw = 14200
Mw/Mn = 1.64
P-16
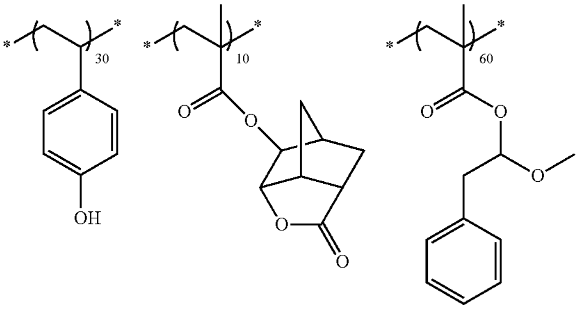
Mw =8700
Mw/Mn = 1.53
P-17
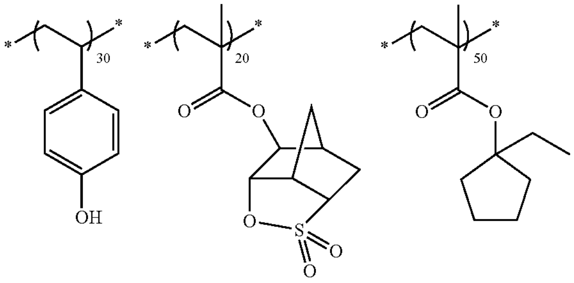
Mw = 7100
Mw/Mn = 1.56
P-18
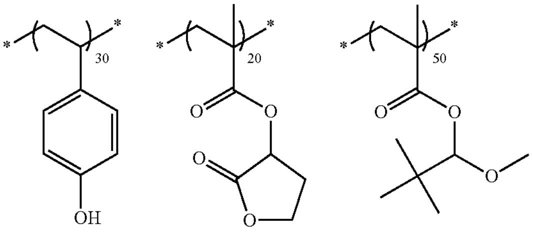
Mw = 11700
Mw/Mn = 1.43
P-19
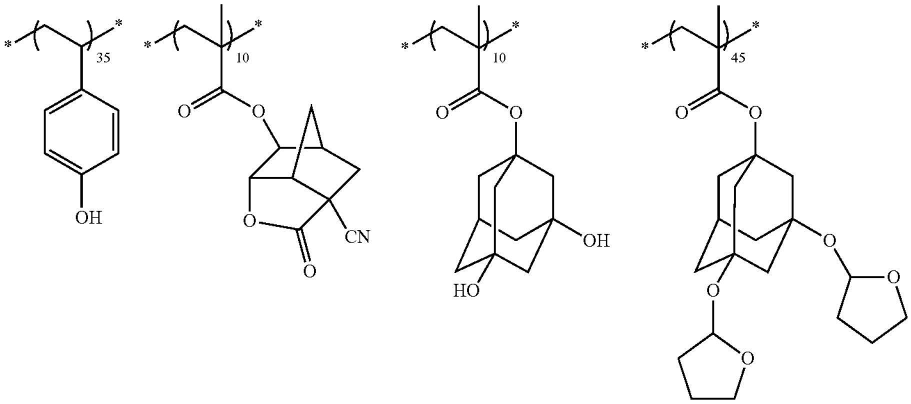
Mw = 8800
Mw/Mn = 1.58

-continued

P-20

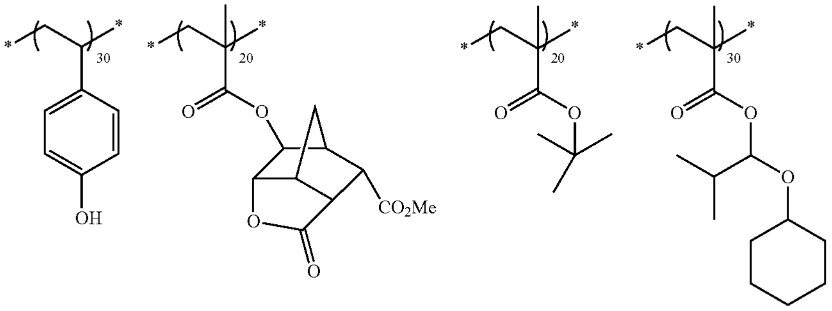

Mw = 12200
Mw/Mn = 1.61

P-21

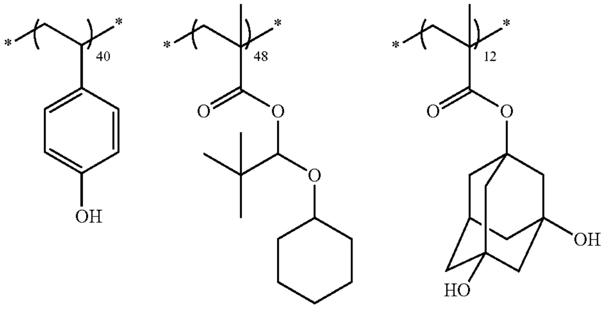

Mw = 9500
Mw/Mn = 1.48

[Developer]

As the developer, the following were used.

SG-1: 2-nonanone

SG-2: methyl amyl ketone (2-heptanone)

SG-3: butyl acetate

[Rinsing Liquid]

As the rinsing liquid, the following were used.

SR-1: 4-methyl-2-pentanol

SR-2: 1-hexanol

SR-3: methyl isobutyl carbinol

TABLE 11

(EUV exposure; Solvent Development Type)

| | Composition | Developer | Rinsing liquid | Sensitivity ($mJ/cm^2$) | LS Resolving Power (nm) | Pattern Forming | LER (nm) |
|---|---|---|---|---|---|---|---|
| 1G | 1D | SG-3 | — | 10.8 | 22 | Rectangle | 3.5 |
| 2G | 2D | SG-3 | — | 10.8 | 22 | Rectangle | 3.5 |
| 3G | 3D | SG-3 | — | 10.8 | 20 | Rectangle | 3.7 |
| 4G | 4D | SG-2 | SR-1 | 11.7 | 22 | Rectangle | 3.5 |
| 5G | 5D | SG-1 | SR-2 | 10.8 | 20 | Rectangle | 3.7 |
| 6G | 6D | SG-3 | SR-3 | 10.8 | 22 | Rectangle | 3.5 |
| 7G | 7D | SG-3 | — | 11.9 | 20 | Rectangle | 3.7 |
| 8G | 8D | SG-3 | — | 11.9 | 22 | Rectangle | 3.5 |
| 9G | 9D | SG-3 | — | 10.9 | 20 | Rectangle | 3.7 |
| 10G | 10D | SG-3 | — | 10.8 | 20 | Rectangle | 3.7 |
| 11G | 11D | SG-3 | — | 10.8 | 20 | Rectangle | 3.7 |
| 12G | 12D | SG-3 | — | 11.0 | 20 | Rectangle | 3.7 |
| 13G | 13D | SG-3 | — | 10.8 | 20 | Rectangle | 3.7 |
| 14G | 14D | SG-3 | — | 10.8 | 20 | Rectangle | 3.7 |
| Comparative Example 1G | 1D | SG-3 | — | 12.8 | 30 | Forward taper | 5.0 |
| Comparative Example 2G | 2D | SG-3 | — | 12.3 | 30 | Forward taper | 5.0 |
| Comparative Example 3G | 3D | SG-3 | — | 12.8 | 30 | Slightly forward taper | 5.0 |
| Comparative Example 4G | 4D | SG-3 | — | 12.5 | 30 | Slightly forward taper | 5.0 |

From the results shown in Table 11, it is understood that the Examples 1G to 14G which used the active light sensitive or radiation sensitive resin composition of the present invention are excellent in sensitivity, resolving power, pattern shape, and LER in comparison with Comparative Examples 1G to 4G which did not use the compound (A). Examples 1G, 2G, 4G; 6G and 8G which used the compound where $X_1$ or $X_2$ was a group represented by —S— in General Formula (I) or (II) are particularly excellent in the LER performance, while Examples 3G, 5G, 7Q, 9G to 14G which used the compound where $X_1$ or $X_2$ was a group represented by —NH— and —$NR^1$— in General Formula (I) or (II) are particularly excellent in the resolving power.

INDUSTRIAL APPLICABILITY

According to the present invention, it is possible to provide a compound and an active light sensitive or radiation sensitive resin composition which are able to form ultrafine (for example, a line width of 50 nm or less) patterns in a state in which high resolution (for example, high resolving power), excellent pattern shape, and low line edge roughness (LER) are satisfied at the same time.

In addition, according to the present invention, it is possible to provide a resist film using the active light sensitive or radiation sensitive resin composition described above, a resist-coated mask blank, a photomask, a pattern forming method, a method for manufacturing an electronic device, and an electronic device.

Detailed description was given of the present invention with reference to specific embodiments; however, it will be obvious to a person skilled in the art that it is possible to make various changes and modifications without departing from the spirit and scope of the present invention.

This application is based on Japanese Patent Application (JP 2013-145015) filed on Jul. 10, 2013 and Japanese Patent Application (JP 2014-026904) filed on Feb. 14, 2014, the contents of which are incorporated herein by reference.

What is claimed is:

1. An active light sensitive or radiation sensitive resin composition comprising:

a compound (A) represented by General Formula (I) below, (I)

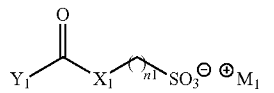

(II)

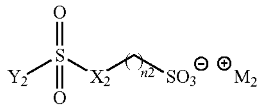

in the formula, $Y_1$ represents a monovalent organic group;

$M_1^+$ represents an organic onium ion;

$X_1$ represents a group which is represented by —S—, —NH—, or —$NR^1$—; $R^1$ represents a monovalent organic group;

n1 represents an integer of 1 or more; and $R^1$ and $Y_1$ may bond with each other to form a ring;

(B) a resin, and a solvent, wherein, in General Formula (I), $Y_1$ is a monovalent hydrocarbon group which has an alicyclic hydrocarbon structure having 5 or more carbon atoms.

2. The active light sensitive or radiation sensitive resin composition according to claim 1, wherein, in General Formula (I), $X_1$ is a group which is represented by —NH— or —$NR^1$—.

3. The active light sensitive or radiation sensitive resin composition according to claim 1, wherein, in General Formula (I), $X_1$ is a group which is represented by —S—.

4. The active light sensitive or radiation sensitive resin composition according to claim 1, wherein the resin (B) has a phenolic hydroxyl group.

5. The active light sensitive or radiation sensitive resin composition according to claim 4, wherein the resin (B) is a resin which has a repeating unit represented by General Formula (1) below:

(1)

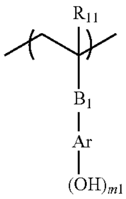

in General Formula (1), $R_{11}$ represents a hydrogen atom, a methyl group, or a halogen atom;

$B_1$ represents a single bond or a divalent linking group;

Ar represents an aromatic ring; and m1 represents an integer of 1 or more.

6. The active light sensitive or radiation sensitive resin composition according to claim 4, wherein the resin (B) is a resin which has a repeating unit represented by General Formula (A) below:

(A)

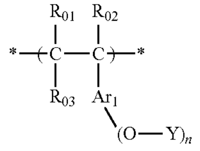

in General Formula (A), $R_{01}$, $R_{02}$, and $R_{03}$ each independently represent a hydrogen atom, an alkyl group, a cycloalkyl group, a halogen atom, a cyano group, or an alkoxycarbonyl group;

$Ar_1$ represents an aromatic ring group;

$R_{03}$ and $Ar_1$ may bond with each other to form a 5- or 6-membered ring with a main chain of the repeating unit represented by General Formula (A);

n Y's each independently represent a hydrogen atom or a group which is released due to an action of an acid;

at least one Y represents a group which is released due to an action of an acid; and n represents an integer of 1 to 4.

7. The active light sensitive or radiation sensitive resin composition according to claim 1, further comprising:

an acid cross-linkable compound (C).

8. The active light sensitive or radiation sensitive resin composition according to claim 7, wherein the compound (C) is a compound which has two or more hydroxymethyl groups or alkoxymethyl groups in a molecule.

9. The active light sensitive or radiation sensitive resin composition according to claim 1, wherein the alicyclic hydrocarbon structure is a polycyclic alicyclic hydrocarbon structure.

10. A resist film formed using the active light sensitive or radiation sensitive resin composition according to claim 1.

11. A resist-coated mask blank coated with the resist film according to claim 10.

12. A photomask obtained by exposing and developing the resist-coated mask blank according to claim 11.

13. A pattern forming method comprising:

exposing the resist film according to claim 10; and developing the exposed film.

14. A pattern forming method comprising:

exposing the resist-coated mask blank according to claim 11; and developing the exposed mask blank.

15. A method for manufacturing an electronic device, comprising:

forming a resist film on a substrate for use in the electronic device using the active light sensitive or radiation sensitive resin composition according to claim 1;

pattern-wise exposing the resist film; and developing the exposed film by using a developer to form a pattern on the substrate.

16. A compound represented by General Formula (I-I) below:

(1-I)

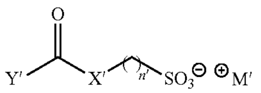

in the formula,

X' represents —S— or —NH—;

n' represents an integer of 1 to 3;

Y' represents an aryl group or a monovalent hydrocarbon group which has an alicyclic hydrocarbon structure having 5 or more carbon atoms; and $M'^{+}$ represents a sulfonium cation or an iodonium cation.

17. An active light sensitive or radiation sensitive resin composition comprising:

a compound (A) represented by General Formula (I) or (II) below, (I)

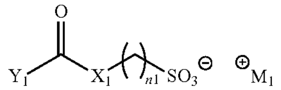

(II)

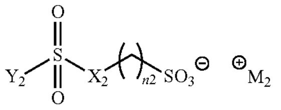

in the formulae, each of $Y_1$ and $Y_2$ represents a monovalent organic group;

each of $M_1^+$ and $M_2^+$ represents an organic onium ion;

each of $X_1$ and $X_2$ represents a group which is represented by —S—;

each of n1 and n2 represents an integer of 1 or more; and $R^1$ and $Y_1$ or $Y_2$ may bond with each other to form a ring;

(B) a resin; and a solvent.

* * * * *